United States Patent
Silbert et al.

(10) Patent No.: US 10,464,360 B2
(45) Date of Patent: Nov. 5, 2019

(54) METHOD AND APPARATUS FOR PRINTING ON AN OBJECT HAVING A CURVED SURFACE

(71) Applicant: GEN-PROBE INCORPORATED, San Diego, CA (US)

(72) Inventors: Rolf Silbert, Del Mar, CA (US); Robert Rosati, Carlsbad, CA (US); David Buse, San Diego, CA (US); Olev Tammer, New York, NY (US); Matthias Merten, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 0 days.

(21) Appl. No.: 15/669,378

(22) Filed: Aug. 4, 2017

(65) Prior Publication Data

US 2018/0022129 A1   Jan. 25, 2018

Related U.S. Application Data

(62) Division of application No. 14/919,467, filed on Oct. 21, 2015, now Pat. No. 9,724,948.

(Continued)

(51) Int. Cl.
*B41J 29/38* (2006.01)
*B41J 2/32* (2006.01)
(Continued)

(52) U.S. Cl.
CPC ............... *B41J 29/38* (2013.01); *B41J 2/32* (2013.01); *B41J 3/4073* (2013.01); *B41J 3/4075* (2013.01);
(Continued)

(58) Field of Classification Search
CPC ..... G01N 35/00732; G01N 2035/1032; G01N 2035/00861; B41J 29/38; B41J 3/4075; B41J 2/32; B41J 3/4073
See application file for complete search history.

(56) References Cited

U.S. PATENT DOCUMENTS

| | | |
|---|---|---|
| 4,091,726 A | 5/1978 | Walker |
| 4,384,518 A | 5/1983 | Albin |
| (Continued) | | |

FOREIGN PATENT DOCUMENTS

| | | |
|---|---|---|
| AU | 768222 B2 | 12/2003 |
| CN | 103612804 A | 3/2014 |
| (Continued) | | |

OTHER PUBLICATIONS

Translation of JP 2014-138994 A. (JP 2014-138994 A was published on Jul. 31, 2014.) (Year: 2014).*

(Continued)

*Primary Examiner* — Justin Seo
(74) *Attorney, Agent, or Firm* — Rothwell, Figg, Ernst & Manbeck, P.C.; Charles B. Cappellari

(57) ABSTRACT

A printing module configured to print a label on a curved surface of an article includes an expandable printing mechanism configured to be expanded to an open configuration for receiving the article or contracted to a closed configuration placing the curved surface in an operative position with respect to a print head and an article moving assembly configured to grasp and hold the article and effect relative movement between the curved surface and the print head. The printing mechanism includes contact elements, such as rollers, that contact or otherwise engage the article when the printing mechanism is in the closed configuration and maintain the curved surface in the operative position with respect (Continued)

to the print head during relative movement between the curved surface and the print head.

47 Claims, 36 Drawing Sheets

Related U.S. Application Data

(60) Provisional application No. 62/066,468, filed on Oct. 21, 2014.

(51) Int. Cl.
  *B41J 3/407* (2006.01)
  *G01N 35/00* (2006.01)
  *G01N 35/10* (2006.01)

(52) U.S. Cl.
  CPC ............... *G01N 35/00732* (2013.01); *G01N 2035/00861* (2013.01); *G01N 2035/1032* (2013.01)

(56) References Cited

U.S. PATENT DOCUMENTS

| | | |
|---|---|---|
| 4,855,909 A | 8/1989 | Vincent et al. |
| 5,184,152 A | 2/1993 | French |
| 5,386,287 A | 1/1995 | Berssen et al. |
| 5,397,709 A | 3/1995 | Berndt |
| 5,612,525 A | 3/1997 | Apter et al. |
| 5,688,361 A * | 11/1997 | Itoh .................. B01L 3/5453 156/352 |
| 5,893,016 A | 4/1999 | Landa et al. |
| 6,005,595 A | 12/1999 | Vanwey |
| 6,235,534 B1 | 5/2001 | Brookes et al. |
| 6,570,600 B2 | 5/2003 | Aroneo et al. |
| 6,719,203 B2 | 4/2004 | Hirono et al. |
| 6,771,171 B2 | 8/2004 | Light et al. |
| 7,187,286 B2 | 3/2007 | Morris et al. |
| 7,299,981 B2 | 11/2007 | Hickle et al. |
| 7,445,152 B2 | 11/2008 | Golabek, Jr. et al. |
| 7,604,999 B2 | 10/2009 | Bierre et al. |
| 7,922,073 B2 | 4/2011 | de la Huerga |
| 8,480,953 B2 | 7/2013 | Massaro |
| 8,517,281 B2 | 8/2013 | Rupp |
| 8,584,932 B2 | 11/2013 | Yoshida |
| 8,669,848 B2 | 3/2014 | Morris et al. |
| 8,669,849 B2 | 3/2014 | Morris et al. |
| 8,763,895 B2 | 7/2014 | Colman et al. |
| 8,851,136 B1 | 10/2014 | Drynkin et al. |
| 9,724,948 B2 | 8/2017 | Silbert et al. |
| 2002/0001542 A1 | 1/2002 | Itoh |
| 2003/0089581 A1 | 5/2003 | Thompson |
| 2003/0207456 A1 | 11/2003 | Ostgaard et al. |
| 2004/0091401 A1 | 5/2004 | Golabek, Jr. et al. |
| 2004/0248130 A1 | 12/2004 | Osanai et al. |
| 2006/0013634 A1 | 1/2006 | Harada et al. |
| 2006/0091669 A1 | 5/2006 | Wilkinson |
| 2007/0204497 A1 | 9/2007 | de la Huerga |
| 2008/0121688 A1 | 5/2008 | Harrop |
| 2008/0291435 A1 | 11/2008 | Murakami |
| 2008/0292506 A1 | 11/2008 | Itoh |
| 2009/0308186 A1 | 12/2009 | Bara et al. |
| 2010/0126286 A1 | 5/2010 | Self et al. |
| 2011/0001769 A1 | 1/2011 | Nagai |
| 2013/0065797 A1 | 3/2013 | Silbert et al. |
| 2013/0270339 A1 | 10/2013 | Westra et al. |
| 2014/0374016 A1 | 12/2014 | Schach |

FOREIGN PATENT DOCUMENTS

| | | |
|---|---|---|
| CN | 103988064 A | 8/2014 |
| EP | 0 317 325 A2 | 5/1989 |
| EP | 0317325 A3 | 5/1990 |
| EP | 0 619 493 A1 | 10/1994 |
| EP | 1 972 942 A1 | 9/2008 |
| EP | 2 439 143 A1 | 4/2012 |
| JP | 01-156667 A | 6/1989 |
| JP | 1-267143 A | 10/1989 |
| JP | 01-287464 A | 11/1989 |
| JP | H07 120474 | 5/1995 |
| JP | 10-77017 A | 3/1998 |
| JP | H11/221903 A | 8/1999 |
| JP | 11-264830 A | 9/1999 |
| JP | 11-337559 A | 12/1999 |
| JP | 2000-088861 A | 3/2000 |
| JP | 2000/247315 A | 9/2000 |
| JP | 2003-102476 A | 4/2003 |
| JP | 2007-147658 A | 6/2007 |
| JP | 2009-121837 A | 6/2009 |
| JP | 2010-127681 A | 6/2010 |
| JP | 2014/138994 A | 7/2014 |
| WO | 02/095675 A1 | 11/2002 |
| WO | 2006/050319 A2 | 5/2006 |
| WO | 2006/121728 A2 | 11/2006 |
| WO | 2008/028028 A2 | 3/2008 |
| WO | 2009/083943 A1 | 7/2009 |
| WO | 2010/134966 A1 | 11/2010 |
| WO | 2011/000798 A1 | 1/2011 |
| WO | 2011-091245 A1 | 7/2011 |

OTHER PUBLICATIONS

SIPO, First Office Action, Chinese Patent Application No. 201580070010.5, dated Mar. 9, 2018.
SIPO, Search Report, Chinese Patent Application No. 201580070010.5, dated Mar. 9, 2018.
PCT Invitation to Pay Additional Fees, International Application No. PCT/US2015/056763, dated Feb. 5, 2016.
PCT International Preliminary Report on Patentability, International Application No. PCT/US2015/056763, dated May 4, 2017.
PCT International Search Report, International Application No. PCT/US2015/056763, dated May 9, 2016.
PCT Written Opinion, International Application No. PCT/US2015/056763, dated May 9, 2016.
USPTO Non-Final Rejection, U.S. Appl. No. 14/919,467, dated Nov. 4, 2016.
USPTO Notice of Allowance, U.S. Appl. No. 14/919,467, dated Mar. 22, 2017.
USPTO Corrected Notice of Allowability, U.S. Appl. No. 14/919,467, dated Jul. 13, 2017.
USPTO Non-Final Rejection, U.S. Appl. No. 14/858,436, dated Oct. 28, 2016.
USPTO Final Rejection, US. Appl. No. 14/858,436, dated Jun. 29, 2017.
USPTO Advisory Action, U.S. Appl. No. 14/858,436, dated Sep. 6, 2017.
CIPO Examination Report, Canadian Application No. 2,964,930, dated Sep. 1, 2017.
CIPO Examination Report, Canadian Application No. 2,977,889, dated Jan. 24, 2018.
JPO Office Action, Japanese Application No. 2017-008314, dated Nov. 27, 2017.
JPO Office Action, Japanese Application No. 2017-008313, dated Nov. 27, 2017.
EPO Extended European Search Report, European Application No. 17170265.7, dated Sep. 6, 2017.
CIPO Notice of Allowance, Canadian Application No. 2,964,930, dated Dec. 21, 2017.
JPO Office Action, Japanese Patent Application No. 2017-521565, dated Jun. 27, 2019.
USPTO Notice of Allowance, U.S. Appl. No. 15/971,660, dated Aug. 2, 2019.

* cited by examiner

METHOD AND APPARATUS FOR PRINTING ON AN OBJECT HAVING A CURVED SURFACE

CROSS-REFERENCE TO RELATED APPLICATION

This application claims the benefit under 35 U.S.C. §§ 120, 121 of the filing date of non-provisional patent application Ser. No. 14/919,467 filed Oct. 21, 2015, now U.S. Pat. No. 9,724,948, which claims the benefit under 35 U.S.C. § 119(e) of the filing date of provisional patent application Ser. No. 62/066,468 filed Oct. 21, 2014, the disclosure which is incorporated herein by reference.

FIELD OF THE DISCLOSURE

This disclosure relates to systems and methods for printing information onto curved surfaces that may have dimensional and/or surface irregularities and/or other anomalies, such as injection-molded plastic test tubes.

BACKGROUND

In certain processes, such as, for example, manufacturing or analytical or diagnostic testing processes, it is often necessary, or at least desirable, to identify an article or item undergoing a process and to monitor the location and status of the article throughout the process. This may especially be the case in automated processes that involve multiple steps performed at multiple locations throughout a system, e.g., an assembly line, a fabrication line, diagnostic instrument, or a laboratory. It is also not uncommon that one or more process steps performed may need to be varied for different articles and thus it becomes necessary to not only track the location of the article but to also communicate to different processing modules within the system the particular step or steps to be performed on that particular article.

For example, in analytical or diagnostic chemical or biological tests, such as molecular diagnostic assays, the nature and/or source of a sample to be tested and/or the specific test protocols to be followed in testing each sample must be monitored and tracked throughout the testing process.

In the case of chemical or biological testing, identification of the sample, e.g., the nature and/or source, including clinical, industrial, environmental, and food sources, of the sample, may be implemented by means of a label bearing identifying information placed on a container that holds a volume of sample from which aliquots of the sample are taken for testing and/or a container within which one or more chemical or biological reactions are to take place. Such identifying information may include human-readable (e.g., alphanumeric) information to be read by persons handling and processing the container. For containers that are to be placed into a diagnostic instrument for subsequent automated processing, it is may be advantageous to provide machine-readable information on the container. Such machine-readable information may include a barcode (linear or 2-dimensional) that can be read by scanners within the instrument or laboratory and wherein the unique number sequence that is encoded in the barcode is correlated with an information record, e.g., via a relational database, relating to the container and/or its contents. For biological samples, the information may comprise the nature of the sample material, e.g., blood, urine, sputum, saliva, pus, mucous, cerebrospinal fluid, fecal matter, etc., the source of the sample material, e.g., a patient name, and the test or tests to be performed on the sample material. As the container is being processed within an instrument and/or a laboratory, data from the container barcode is read by a barcode scanner, or reader, and data encompassing (or otherwise containing) information derived from the barcode data, as well as, optionally, data encompassing other information associated with the barcode information, can be written to or retrieved from memory to be readable by a processing instrument. During or after the process, additional information may be added to the record, including, for example, tests or processes to be performed, test results and error codes, available volume in container, instrument IDs, and/or other tracking information, such as a complete history of all instruments on which the container has been processed.

In one embodiment, the data of the container barcode constitutes an address in a database, e.g., a relational database, within which information regarding the contents of the container is stored. For example, if the container holds a sample, the information contained in the barcode data may be used to look up in a database information regarding the sample, such as the nature of the sample (blood, urine, etc.), the identity of the patient, or other source, from which the sample was obtained, the date the sample was obtained, the test(s) or assay(s) to be performed on the sample, etc., or a combination thereof. On the other hand, if the container contains reagent or some other process material, information contained in the barcode data may be used to look up in a database information regarding the type of process material, manufacturer, lot number, expiration date, storage conditions, history of use, volume, etc.

In some cases, empty containers may be provided that are pre-labeled with unique identifying information, such as a barcode, and that unique identifying information is later associated with information relating to the sample that is placed into the container. The association may be made by scanning the pre-applied barcode and associating the information encoded in the barcode with information relating to the sample material added to—or to be added to—the container. In other instances, before or after sample material is placed in an unlabled container, a label may be printed for that container bearing a unique identifier that has been associated with information relating to the sample material placed in the container. Such labels are typically printed onto adhesive-backed paper, and a technician or other laboratory personnel will peel the label from its backing and place it on the container. Care must be taken to ensure that the label is placed on the container at the correct orientation to enable the label code to be read by a scanner and to ensure that the printed information on the label is not smudged or otherwise distorted, e.g., by a wrinkle in the label, in a manner that will interfere with subsequent reading of the label. Needless to say, care must also be taken to ensure that each label is placed on the correct container containing the sample material associated with the unique identifier on the label.

To avoid the need for laboratory personnel to peel labels from the backing and to reduce the possibility of misapplied or unreadable labels, it may be desirable to print the unique identifying information directly onto an initially-blank label placed on the container. In the case of machine-readable information, such as barcodes, the printed information must be sufficiently precise to enable the information to be accurately read by barcode scanners. A poor quality print—e.g., faint, blurred, or fuzzy lines and edges or characters running together—will impair the ability of a scanner to accurately read the information printed on the label. Typically, thermal printers, which produce an image by selectively heating coated thermo chromic paper, or thermal paper, when the paper is passed over a thermal print head, are best suited for such applications because they are capable of clean, precise printing. In addition, in chemical or biological laboratory applications, as well as in specialized, e.g., clean room, fabrication, or assembly processes, thermal printers are advantageous over other printers that use inks or carbon-based toner powders because such inks or powders can be a source of contamination in the process. In addition, the lack of consumables, such as ink, ribbons, toner, etc. associated with other printers, improves the reliability of thermal printers over such other printers and makes thermal printers easier to use and maintain as the necessary servicing of such non-existent consumables is avoided.

Precise printing with a thermal printer requires sufficient physical and thermal contact between the thermal print head and the thermal paper throughout the printing process, which involves relative movement between the print head and the paper. Where the surface to be printed on is curved and/or is subject to imperfections or other surface anomalies, such as warpage, bumps, rippling, bowing, etc., maintaining such contact can be extremely difficult, especially where the surface to be printed on is relatively hard and rigid. In conventional thermal printers, such as point of sale printers, the print head contacts the thermal paper, as the paper moves over a roller, that is typically made from an elastomeric material, such as rubber. As the surface of such a roller will be compliant, the print head can press the thermal paper against the roller surface, and the compliance of the roller surface facilitates uniform contact between the print head and the paper. In addition, rollers for such printers can be made with tight tolerances so as to minimize dimensional variations and surface anomalies. On the other hand, containers used in certain chemical or biological tests may comprise generally cylindrical tubes made from an injection-molded thermoplastic. Such tubes may be of a relatively small diameter, e.g., 0.5 inches, and thus the side wall of such tubes have a high degree of curvature. Moreover, by the very nature of the molding process when articles of this type are mass-produced, such tubes may have dimensional tolerances that lead to concave and/or convex side wall portions that can create high points or low points or other surface imperfections and anomalies that inhibit good, uniform contact between the thermal print head and the side wall of the tube.

Thus, a need exists for a device configured to print—especially thermal print—information onto a curved surface that may include dimensional inconsistencies and other inconsistent and unpredictable surface variations and anomalies.

SUMMARY OF THE DISCLOSURE

This disclosure describes an apparatus for printing on a curved surface of an article. The apparatus comprises an expandable printing mechanism including a print head and is configured and controlled to be selectively (1) expanded to an open configuration for enabling an article having a curved surface on which information is to be printed to be received within or removed from the apparatus, and (2) contracted to a printing configuration placing the curved surface of an article received within the apparatus in operative position with respect to the print head and maintaining the curved surface in an operative printing position with respect to the print head during relative movement of the curved surface with respect to the print head. The apparatus also includes an article moving assembly configured and controlled to: (1) grasp an article received within the apparatus and effect relative movement between the curved surface of the article and the print head when the expandable printing mechanism is in the printing configuration, and (2) release the article when the expandable printing mechanism is in the open configuration, thereby allowing the article to be removed from the apparatus.

According to further aspects of the disclosure, the apparatus further comprises a housing at least partially enclosing the expandable printing mechanism and the article moving assembly.

According to further aspects of the disclosure, the apparatus further includes an opening formed in the housing through which an article having a curved surface on which information is to be printed can be received within or removed from the apparatus.

According to further aspects of the disclosure, the expandable printing mechanism comprises a first support element having one or more contact element(s) operatively supported thereon and a second support element supporting the print head thereon. The first support element and the second support element are configured for relative movement with respect to each other between the open configuration of the expandable printing mechanism and the printing configuration of the expandable printing mechanism. The contact element(s) are configured to contact an article received within the apparatus to hold the curved surface in the operative position with respect to the print head when the expandable printing mechanism is in the printing configuration.

According to further aspects of the disclosure, the one or more contact elements comprise a first roller and a second roller rotatably mounted to the first support element.

According to further aspects of the disclosure, the apparatus further comprises an expander mechanism configured to effect relative movement of the first and second support elements between the open configuration and the printing configuration.

According to further aspects of the disclosure, the first roller is axially elongated, and the second roller comprises, extending axially along the length of the roller, a first head portion that is of a first diameter, an extension portion that is of a second diameter that is less than the first diameter, and a second head portion that is of a third diameter that is greater than the second diameter.

According to further aspects of the disclosure, the third diameter is equal to the first diameter.

According to further aspects of the disclosure, the first roller is cylindrical.

According to further aspects of the disclosure, the first roller has a varying diameter that increases from each axial end of the roller to the axial middle of the roller.

According to further aspects of the disclosure, the first support element comprises a roller bracket having an upper flange, a lower flange, and a web extending between the upper and lower flanges, and wherein the first roller and the second roller are rotatably mounted between the first and second flanges. The second support element comprises a print head bracket having an upper flange, a lower flange, and a web extending between the upper and lower flanges. The roller bracket and the print head bracket are oriented such that the webs of the roller bracket and the print head bracket are generally parallel to one another; and the roller bracket and the print head bracket are pivotably mounted to a common pivot shaft so that the roller bracket and the print head bracket are pivotable with respect to each other in a hinge-wise fashion about the pivot shaft between the open configuration and the printing configuration.

According to further aspects of the disclosure, the first and second support elements are pivotably mounted to a common pivot shaft so that the first and second support elements are pivotable with respect to each other in a hinge-wise fashion about the pivot shaft between the open configuration and the printing configuration. The expander mechanism comprises a driven shaft located between the first and second support elements, the driven shaft being generally parallel to the pivot shaft, and a cam element attached to and rotatable with the driven shaft and in contact with both the first and second support elements. The cam element has a varying dimension so that in one orientation of the cam element, portions of the cam element contacting the first and second support elements hold the first and second support elements apart by a first distance corresponding to the open configuration of the expandable printing mechanism and in another orientation of the cam element, portions of the cam element contacting the first and second support elements hold the first and second support elements apart by a second distance corresponding to the printing configuration of the expandable printing mechanism.

According to further aspects of the disclosure, the cam element comprises a cam disc fixed to the driven shaft and coaxial therewith. The cam disc has a variable radius so that in a first rotational position of the cam disc, portions of the cam disc having a first radius are in contact with the first and second support elements and holding the first and second support elements apart by the first distance corresponding to the open configuration, and in a second rotational position of the cam disc, portions of the cam disc having a second radius that is smaller than the first radius are in contact with the first and second support elements and holding the first and second support elements apart by the second distance corresponding to the printing configuration.

According to further aspects of the disclosure, the expander mechanism further comprises a spring extending between the first and the second support elements and configured to bias the first and the second support elements into contact with the cam element.

According to further aspects of the disclosure, each of the first and second support elements further includes a roller bearing mounted thereon, wherein the cam element contacts the roller bearing of each of the first and second support elements.

According to further aspects of the disclosure, the apparatus further comprises a drive mechanism comprising a pulley wheel coaxially mounted to the driven shaft, a motor having an output shaft and a drive wheel, and a drive belt coupling the drive wheel to the pulley wheel.

According to further aspects of the disclosure, the expander mechanism further comprises a rotational position sensor configured to detect a rotational position of the driven shaft and cam element.

According to further aspects of the disclosure, the rotational position sensor comprises an index wheel coaxially coupled to the driven shaft and having one or more detectable features formed therein or attached thereto at specified rotational positions and an optical sensor configured to detect the one or more detectable features as the driven shaft and the index wheel rotate with respect to the optical sensor.

According to further aspects of the disclosure, the apparatus further comprises a hand wheel mounted to the driven shaft and configured to enable manual rotation of the driven shaft and the cam element.

According to further aspects of the disclosure, the second support element comprises a print head platen on which the print head is mounted.

According to further aspects of the disclosure, the print head platen is configured and mounted so that its position on the second support element can be laterally adjusted.

According to further aspects of the disclosure, the apparatus further comprises a platen shaft mounted to the second support element, wherein the platen shaft extends through a portion of the print head platen, so as to permit lateral movement of the print head platen along the platen shaft.

According to further aspects of the disclosure, the apparatus further comprises a platen adjustment lever pivotably mounted to the second support element and including a contact point in contact with a portion of the print head platen and configured such that pivoting movement of the platen adjustment lever effects lateral movement of the print head platen along the platen shaft.

According to further aspects of the disclosure, the platen adjustment lever includes a protuberance that is configured to be inserted into one of a plurality of holes formed in the second support element to secure the platen adjustment lever at a selected rotational position.

According to further aspects of the disclosure, the apparatus further comprises a timing mark sensor configured to detect a timing mark on the curved surface.

According to further aspects of the disclosure, the article moving assembly comprises a carousel configured for powered rotation and moveable gripper elements configured to be movable between a release position permitting an article to be placed within or removed from the apparatus and a gripping position for securing the article with respect to the carousel so that the article rotates with the carousel.

According to further aspects of the disclosure, each gripper element comprises a gripper assembly that is coupled to the carousel and is configured so that rotation of the carousel in a first direction causes all the gripper assemblies to move radially inwardly to the gripping position with respect to an article placed between the gripper assemblies and rotation of the carousel in a second direction opposite the first direction causes all of the gripper assemblies to move radially outwardly to the release position with respect to the article.

According to further aspects of the disclosure, the apparatus comprises three gripper assemblies.

According to further aspects of the disclosure, the carousel comprises an upper disc and a lower disc, coaxially arranged with the upper disc, the upper and lower discs being rotatable relative to one another.

According to further aspects of the disclosure, each moveable gripper element comprises a pivoting gripper assembly comprising a pivot arm disposed between the upper disc and the lower disc of the carousel and pivotably attached to the upper disc, a knurled wheel rotatably mounted above the upper disc on a shaft extending from the pivot arm through the upper disc, and a guide pin extending from the pivot arm into an associated guide slot formed in the lower disc.

According to further aspects of the disclosure, a first end of each guide slot formed in the lower disc is closer to a radial center of the lower disc than a second end of the guide slot.

According to further aspects of the disclosure, the article moving assembly further comprises a drive mechanism comprising a motor having an output shaft and a drive wheel and a drive belt coupling the drive wheel to the carousel.

According to further aspects of the disclosure, the carousel includes peripheral gear teeth for engagement by the drive belt.

According to further aspects of the disclosure, the print head comprises a thermal print head.

This disclosure also describes a method for printing on a curved surface of an article with a printing module configured to receive an article having a curved surface, secure the article so that the curved surface is in an operative position with respect to a print head of the printing module, effect relative movement between the curved surface and the print head while the print head is activated and while maintaining the curved surface in the operative position with respect to the print head, thereby printing information onto the curved surface, and then release the article so that it may be removed from the printing module. The method comprises the steps of confirming that the printing module is in an open configuration for enabling the article having a curved surface to be placed within the module, inserting the article into the printing module, moving the curved surface with respect to the print head, detecting a timing mark on the curved surface, configuring the printing module into a printing configuration whereby the curved surface of the article placed within the printing module is in an operative position with respect to the print head of the printing module, activating the print head, imparting an image onto the curved surface by moving the curved surface with respect to the print head while the print head is activated and maintaining the curved surface in the operative position with respect to the print head for a specified amount of relative movement, after imparting the image onto the curved surface, deactivating the print head and terminating relative movement between the curved surface and the print head, configuring the printing module into the open configuration whereby the article can be removed from the printing module, and removing the article from the printing module According to further aspects of the disclosure, the timing mark is detected with a timing mark sensor configured to detect a change in the reflectivity of a portion of the curved surface.

According to further aspects of the disclosure, the timing mark sensor generates a waveform based on the reflectivity of a portion of the curved surface, and wherein the timing mark is sensed by detecting a change in the waveform the exceeds a predefined threshold.

According to further aspects of the disclosure, the method further includes the step of imparting a timing mark modifier onto the curved surface to indicate that the article has been printed on.

According to further aspects of the disclosure, the method further comprises the step of, after detecting the timing mark, determining one or more dimensions of the timing mark and comparing the determined one or more dimensions of the timing mark to at least one predetermined threshold dimension.

According to further aspects of the disclosure, the method further comprises the step of, after configuring the printing module into the open configuration, determining whether each determined dimension of the image is within a predefined range of an expected dimension of the image.

This disclosure also describes a method for printing on a curved surface of an article with a printing module. The method comprises the steps of configuring the printing module in an open configuration to receive an article having a curved surface on which information is to be printed, placing an article into the printing module, configuring the printing module in a printing configuration and securing the article so that the curved surface is in an operative position with respect to a print head of the printing module, activating the print head and effecting relative movement between the curved surface and the print head while the print head is activated and while maintaining the curved surface in the operative position with respect to the print head, after printing an image onto the curved surface, configuring the printing module into an open configuration enabling the article to be removed from the printing module, and removing the article from the printing module.

The disclosure also describes a system for processing a sample. The system includes a sample transfer apparatus, a code reading device, a controller, and a printing module. The sample transfer apparatus is configured to remove an amount of sample material from a first container and dispense at least a portion of the removed sample material in a second container. The code reading device is configured to read a first machine-readable graphic code on a surface of the first container, and the first machine-readable graphic code has encoded therein information relating to the sample material contained in the first container. The controller is configured to generate a second machine-readable graphic code having encoded therein information relating to the information encoded in the first machine-readable graphic code. The printing module is configured and controlled to print the second machine-readable graphic code on a curved surface of the second container. The printing module comprises an expandable printing mechanism including a print head. The expandable printing mechanism is configured and controlled to be selectively (1) expanded to an open configuration for enabling the second container to be received within or removed from the printing module, and (2) contracted to a printing configuration placing the curved surface of the second container in an operative printing position with respect to the print head and maintaining the curved surface in the operative printing position with respect to the print head during relative movement of the curved surface with respect to the print head. The printing module further comprises a moving assembly configured and controlled to (1) grasp the received second container and effect relative movement between the curved surface of the second container and the print head when the expandable printing mechanism is in the printing configuration, and (2) release the article when the expandable printing mechanism is in the open configuration, thereby allowing the article to be removed from the printing module.

According to further aspects of the disclosure, the sample transfer apparatus comprises a pipettor carried on a robotic arm.

According to further aspects of the disclosure, the system further comprises a pick-and-place mechanism configured and controlled to selectively move either or both of the first and second containers from a first location within the system to a second location within the system.

According to further aspects of the disclosure, the pick-and-place mechanism comprises a container gripper carried on a robotic arm.

According to further aspects of the disclosure, the printing module further comprises a housing at least partially enclosing the expandable printing mechanism and the moving assembly.

According to further aspects of the disclosure, the system further includes an opening formed in the housing through which the second container can be moved into or out of the housing of the printing module.

According to further aspects of the disclosure, the expandable printing mechanism comprises a first support element having one or more contact element(s) operatively supported thereon and a second support element supporting the print head thereon. The first support element and the second support element are configured for relative movement with respect to each other between the open configuration of the expandable printing mechanism and the printing configuration of the expandable printing mechanism. The contact element(s) are configured to contact the second container received within the printing module to hold the curved surface in the operative position with respect to the print head when the expandable printing mechanism is in the printing configuration.

According to further aspects of the disclosure, the one or more contact elements comprise a first roller and a second roller rotatably mounted to the first support element.

According to further aspects of the disclosure, the expandable printing mechanism further comprises an expander mechanism configured to effect relative movement of the first and second support elements between the open configuration and the printing configuration.

According to further aspects of the disclosure, the first roller is axially elongated, and the second roller comprises, extending axially along the length of the roller, a first head portion that is of a first diameter, an extension portion that is of a second diameter that is less than the first diameter, and a second head portion that is of a third diameter that is greater than the second diameter.

According to further aspects of the disclosure, the second roller is configured so that the third diameter is equal to the first diameter.

According to further aspects of the disclosure, the first roller is cylindrical.

According to further aspects of the disclosure, the first roller has a varying diameter that increases from each axial end of the roller to the axial middle of the roller.

According to further aspects of the disclosure, the first support element comprises a roller bracket having an upper flange, a lower flange, and a web extending between the upper and lower flanges, and wherein the first roller and the second roller are rotatably mounted between the first and second flanges. The second support element comprises a print head bracket having an upper flange, a lower flange, and a web extending between the upper and lower flanges, the roller bracket and the print head bracket being oriented such that the webs of the roller bracket and the print head bracket are generally parallel to one another. The roller bracket module configured to print a label on a curved surface of an article includes an expandable printing mechanism configured to be expanded to an open configuration for receiving the article or contracted to a aft between the open configuration and the printing configuration According to further aspects of the disclosure, the first and second support elements are pivotably mounted to a common pivot shaft so that the first and second support elements are pivotable with respect to each other in a hinge-wise fashion about the pivot shaft between the open configuration and the printing configuration. The expander mechanism comprises a driven shaft that is generally parallel to the pivot shaft and is located between the first and second support elements and a cam element attached to and rotatable with the driven shaft and in contact with both the first and second support elements. The cam element has a varying dimension so that in one orientation of the cam element, portions of the cam element contacting the first and second support elements hold the first and second support elements apart by a first distance corresponding to the open configuration of the expandable printing mechanism and in another orientation of the cam element, portions of the cam element contacting the first and second support elements hold the first and second support elements apart by a second distance corresponding to the printing configuration of the expandable printing mechanism.

According to further aspects of the disclosure, the cam element comprises a cam disc fixed to the driven shaft and coaxial therewith. The cam disc has a variable radius so that in a first rotational position of the cam disc, portions of the cam disc having a first radius are in contact with the first and second support elements and holding the first and second support elements apart by the first distance corresponding to the open configuration, and in a second rotational position of the cam disc, portions of the cam disc having a second radius that is smaller than the first radius are in contact with the first and second support elements and holding the first and second support elements apart by the second distance corresponding to the printing configuration.

According to further aspects of the disclosure, the expander mechanism further comprises a spring extending between the first and second support elements and configured to bias the first and second support elements into contact with the cam element.

According to further aspects of the disclosure, each of the first and second support elements further includes a roller bearing mounted thereon, and the cam element contacts the roller bearing of each of the first and second support elements.

According to further aspects of the disclosure, the system further comprises a drive mechanism comprising a pulley wheel coaxially mounted to the driven shaft, a motor having an output shaft and a drive wheel, and a drive belt coupling the drive wheel to the pulley wheel.

According to further aspects of the disclosure, the expander mechanism further comprises a rotational position sensor configured to detect a rotational position of the driven shaft and cam element.

According to further aspects of the disclosure, the rotational position sensor comprises an index wheel coaxially coupled to the driven shaft and having one or more detectable features formed therein or attached thereto at specified rotational positions and an optical sensor configured to detect the one or more detectable features as the driven shaft and the index wheel rotate with respect to the optical sensor.

According to further aspects of the disclosure, the system further comprises a hand wheel mounted to the driven shaft and configured to enable manual rotation of the driven shaft and the cam element.

According to further aspects of the disclosure, the second support element comprises a print head platen on which the print head is mounted.

According to further aspects of the disclosure, the print head platen is configured and mounted so that its position on the second support element can be laterally adjusted.

According to further aspects of the disclosure, the system further comprises a platen shaft mounted to the second support element, and the platen shaft extends through a portion of the print head platen, so as to permit lateral movement of the print head platen along the platen shaft.

According to further aspects of the disclosure, the system further comprises a platen adjustment lever pivotably mounted to the second support element and including a contact point in contact with a portion of the print head platen and configured such that pivoting movement the platen adjustment lever effects lateral movement of the print head platen along the platen shaft.

According to further aspects of the disclosure, the platen adjustment lever includes a protuberance that is configured to be inserted into one of a plurality of holes formed in the second support element to secure the platen adjustment lever at a selected rotational position.

According to further aspects of the disclosure, the system further comprises a timing mark sensor configured to detect a timing mark on the curved surface.

According to further aspects of the disclosure, the moving assembly comprises a carousel configured for powered rotation and moveable gripper elements configured to be movable between a release position permitting an article to be placed within or removed from the apparatus and a gripping position for securing the second container with respect to the carousel so that the article rotates with the carousel.

According to further aspects of the disclosure, each gripper element comprises a gripper assembly that is coupled to the carousel and is configured so that rotation of the carousel in a first direction causes all the gripper assemblies to move radially inwardly to the gripping position with respect to the second container placed between the gripper assemblies and rotation of the carousel in a second direction opposite the first direction causes all the gripper assemblies to move radially outwardly to the release position with respect to the second container.

According to further aspects of the disclosure, the system comprises three gripper assemblies.

According to further aspects of the disclosure, the carousel comprises an upper disc and a lower disc coaxially arranged with the upper disc, and the upper and lower discs are rotatable relative to one another.

According to further aspects of the disclosure, each moveable gripper element comprises a pivoting gripper assembly comprising a pivot arm disposed between the upper disc and the lower disc of the carousel and pivotably attached to the upper disc, a knurled wheel rotatably mounted above the upper disc on a shaft extending from the pivot arm through the upper disc, and a guide pin extending from the pivot arm into an associated guide slot formed in the lower disc.

According to further aspects of the disclosure, a first end of each guide slot formed in the lower disc is closer to a radial center of the lower disc than a second end of the guide slot.

According to further aspects of the disclosure, the moving assembly further comprises a drive mechanism comprising a motor having an output shaft and a drive wheel and a drive belt coupling the drive wheel to the carousel.

According to further aspects of the disclosure, the carousel includes peripheral gear teach for engagement by the drive belt.

According to further aspects of the disclosure, the print head comprises a thermal print head.

Further aspects of the disclosure are embodied in a method for processing a sample material within a sample processing system. The method comprises, with a code reading device, automatically reading first machine-readable indicia on a surface of a first sample container containing a volume of a sample material. Information relating to the sample material contained in the first sample container is encoded in the first machine-readable indicia. Second machine-readable indicia are automatically applied on a curved surface of a second sample container. The second machine-readable indicia applied to the curved surface includes indicia relating to the first machine-readable indicia read from the first sample container, and automatically applying the second machine-readable indicia on the curved surface comprises printing the second machine-readable indicia directly onto the curved surface with a printing module. The printing module comprises a print head, one or more contact elements configured to hold the second sample container with respect to the print head so as to hold the curved surface in an operative position with respect to the print head, and a moving assembly configured to hold the second sample container and rotate the second sample container so as to move the curved surface with respect to the print head. With an automated substance transfer device, an amount of sample material is automatically transferred from the first sample container to the second sample container.

According to further aspects, the method further comprises the step of moving a second sample container from an input rack to the printing module with a robotic pick-and-place mechanism prior to applying second machine-readable indicia to the second sample container.

According to further aspects, the method further comprises the step of moving a second sample container from the printing module to a sample processing station with a robotic pick-and-place mechanism after applying second machine-readable indicia to the second sample container and prior to transferring an amount of sample material from the first sample container to the second sample container.

According to further aspects, the method further comprises the step of moving the second sample container from the sample processing station to an output rack with the robotic pick-and-place mechanism after transferring an amount of sample material from the first sample container to the second sample container.

According to further aspects, the first machine-readable indicia comprise a first barcode and the second machine readable indicia comprise a second barcode.

According to further aspects, the first and second barcodes are at least partially identical.

According to further aspects, the second sample container initially includes a blank label and the second machine readable indicia are printed onto the blank label.

According to further aspects, the print head is a thermal print head and the curved surface comprises thermally sensitive print media.

According to further aspects, the information relating to the sample material comprises sample-identifying information.

According to further aspects, the information relating to the sample material comprises sample-identifying information, and the second machine-readable indicia applied onto the curved surface of the second sample container are at least partially identical to the first machine-readable indicia on the first sample container.

According to further aspects, the second machine-readable indicia applied onto the curved surface of the second sample container includes additional machine-readable indicia that are different from the first machine-readable indicia on the first sample container, and information relating to one or more of time, volume, sample type, reagents, test procedures, test results, and errors is encoded in the additional machine-readable indicia.

Further aspects of the disclosure are embodied in a method for controlling a printing process by which a print head prints an image onto predetermined printable area of a label. The method comprises the steps of effecting relative movement between a timing mark sensor and the label, while effecting the relative movement, detecting a position of a timing mark with a timing mark sensor, after detecting the timing mark, effecting relative movement between the print head and the label to position the print head at an image position at a specified distance from the position of the timing mark, activating the print head; and while activating the print head, effecting relative movement between the print head and the label for a specified image distance to print the image onto the printable area.

According to further aspects of the disclosure, the image comprises a barcode.

According to further aspects of the disclosure, the label is disposed on a curved surface of an article, and effecting relative movement between the label and the timing mark sensor and between the label and the print head comprises rotating the article with respect to the timing mark sensor and the print head.

According to further aspects of the disclosure, the timing mark sensor is configured to detect reflectivity of a surface passing before the timing mark sensor, and detecting the timing mark comprises detecting the reflectivity of portions of the label passing by the timing mark sensor, wherein the reflectivity of the timing mark is different from the reflectivity of the remaining portions of the label passing by the timing mark sensor.

According to further aspects of the disclosure, the method further comprises detecting the presence of the label before effecting relative movement between the timing mark sensor and the label.

According to further aspects of the disclosure, the presence of the label is detected by the timing mark sensor based on a change in reflectivity due to the presence of the label that exceeds a predetermined print-surface-present threshold.

According to further aspects of the disclosure, the method further comprises generating a waveform from the output of the timing mark sensor based on the reflectivity of the portion of the label passing by the timing mark sensor, and the timing mark is sensed by detecting a change in the waveform that exceeds a predefined timing mark threshold.

According to further aspects of the disclosure, the method further comprises detecting a first edge of the timing mark based on the change in the waveform falling below a negative timing mark threshold and detecting a second edge of the timing mark based on the change in the waveform rising above a positive timing mark threshold.

According to further aspects of the disclosure, the waveform comprises a plurality of data points sequentially-recorded from the output of the timing mark sensor and detecting a change in the waveform comprises comparing a first waveform value for a current data point with a second waveform value for a data point recorded at a predefined period earlier than the current data point to determine if the first waveform value varies from the second waveform value by more than the predefined timing mark threshold.

According to further aspects of the disclosure, the method further comprises the step of printing a timing mark modifier that is detectable by the timing mark sensor onto the label to indicate that the label has been printed on.

According to further aspects of the disclosure, printing the timing mark modifier comprises printing an image that alters the timing mark in a manner that is detectable by the timing mark sensor.

According to further aspects of the disclosure, printing the timing mark modifier comprises printing an additional, mark distinct from the timing mark.

According to further aspects of the disclosure, effecting relative movement between the print head and the label to position the print head at an image position at a specified distance from the position of the timing mark comprises effecting relative movement between the print head and the label for a first predefined distance to place the print head at a print start position over the timing mark, and printing the timing mark modifier comprises activating the print head and effecting a relative movement between the print head and the label.

According to further aspects of the disclosure, printing the timing mark modifier comprises activating the print head and effecting a relative movement between the print head and the label for a first period, terminating the first period when the timing mark is detected with the timing mark sensor, and activating the print head and effecting a relative movement between the print head and the label for a second period defined by a specified amount of relative movement between the print head and the label.

According to further aspects of the disclosure, effecting relative movement between the print head and the label to position the print head at an image position at a specified distance from the position of the timing mark further comprises effecting relative movement between the print head and the label for a third predefined distance without the print head activated to create a print gap following the timing mark modifier, wherein after relative movement for the third predefined distance, the print head is at the printable area.

According to further aspects of the disclosure, detecting the timing mark comprises locating a leading edge and a trailing edge of the timing mark relative to the direction of relative movement between the timing mark sensor and the label, and effecting relative movement between the print head and the label to position the print head at an image position at a specified distance from the position of the timing mark comprises effecting relative movement between the print head and the label to position the print head at the image position at the specified distance from the position of the trailing edge of the timing mark.

According to further aspects of the disclosure, the method further comprises the step of calibrating the luminance of the timing mark sensor by setting the luminance of the timing mark sensor to a first level that will cause the output of the timing mark sensor to exceed an upper output limit, and periodically changing the luminance of the timing mark sensor while effecting relative movement between the timing mark sensor and the label until the output of the timing mark sensor is between a lower output limit and the upper output limit throughout movement of the sensor relative to the entire label.

According to further aspects of the disclosure, the method further comprises the step of determining the length of the timing mark and comparing the determined length of the timing mark to an expected length of the timing mark.

According to further aspects of the disclosure, the method further comprises completing the steps only if the length of the timing mark is within a predetermined range of the expected length of the timing mark.

According to further aspects of the disclosure, the method further comprises the step of determining the length of the timing mark and comparing the determined length of the timing mark to an expected length. Determining the length of the timing mark comprises computing a first point on the waveform where the change in the waveform falls below the negative timing mark threshold, computing a second point on the waveform where the change in the waveform rises above the negative timing mark threshold, computing a third point on the waveform where the change in the waveform rises above the positive timing mark threshold, computing a fourth point on the waveform where the change in the waveform falls below the positive timing mark threshold, and computing the length of the timing mark as the amount of relative movement between the timing mark sensor and the label between a point bisecting the first and second points and a point bisecting the third and fourth points.

According to further aspects of the disclosure, the method further comprises, after printing the image onto the printable area, effecting relative movement between the timing mark sensor and the label, while effecting the relative movement, detecting a position of the timing mark on the label with the timing mark sensor, determining the amount of relative movement between the timing mark sensor and the label when the timing mark is detected, and comparing the amount of relative movement detected with an expected distance between an end of the image and the timing mark.

According to further aspects of the disclosure, the timing mark is darker than its surroundings so that reflectivity of the timing mark is less than the reflectivity of its surroundings.

According to further aspects of the disclosure, the timing mark is lighter than its surroundings so that reflectivity of the timing mark is greater than the reflectivity of its surroundings.

According to further aspects of the disclosure, printing a timing mark modifier comprises printing an extension to increase the length of the timing mark.

According to further aspects of the disclosure, the timing mark comprises a cut-out in the label.

According to further aspects of the disclosure, the timing mark comprises one or more encoder ticks of a series of encoder ticks.

According to further aspects of the disclosure, the timing mark comprises a physical feature formed on a surface of an article to which the label is affixed.

According to further aspects of the disclosure, the timing mark comprises a 1-D or 2-D barcode.

According to further aspects of the disclosure, the timing mark comprises a 1-D or 2-D barcode, and the printing the timing mark modifier comprises printing a 1-D or 2-D barcode.

According to further aspects of the disclosure, the timing mark comprises a 2-D barcode, and detecting a position of the timing mark comprises identifying with a 2-D barcode reader a position of a known coordinate within the 2D barcode.

According to further aspects of the disclosure, the timing mark comprises a 1-D barcode, and detecting a position of the timing mark comprises identifying a leading edge of the 1D barcode as the first location at which a 1-D barcode reader can read the 1-D barcode.

Further aspects of the disclosure are embodied in a method for controlling a printing process by which a print head prints an image onto a label affixed to a tube positioned adjacent to the print head and adjacent to a sensor configured to detect optical and/or physical features of the label. The method comprises the steps of transmitting a command to the sensor to detect the presence of the label affixed to the tube. The sensor either (1) fails to generate a signal indicating the presence of the label, or (2) generates a signal indicating the presence of the label. If the sensor generates a signal indicating the presence of the label in, then a command is transmitted to the sensor to detect a position of a timing mark on the label, wherein the sensor fails to generate a signal indicating the position of a timing mark on the label. If the sensor fails to generate a signal indicating the presence of the label, or the sensor fails to generate a signal indicating the position of a timing mark on the label, the print head is selectively activated while effecting relative movement between the print head and the label to print multiple alternate images at multiple positions on the label.

Further aspects of the disclosure are embodied in a method for controlling a printing process by which a print head prints an image onto a label affixed to a tube positioned adjacent to the print head and adjacent to a sensor configured to detect optical and/or physical features of the label. A command is transmitted to the sensor to detect the presence of the label affixed to the tube, wherein the sensor fails to generate a signal indicating the presence of the label. Upon failure by the sensor to generate a signal indicating the presence of the tube, then the print head is selectively activated while effecting relative movement between the print head and the label to print multiple alternate images at multiple positions on the label.

Further aspects of the disclosure are embodied in a method for controlling a printing process by which a print head prints an image onto a label affixed to a tube positioned adjacent to the print head and adjacent to a sensor configured to detect optical and/or physical features of the label. The presence of the label affixed to the tube with the sensor is detected. After detecting the label, a command is transmitted to the sensor to detect a position of a timing mark on the label, wherein the sensor fails to generate a signal indicating the position of a timing mark on the label. After failing to generate a signal indicating the position of the timing mark, the print head is selectively activated while effecting relative movement between the print head and the label to print multiple alternate images at multiple positions on the label.

Other features and characteristics of the subject matter of this disclosure, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

The accompanying drawings, which are incorporated herein and form part of the specification, illustrate various embodiments of the subject matter of this disclosure. In the drawings, like reference numbers indicate identical or functionally similar elements.

FIG. 29 is a plan view of a printable label configured to be applied to an article to be printed on and including a pre-printed timing mark for locating an image to be printed on the label and a timing mark modifier for indicating that the label has been previously printed on.

DETAILED DESCRIPTION

Figure 1:
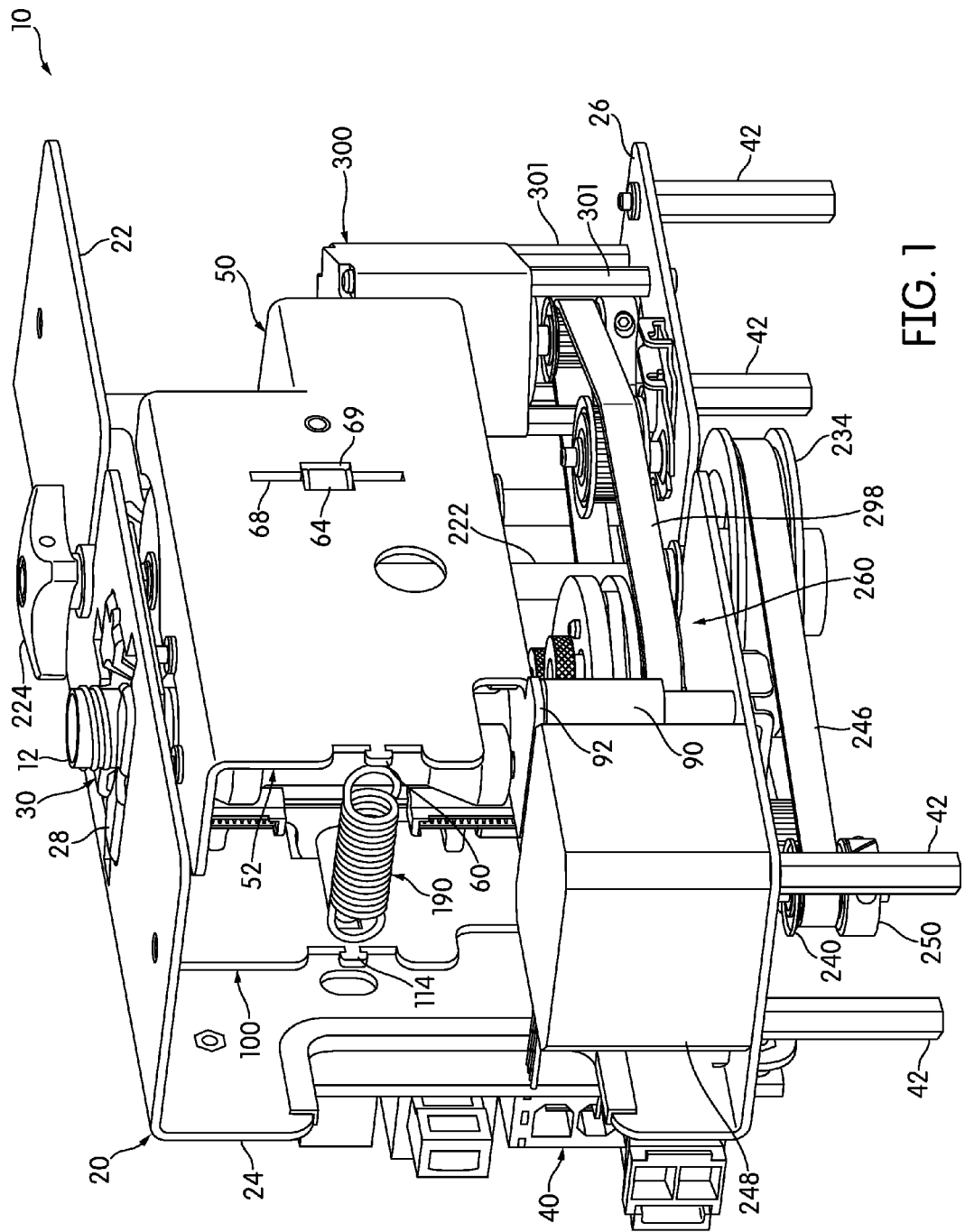
FIG. 1 is a frontal, right-hand partial perspective view of a printing module.

While aspects of the subject matter of the present disclosure may be embodied in a variety of forms, the following description and accompanying drawings are merely intended to disclose some of these forms as specific examples of the subject matter. Accordingly, the subject matter of this disclosure is not intended to be limited to the forms or embodiments so described and illustrated.

Unless defined otherwise, all terms of art, notations and other scientific terms or terminology used herein have the same meaning as is commonly understood by one of ordinary skill in the art to which this disclosure belongs. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted.

All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

As used herein, "a" or "an" means "at least one" or "one or more."

This description may use relative spatial and/or orientation terms in describing the position and/or orientation of one component, apparatus, location, feature, or a portion thereof. Unless specifically stated, or otherwise dictated by the context of the description, such terms, including, without limitation, top, bottom, above, below, under, on top of, upper, lower, left of, right of, in front of, behind, next to, adjacent, between, horizontal, vertical, diagonal, longitudinal, transverse, etc., are used for convenience in referring to such component, apparatus, location, feature, or a portion thereof in the drawings and are not intended to be limiting.

Printing Module

Figure 2:
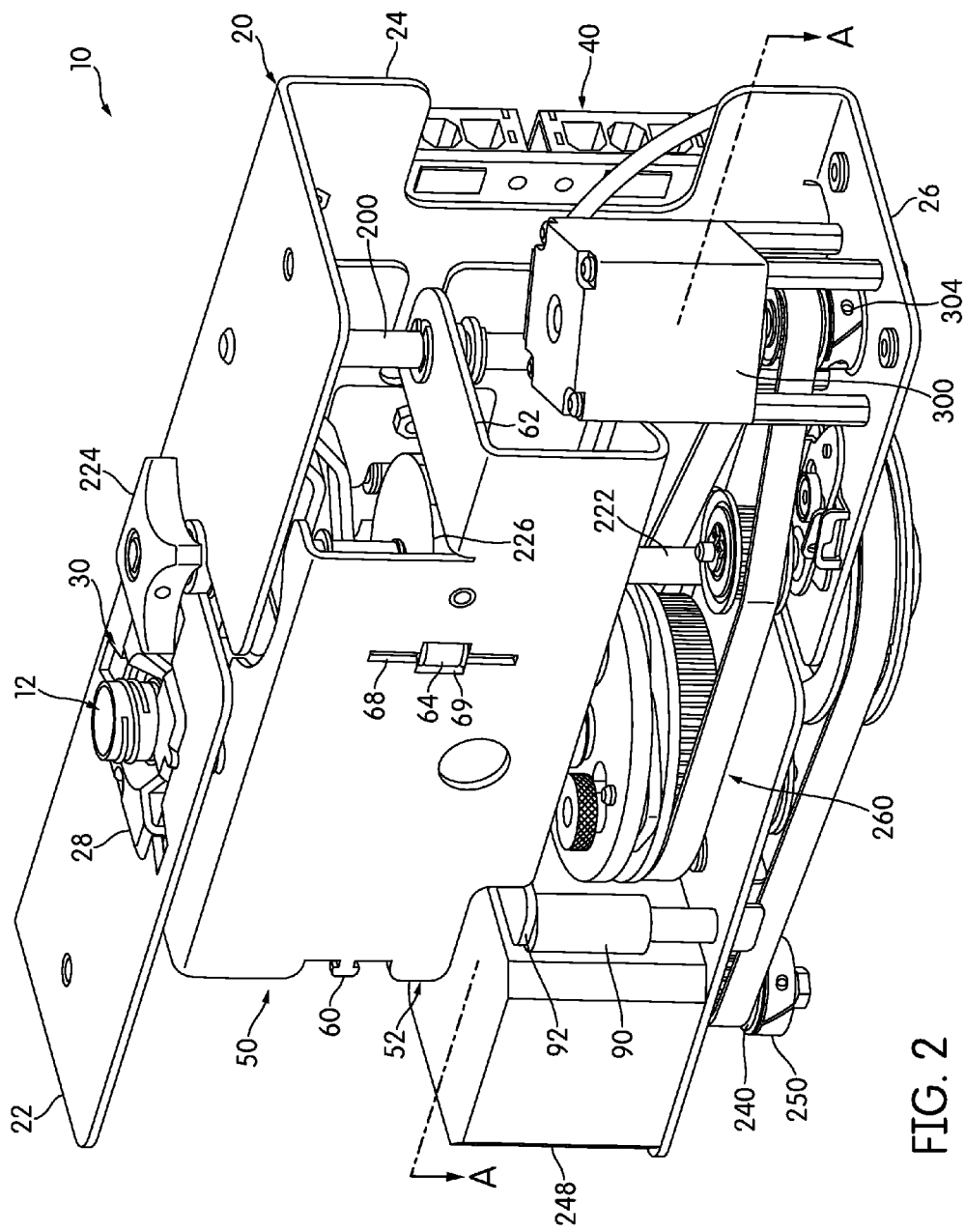
FIG. 2 is a rear, right-hand partial perspective view of the printing module.

A printing module according to the present disclosure is generally indicated by reference number 10 in FIGS. 1 and 2. According to one aspect of the disclosure, the printing module 10 is configured to receive an article having a curved surface on which information is to be printed, such as a tubular container 12, secure the article so that the curved surface is in an operative position with respect to a print head of the printing module, effect relative movement between the curved surface and the print head while the print head is activated and while maintaining the curved surface in the operative position with respect to the print head, thereby printing information onto the curved surface, and then release the article so that it may be removed from the printing module.

In the context of this description, the term "print head" comprises that component or portion of a printing mechanism that imparts an image onto a surface, and the surface to be printed on is "in an operative position with respect to the print head," or is "operatively engaged with the print head," when the print head and the surface are relatively positioned and oriented so that the printing mechanism can impart an accurate image onto an intended location on the surface. In one embodiment, the print head comprises a thermal print head having thermal elements that are placed in contact or near contact to a surface comprising a thermal print medium, such as thermal paper, and are selectively heated during relative movement between the thermal print head and the surface to cause selected portions of the surface to darken in a predetermined pattern, thereby imparting an image to the surface.

The article having a curved surface may comprise a tubular container, such as container 12, e.g., a "test tube", having a tubular, e.g., generally cylindrical, shape and on which is placed a label on the external curved surface thereof onto which information is to be printed. In one embodiment, the curved surface to be printed on may comprise a label formed from, for example, thermal paper media and secured to the external surface of the container 12 by adhesive or the like.

Exemplary tubular containers are described below.

In an exemplary embodiment of the printing module 10, as show in FIGS. 1 and 2, the printing module 10 includes an expandable printing mechanism 50 and an article moving assembly 260. The expandable printing mechanism 50 includes a print head and is configured and controlled to be selectively expanded to an open configuration for enabling the article to be received within or removed from the printing module or contracted to a closed, or printing, configuration placing the curved surface of the article in operative position with respect to the print head and maintaining the curved surface in the operative printing position with respect to the print head during relative movement of the curved surface with respect to the print head. The article moving assembly 260 is configured and controlled to grasp or otherwise operatively engage and hold the article and effect relative movement between the curved surface and the print head of the expandable printing mechanism 50 when the expandable printing mechanism 50 is in the printing configuration and to release the article when the expandable printing mechanism 50 is in the open configuration, thereby allowing the article to be removed from the printing module 10.

In the illustrated embodiment, the article moving assembly 260 comprises a container rotation assembly configured to grasp a container, e.g., a tubular container such as container 12, that is operatively engaged with the print head of the expandable printing mechanism 50, rotate the container while the print head is activated to impart an image onto a curved surface of the container, and to release the container after the printing is complete and the expandable printing mechanism is in the open configuration to permit the container to be removed from the printing module 10.

The expandable printing mechanism 50 and the article moving/container rotation assembly 260 are supported and relatively positioned within the module 10 on a mounting frame 20. In the illustrated embodiment, the mounting frame 20 has a channel-like configuration comprising an upper horizontal flange 22, a lower horizontal flange 26, and web 24 extending generally vertically between an edge of the upper horizontal flange 22 and an edge of the lower horizontal flange 26. The mounting frame 20 is formed from a material having adequate strength and rigidity and that is suitably machinable. The material is also preferably light weight. Aluminum is one example of a suitable material. In other examples, the mounting frame 20 could be formed (e.g., stamped) from sheet metal, molded from plastic, or cast in metal.

Various electronics, generally indicated at reference number 40, may be associated with the printing module 10, including, for example, a printed circuit board and connectors for communicating power and/or signals between the printing module 10 and external components such as a power source and a computer controller (described in more detail below).

The printing module 10 may be further enclosed within a housing (not shown), and the mounting frame 20 may be supported above a floor of the housing on a plurality of stand-offs 42 extending between the floor of the housing and the lower horizontal flange 26 of the mounting frame 20 (See FIG. 1).

Expandable Printing Mechanism

Figure 3:
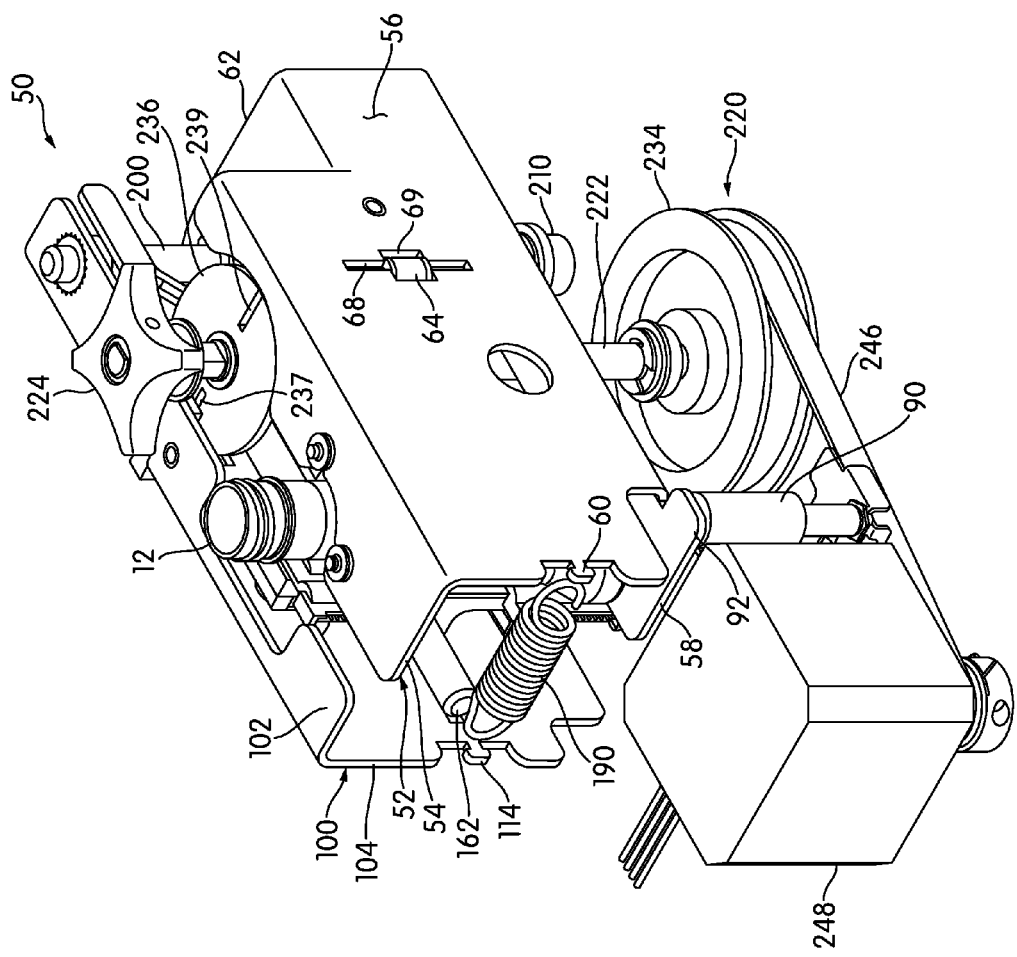
FIG. 3 is a frontal, right-hand partial perspective view of an expandable printing mechanism isolated from the remaining components of the printing module.

Continuing to refer to FIGS. 1 and 2, as well as FIG. 3, in which the expandable printing mechanism 50 is shown isolated from the mounting frame 20 and the container rotation assembly 260, the expandable printing mechanism 50 includes two frame or support elements on which various components of the expandable printing mechanism 50 are mounted and which are coupled together for hinge-wise relative movement between the open configuration and the closed, or printing, configuration. In the illustrated embodiment, a first support element comprises a roller bracket, generally indicated at reference number 52, and a second support element comprises a print head bracket, generally indicated at reference number 100. The roller bracket 52 operatively supports contact elements, e.g., rollers, (exemplary embodiments are described in further detail below) that contact or otherwise engage the article, (e.g., container 12) when the expandable printing mechanism 50 is in the closed or printing configuration. The print head bracket 100 operatively supports a print head assembly (an exemplary embodiment is described in further detail below) cooperatively configured and oriented with respect to the contact elements or rollers of the roller bracket 52 to print information on a surface of the article, e.g., container 12, when the expandable printing mechanism 50 is the closed or printing configuration, and the contact elements, e.g., rollers of the roller bracket 52 contact or otherwise engage the article, e.g., container 12, and hold the article in operative position with respect to the print head of the print head bracket 100.

The roller bracket 52 and the print head bracket 100 are respectively mounted at a common pivot shaft 200 for pivoting, hinge-wise rotation relative to one another. The pivot shaft 200 is mounted between the upper horizontal flange 22 and the lower horizontal flange 26 of mounting frame 20. A lower end of the pivot shaft 200 is supported within a bushing 210 mounted within the lower flange 26 of the mounting frame 20.

A coil spring 190 extending between spring hook 60 of the roller bracket 52 and spring hook 114 of the print head bracket 100 biases the free ends of the brackets 52 and 100 toward one another, so that a force expanding the brackets 52 and 100 in a hinge-wise fashion must overcome the force of the spring 190, and when that expanding force is removed, the brackets 52 and 100 will contract in hinge-wise fashion toward each other under the bias force of the spring 190.

An expander mechanism, which may comprise a bracket expander, is generally indicated at reference number 220, and is configured to contact or otherwise engage the roller bracket 52 and print head bracket 100 and to selectively expand the expandable print station 50 by pushing the roller bracket 52 and print head bracket 100 apart from each other against the bias of the spring 190 to open the roller bracket 52 and print head bracket 100 in hinge-wise fashion about the pivot shaft 200. The bracket expander 220 is also configured to selectively permit the roller bracket 52 and print head bracket 100 to close toward each other under the force of the spring 190 and maintain the brackets 52 and 100 at a prescribed minimum spacing corresponding to a printing configuration of the expandable printing mechanism 50.

Figure 4:
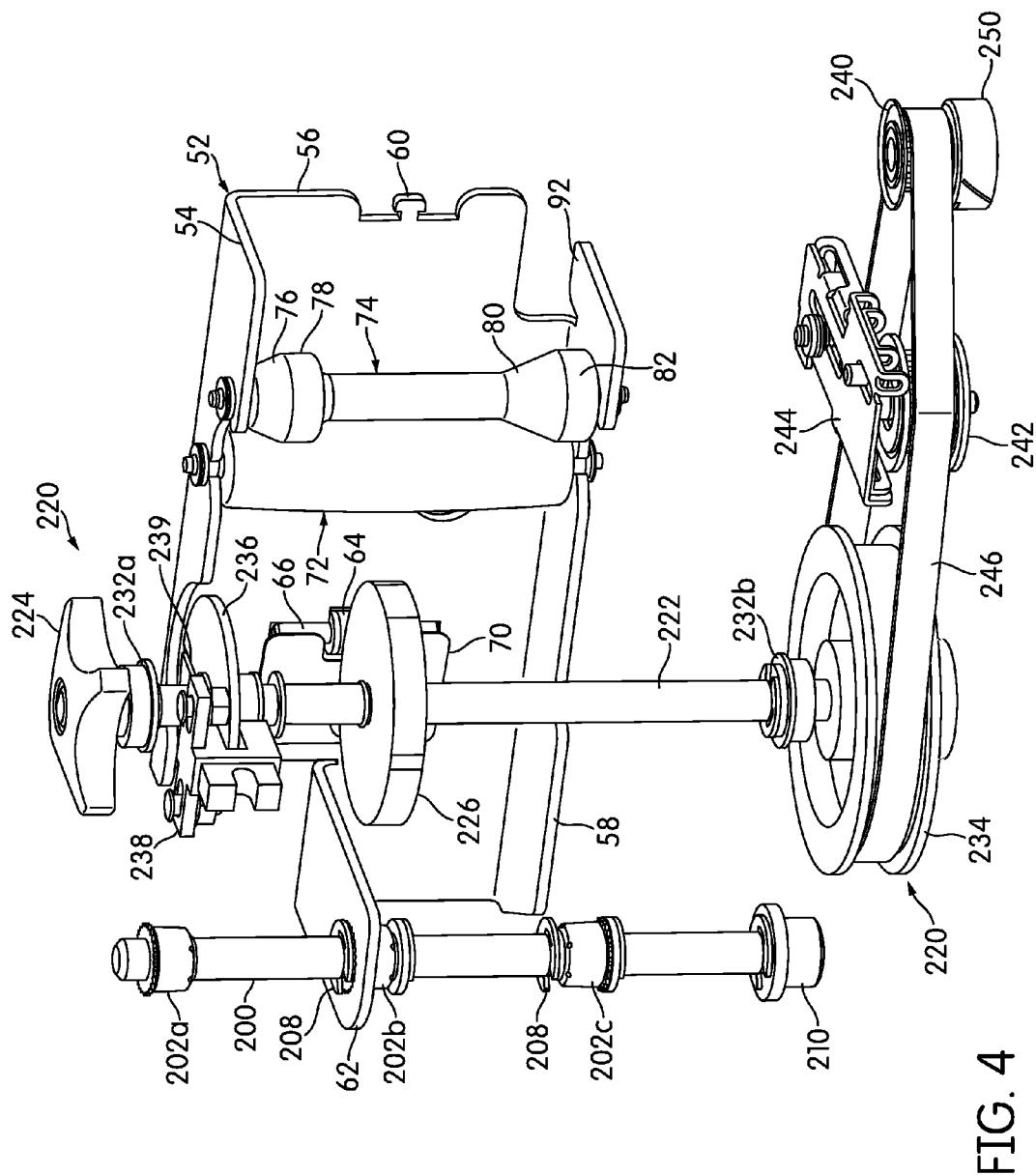
FIG. 4 is frontal, left-hand partial perspective view of a bracket expander, a roller bracket, rollers, and a pivot shaft of the expandable printing mechanism, with a print head bracket of the expandable printing mechanism omitted from the drawing.
Figure 5:
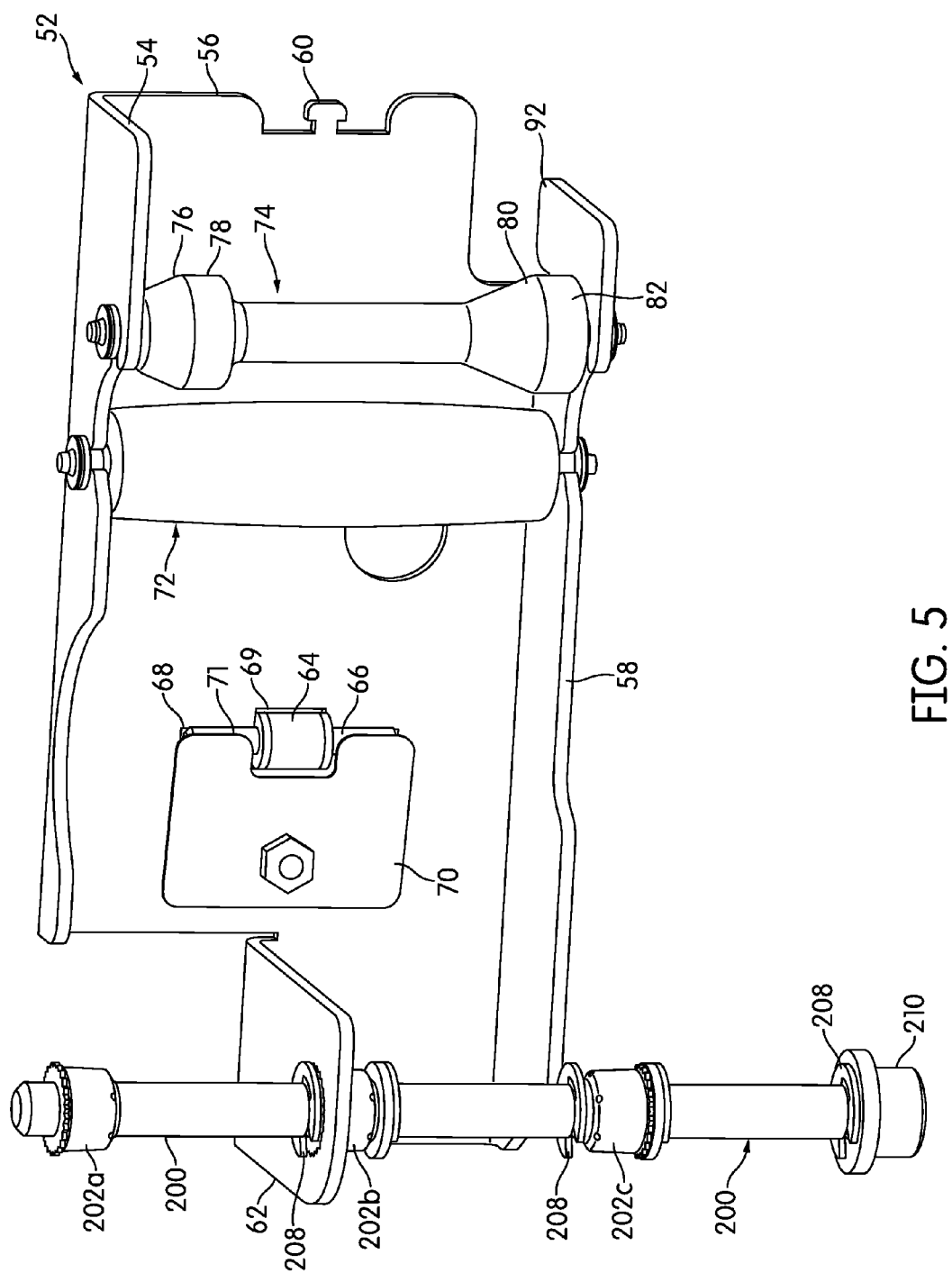
FIG. 5 is a frontal, left-hand partial perspective view of the roller bracket, the rollers, and the pivot shaft of the expandable printing mechanism.

Further details of the pivot shaft 200, the roller bracket 52, and the bracket expander 220 are shown in FIGS. 4 and 5. FIG. 4 is a frontal, left-hand partial perspective view showing the pivot shaft 200, the roller bracket 52, and the bracket expander 220 isolated from the remainder of the expandable printing mechanism 50. FIG. 5 is a frontal, left-hand partial perspective view showing the roller bracket 52 and the pivot shaft 200 isolated from the remainder of the expandable printing mechanism 50.

With reference to FIGS. 3, 4, and 5, in the illustrated embodiment, the roller bracket 52 has a generally channel-like construction with an upper horizontal flange 54, a lower horizontal flange 58, and a web 56 extending vertically between an edge of the upper flange 54 and an edge of the lower flange 58. Roller bracket 52 is preferably formed from a material that is sufficiently strong and rigid, is machinable, and light-weight. Aluminum is an example of a suitable material for roller bracket 52, although stamped sheet metal, plastic, or cast metal may be suitable in some embodiments. The roller bracket 52 is pivotably supported upon the pivot shaft 200 by means of the pivot shaft 200 extending through an opening formed in a pivot flange 62 extending laterally (e.g., horizontally) from the web 56 between the upper and lower flanges 54, 58 of the roller bracket 52. In the illustrated embodiment, the pivot flange 52 is axially fixed with respect to the pivot shaft 200 between a middle bushing 202(b) fixed at a middle location on the pivot shaft 200 and a circlip 208 or other suitable retainer element. Because the roller bracket 62 is supported on the pivot shaft 200 at only one location, i.e., at pivot flange 62, additional support and stability may be provided by an extension 92 of the lower flange 58 of the roller bracket 52 that is slidably supported on a roller bracket support 90 extending upwardly from the lower flange 26 of the mounting frame 20 (See, e.g., FIG. 3).

The expandable printing mechanism 50 includes one or more contact elements configured to contact an article to be printed on when the expandable printing mechanism 50 is in the closed or printing configuration and to hold a curved surface of the article in operative position with respect to a print head of the station 50 during relative movement between the print head and the curved surface. In the illustrated embodiment, the contact element(s) comprise two rollers 72, 74 rotatably mounted within the roller bracket 52 between the upper flange 54 and the lower flange 58 of the bracket 52.

Figure 5A:
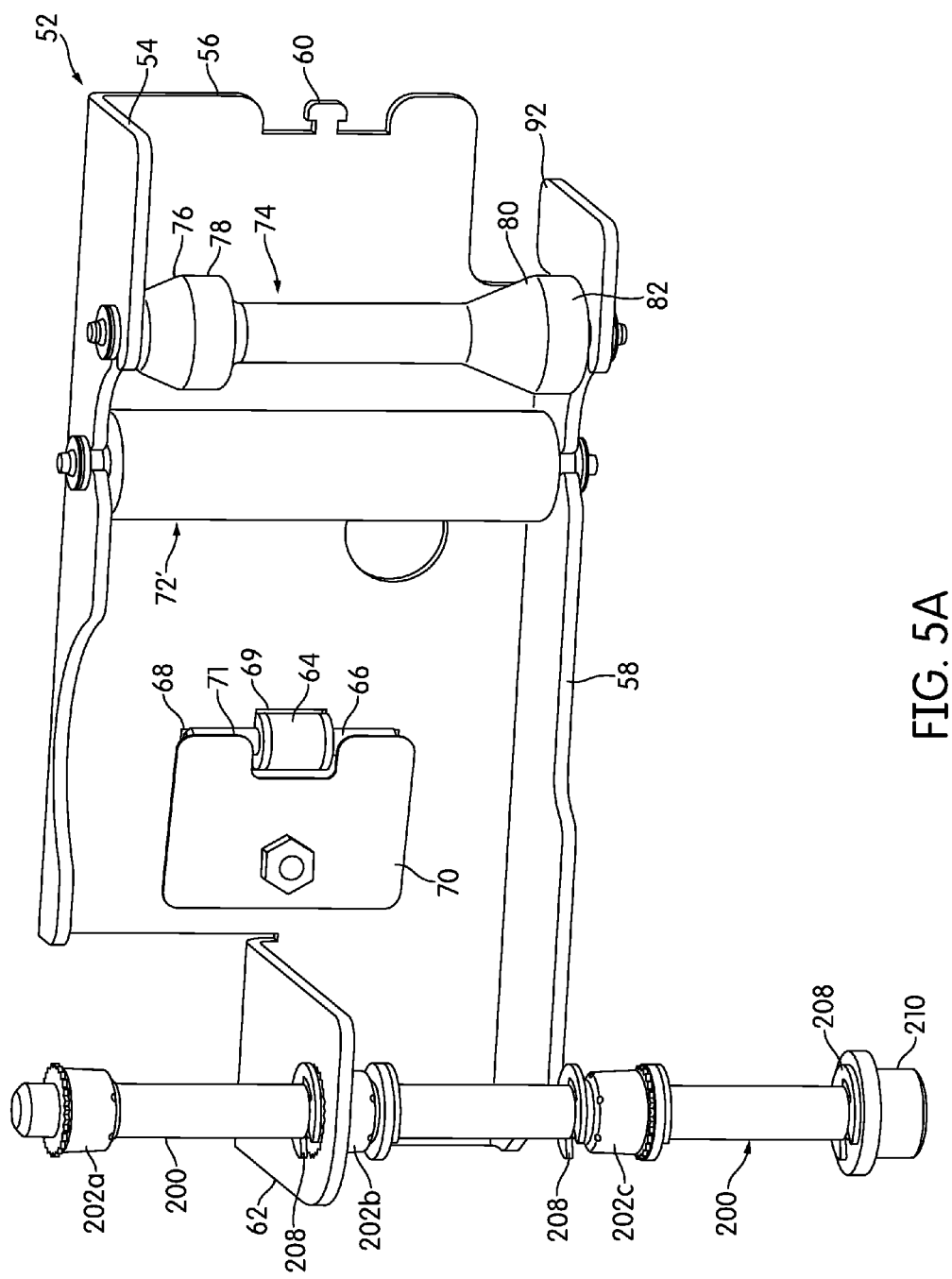
FIG. 5A is a frontal, left-hand partial perspective view of the roller bracket, the rollers, and the pivot shaft of an alternate embodiment of the expandable printing mechanism.

In the illustrated embodiment, roller 72 is a "clamping roller" that may comprise a convex roller mounted on a shaft extending between upper flange 54 and lower flange 58 and having a roller surface with a varying radius that increases from the longitudinal or axial ends of the roller 72 toward the middle of the roller at which point the radius is largest. In an alternate embodiment as shown in FIG. 5A, a clamping roller 72' may be a cylindrical roller having a generally constant radius.

Roller 74 is a "capture roller" that comprises a "dumbbell"—shaped roller mounted on a shaft or rod extending between upper flange 54 and lower flange 58 and having an upper head 76 and a lower head 80. Upper head 76 includes a bearing portion 78 and the lower head 80 includes a bearing portion 82. In one embodiment, each bearing portion 78, 82 presents a cylindrical outer surface, and the outer diameters of bearing portions 78 and 82 are the same. In an alternate embodiment, bearing portions 78 and 82 may have different respective diameters.

In various embodiments, rollers 72, 72', and 74 are machined from stainless steel.

In the illustrated embodiment, an outer, contact surface of the roller 72, 72' and the bearing portions 78, 82 of the dumbbell roller 74 have circular shapes in axial cross-section. This is to accommodate a generally circular article, such as tubular container 12, that is contacted by the rollers 72 and 74. It is contemplated, however, that rollers provided to contact an article having a surface may have non-circular configurations to accommodate a non-circular article to be contacted by the rollers.

As shown in FIGS. 1, 2, 3, and 5, a roller bearing 64 is rotatably mounted within the web 56 of the roller bracket 52 on a generally vertically-oriented bearing shaft 66 disposed within a vertical slot 68 having a width that is less than the diameter of the bearing shaft 66. The roller bearing 64 itself is disposed within a rectangular bearing slot 69 formed in the web 56. The bearing shaft 66 is secured within the vertical slot 68 by means of bearing retainer plate 70 having a notched end 71 that allows the bearing retainer plate 70 to hold the bearing shaft 66 in place within the slot 68 without interfering with the roller bearing 64. The bearing retainer plate 70 is secured to the web 56 of the roller bracket 52 by a bolt or other suitable fastener or fastening means such as a screw, adhesive, soldering, brazing, welding, etc.

Figure 6:
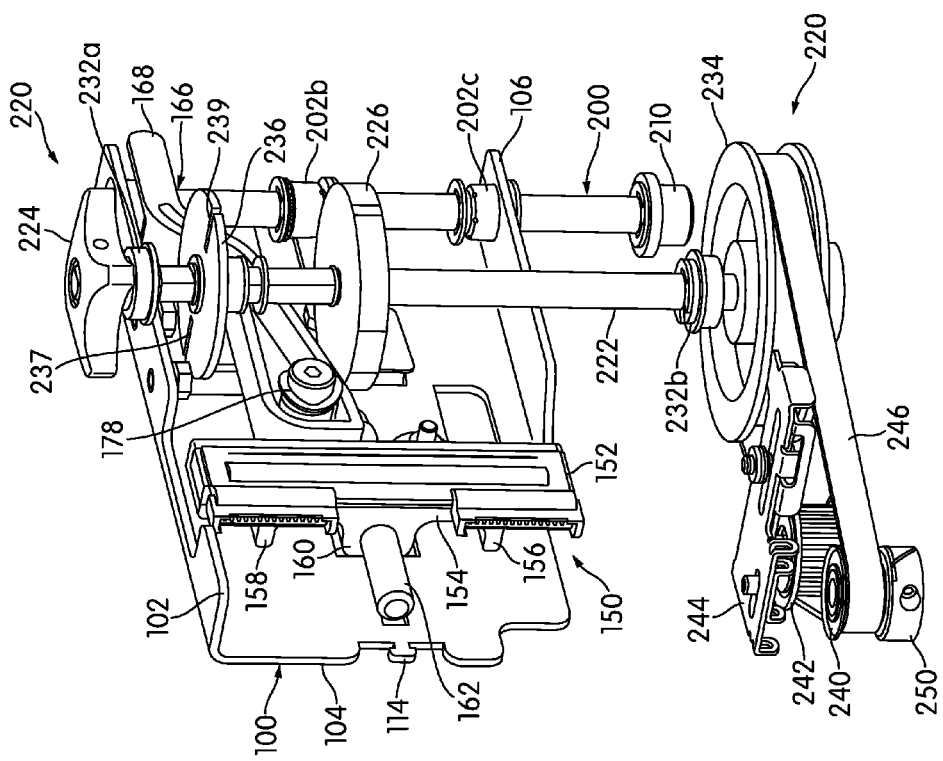
FIG. 6 is a frontal, right-hand partial perspective view of the bracket expander, a print head bracket, a print head assembly, and the pivot shaft of the of the expandable printing mechanism, with the roller bracket of the expandable printing mechanism omitted from the drawing.
Figure 8:
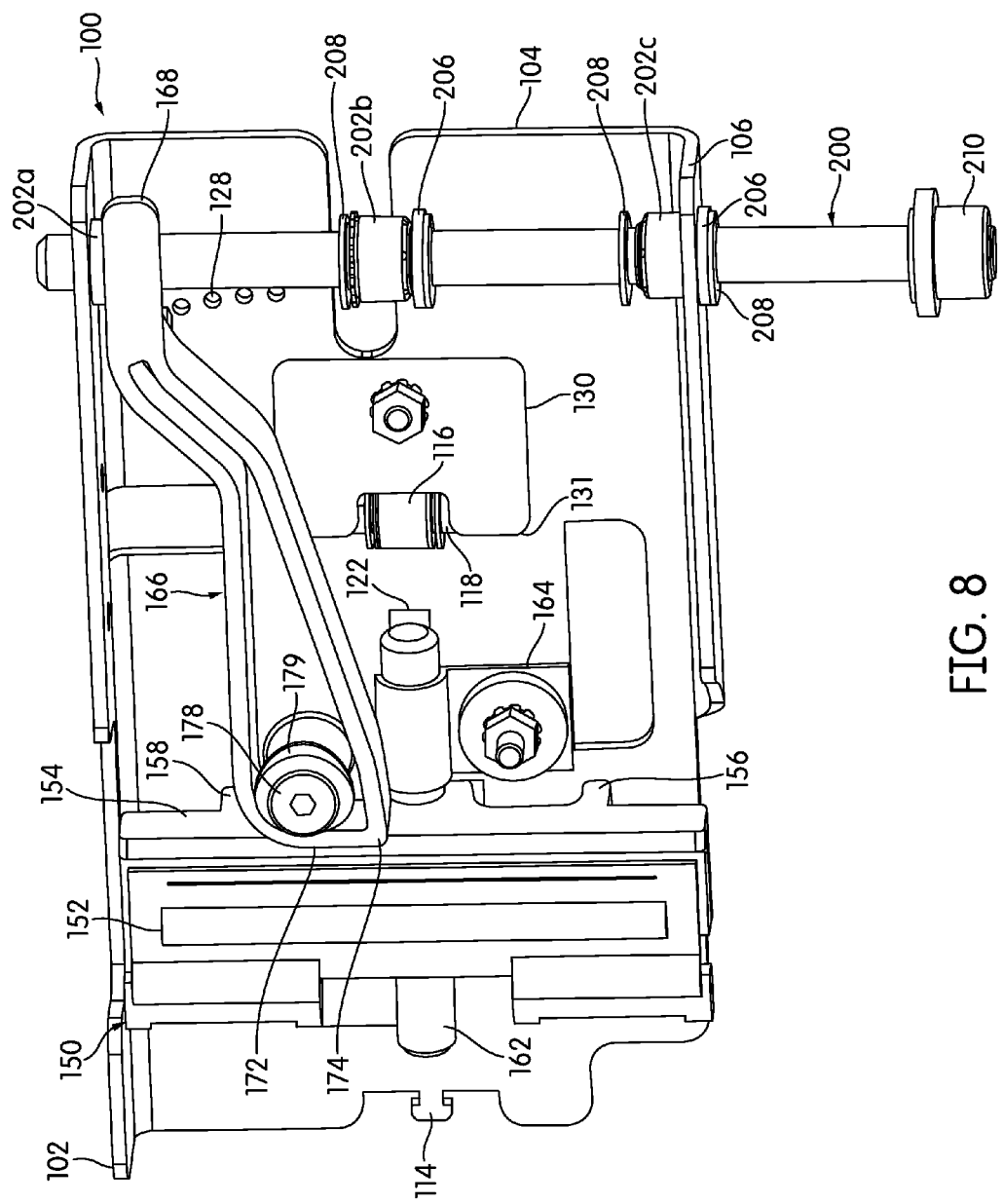
FIG. 8 rear, right-hand partial perspective view of the print head bracket, the print head assembly, and the pivot shaft of the of the expandable printing mechanism.
Figure 9:
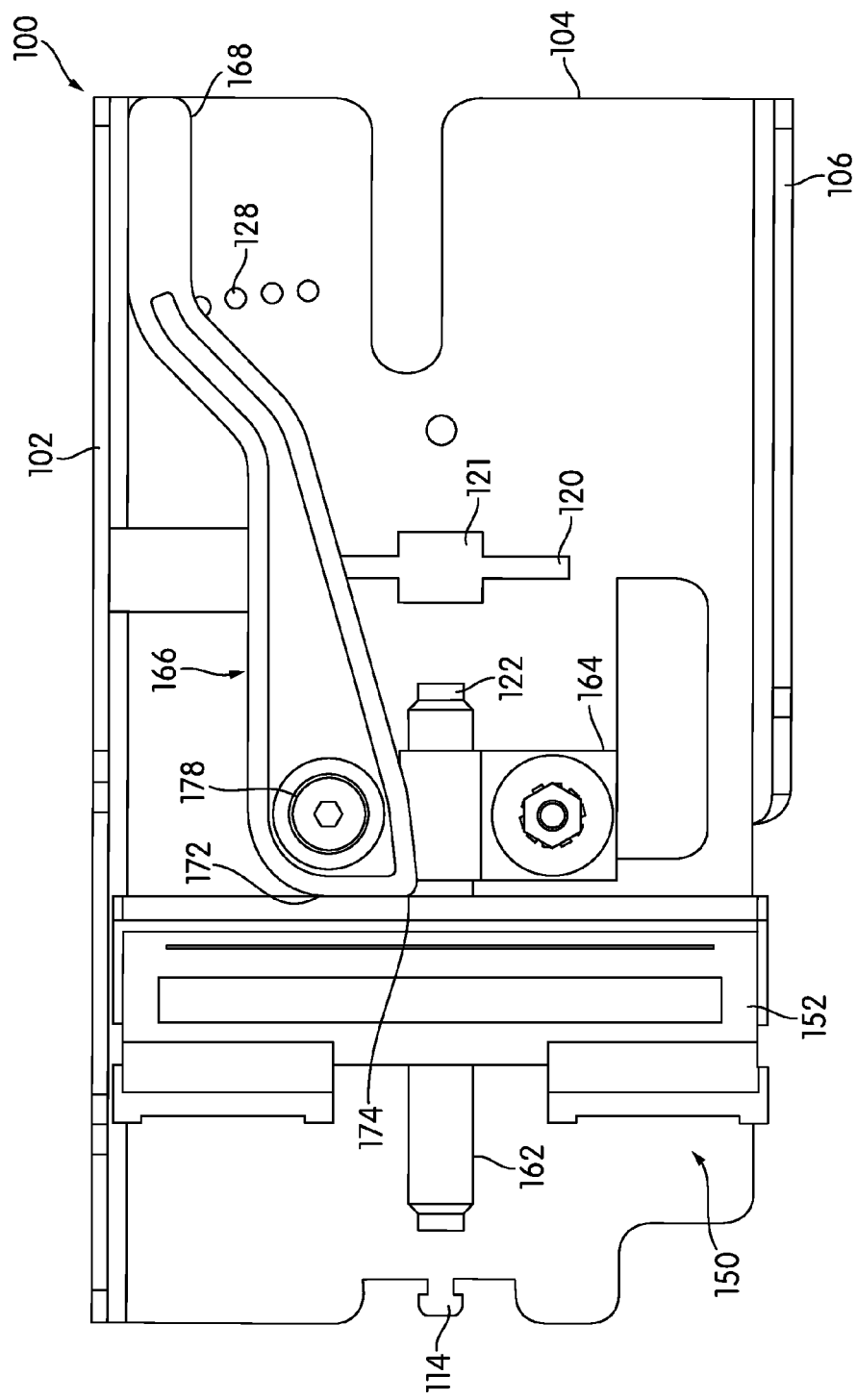
FIG. 9 is a right-side view of the print head bracket and print head assembly.
Figure 10:
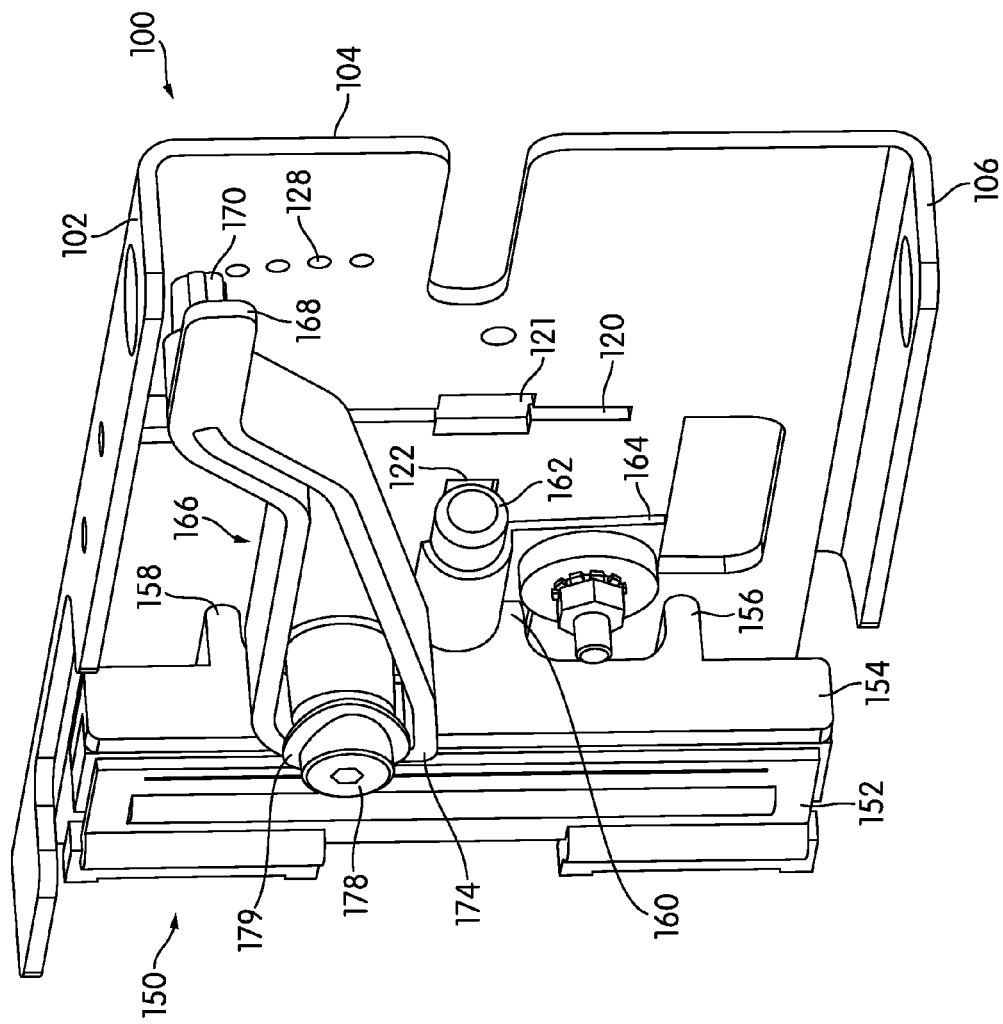
FIG. 10 is rear, right-hand perspective view of the print head bracket and the print head assembly.

Further details of the pivot shaft 200, the print head bracket 100, and the bracket expander 220 are shown in FIGS. 6 and 8. FIG. 6 is a frontal, right-hand partial perspective view of the print head bracket 100, the bracket expander 220, and the pivot shaft 200 isolated from the remainder of the expandable printing mechanism 50. FIG. 8 is a rear, right-hand partial perspective view of the print head bracket 100 and the pivot shaft 200 isolated from the remainder of the expandable printing mechanism 50.

The print head bracket 100 comprises a generally channel-like structure including an upper horizontal flange 102, a lower horizontal flange 106, and a web 104 extending vertically between an edge of the upper flange 102 and an edge of the lower flange 106. As with the roller bracket 52, suitable materials for forming the print head bracket 100 include aluminum, stamped sheet metal, plastic, and cast metal. In the embodiment shown, the print head bracket 100 is supported on the pivot shaft 200 by means of the pivot shaft 200 extending through openings formed in the lower flange 106 and the upper flange 102, and the bracket 100 is axially fixed with respect to the pivot shaft 200 by a top bushing 202a fixed to the pivot shaft 200, a bottom bushing 202c fixed to the pivot shaft 200, and associated washers 206 and circlips 208 or other suitable retainer elements.

As with the roller bracket 52, the print head bracket 100 further includes a roller bearing 116 rotatably mounted within the web 104 of the print head bracket 100 on a generally vertically oriented bearing shaft 118 disposed within a vertical slot 120 having a width that is less than the diameter of the bearing shaft 118. The roller bearing 116 is disposed within a rectangular bearing slot 121 formed in the web 104. The bearing shaft 118 may be secured within the vertical slot 120 by means of bearing retainer plate 130 having a notched end 131 that allows the bearing retainer plate 130 to hold the bearing shaft 118 in place within the slot 120 without interfering with the roller bearing 116. The bearing retainer plate 130 is secured to the web 104 of the print head bracket 100 by a bolt or other suitable fastener or fastening means such as a screw, adhesive, soldering, brazing, welding, etc.

A print head assembly 150 is secured to the web 104 of the print head bracket 100. The print head assembly includes a print head 152, which, in one embodiment, is a thermal print head, mounted on a print head platen 154. By way of example, a suitable print head is available from ROHM Co. Ltd., model no. KD3002-DF10A. The print head platen 154 serves as a mounting platform for the print head 152. The print head 152 may be mounted to the print head platen 154 by any suitable means, including mechanical fasteners such as screws, bolts, rivets, or the like. The print head platen 154 includes an enlarged shaft boss 160, through which extends a platen shaft 162 by which the print head assembly 150 is mounted to the web 104 of the print head bracket 100. In the illustrated embodiment, the platen shaft 162 is disposed within a horizontal shaft slot 122 having a width that is smaller than the diameter of the shaft 162. A retainer clip 164 secured to the web 104, e.g., by a mechanical fastener or the like, holds the platen shaft 162 within the shaft slot 122. In various embodiments, the print head assembly 150 is able to rotate about the platen shaft 162. To limit rotation of the print head platen 154 about the platen shaft 162, a lower blocking leg 156 and an upper blocking leg 158 project behind the print head platen 154 and contact the web 104 of the print head bracket 100.

Figure 11:
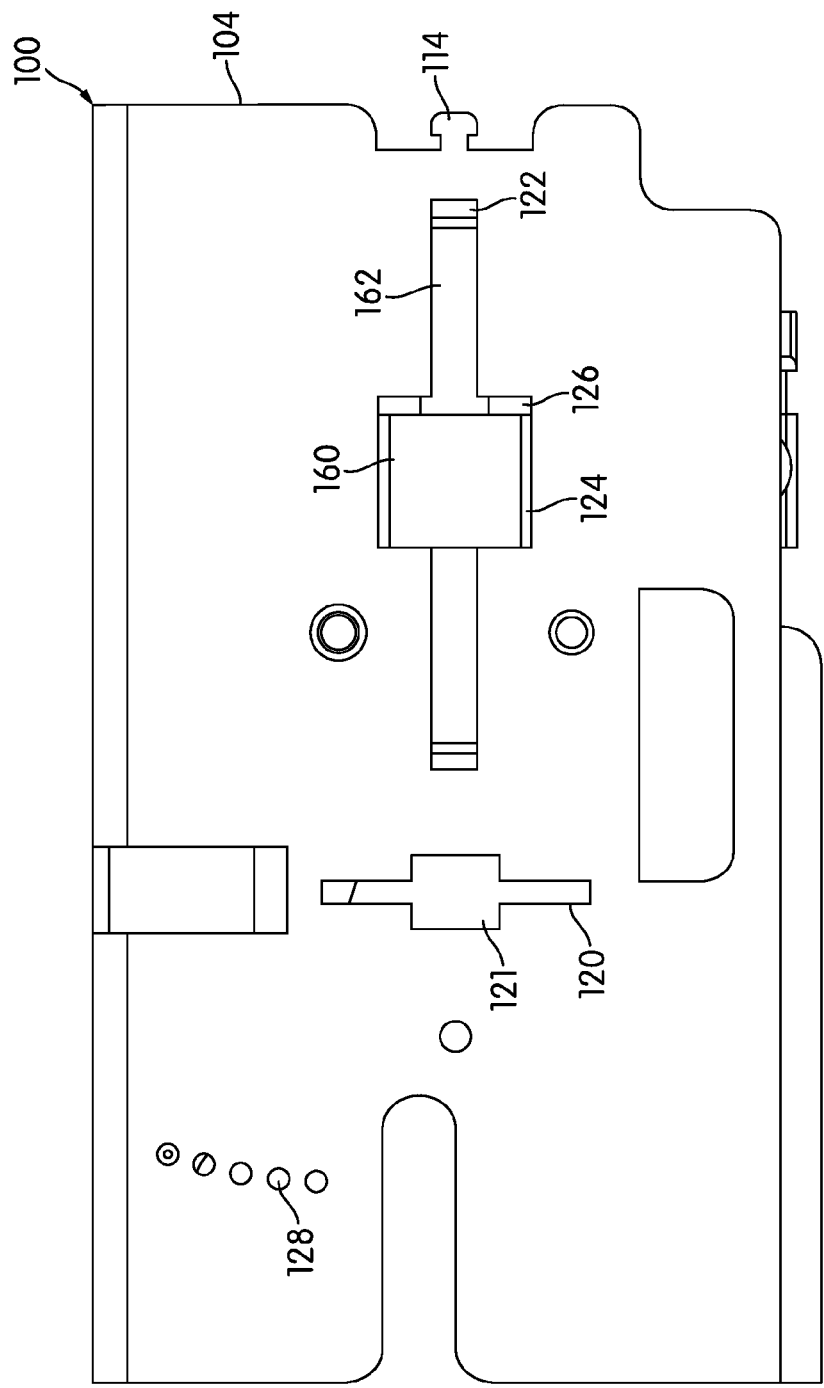
FIG. 11 is a left-hand side view of the print head bracket.

As shown in FIG. 11, showing a left-hand side of the print head bracket 100 opposite the right-hand side shown in FIGS. 6, 8, 9 and 10, the shaft boss 160 of the print head platen 154 extends into a rectangular opening 124 formed in the web 104 of the print head bracket 100. The width of the opening 124 is somewhat larger than the width of the shaft boss 160, thereby defining a clearance gap 126 between an edge of the opening 124 and a side of the boss 160 when the shaft boss 160 is disposed against one side of the rectangular opening 124. This gap 126 enables the print head platen 154 to slide along the platen shaft 162 by a limited amount to thereby enable adjustment of the lateral position of the print head assembly 150.

Referring again to FIGS. 8, 9, and 10, a print head adjustment lever 166 is mounted to the web 104 of the print head bracket 100 at a pivot point 178. Pivot point 178 may comprise a bolt or screw extending through an end of the adjustment lever 166 into the web 104 with a spring washer 179 for frictionally restricting rotation of the print head adjustment lever 166 about the pivot point 178. A cam end 172 of the adjustment lever 166 includes a contact point 174 that is in contact with one side of the print head assembly 150. As can be appreciated from FIG. 9, in the illustrated embodiment, clockwise rotation of the adjustment lever 166 will cause the contact point 174 to push the print head assembly 150 to the left in the figure. In various embodiments, a spring or other biasing element may be provided to bias the print head assembly 150 against the cam end 172 of the adjustment lever 166 (to the right in FIG. 9). Alternatively, or in addition, relative movement of the surface across the print head (i.e., from left to right in FIG. 9) will bias the print head assembly 150 against the cam end 172 of the adjustment lever 166. The adjustment lever 166 can be retained in a desired position by means of a protuberance 170 (see FIG. 10) that extends into one of a plurality of holes 128 formed on an arcuate path at a constant radial distance with respect to the pivot point 178 of the adjustment lever 166. A grasping end 168 of the print head adjustment lever 166 is configured to be manually grasped to enable manipulation of the adjustment lever 166 by removing the protuberance 170 from one of the openings 128, rotating the lever 166 in a desired clockwise or counterclockwise direction, and then reinsert the protuberance into one of the openings 128.

Referring to FIGS. 3, 4, and 6, the bracket expander 220 is disposed between the roller bracket 52 and the print head bracket 100 of the expandable printing mechanism 50. In an embodiment, the bracket expander 220 includes a driven shaft 222 on which is mounted a cam element that contacts both the first and second support elements, e.g., roller bracket 52 and print head bracket 100, and has a varying dimension so that in one orientation of the cam element, the portions of the cam element contacting the first and second support elements hold the first and second support elements apart by a first distance corresponding to the open configuration of the expandable printing mechanism 50, and in another orientation of the cam element, the portions of the cam element contacting the first and second support elements hold the first and second support elements apart by a second distance corresponding to the closed or printing configuration of the expandable printing mechanism 50.

Figure 7:
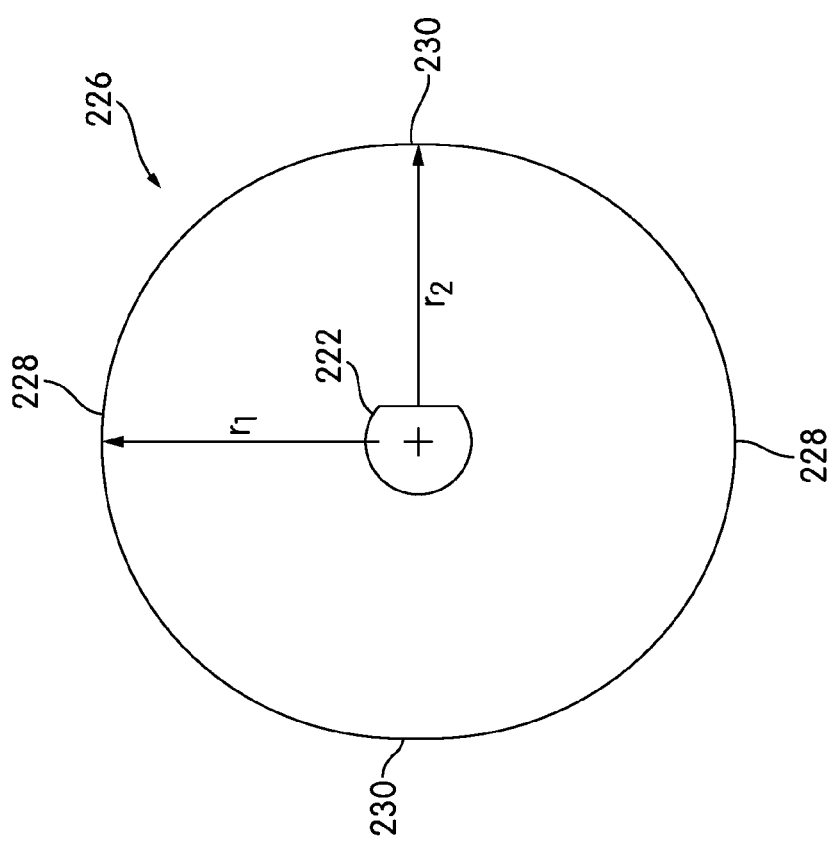
FIG. 7 is top plan view of a cam disc of a bracket expander of the expandable printing mechanism.

In the illustrated embodiment, the cam element comprises a cam disc 226. Details of the cam disc 226 are shown in FIG. 7, which is a plan view of the cam disc 226. Cam disc 226 may comprise a structure that is symmetrical about an axis of rotation corresponding to the longitudinal axis of the driven shaft 222 and may have a disc-like shape (i.e., having an axial dimension, or thickness, that is smaller, typically much smaller, than its radial dimension or width). In the illustrated embodiment, cam disc 226 is coaxially mounted on the shaft 222 and is non-circular, having a variable radius. In the embodiment shown, the cam disc 226 has two diametrically opposed portions 228 having a first radius r1 and two diametrically opposed portions 230 having a second radius r2. In the illustrated embodiment, portions 228 are spaced 90° from portions 230, and r1 is greater than r2. The cam disc 226 contacts the roller bearing 64 of the roller bracket 52 and contacts the roller bearing 116 of the print head bracket 100 to enable smooth, non-frictional relative movement between the cam disc 226 and the brackets 52 and 100. In an alternate embodiment, the roller bearings 64 and 116 are omitted and the cam disc contacts the roller bracket 52 and print head bracket 100 directly or through some other intermediate contact mechanism.

The driven shaft 222 is mounted within the mounting frame 20 for rotation with an upper spinner bearing 232*a* and a lower spinner bearing 232*b* supporting the shaft 222 at the upper flange 22 and the lower flange 26, respectively, of the mounting frame 20.

The bracket expander 220 further comprises a pulley wheel 234 coaxially mounted to the lower end of the driven shaft 222 and a motor 248 with a drive wheel 240 mounted to an output shaft of the motor 248, e.g., by hub fastener 250, and coupled to the pulley wheel 234 by means of a drive, or timing, belt 246. An exemplary, suitable drive wheel is the Fairloc® timing belt pulley available from SDP/SI New Hyde Park, N.Y.

Operation of the bracket expander 220 will now be explained.

With the shaft 222 and cam disc 226 in a first position (a bracket-expanding position) the contact portions 228 of radius r1 of the cam disc 226 contact the roller bearings 64, 116 of the roller bracket 52 and the print head bracket 100, respectively, (so that the roller bearings are spaced apart by a distance of 2×r1). In this position of the cam disc 226, the roller bracket 52 and print head bracket 100 are spaced-apart by the largest distance provided by the bracket expander 220, thereby putting the expandable printing mechanism 50 in its open configuration.

Rotation of the driven shaft 222 and cam disc 226 by 90° to a second position (a bracket contracting position), positions the contact portions 230 of radius r2 of the cam disc 226 in with contact the roller bearings 64, 116 of the roller bracket 52 and the print head bracket 100, respectively, (so that the roller bearings are spaced apart by a distance of 2×r2), the roller bracket 52 and print head bracket 100 are spaced-apart by the smallest distance allowed by the bracket expander 220, thereby putting the expandable printing mechanism 50 in its closed or printing configuration.

The driven shaft 222 is driven by the motor 248 supported on the lower flange 26 of the mounting frame 20 (see FIGS. 1 and 2). As noted above, motor 248 is coupled to the driven shaft 222 by the drive belt 246 trained over the pulley wheel 234 and the drive wheel 240 mounted to an output shaft of the motor 248. An idler wheel 242 coupled to a belt tensioner 244 ensures proper tension for the belt 246 and/or enables adjustment of the belt tension. An exemplary, suitable tensioner is available from York Industries, Inc., Garden City Park, N.Y., part no. DP3UB-2G24A74-B53PE-ACS.

Motor 248 may comprise a stepper motor. An exemplary, suitable stepper motor is available from Lin Engineering, Morgan Hill, Calif., model no. WO-4118S-01.

The bracket expander 220 may further comprise a hand wheel 224 coaxially or otherwise operatively attached to the driven shaft 222 to permit manual rotation of the cam disc 226 and thus manual expansion or contraction of the roller bracket 52 and the print head bracket 100.

To enable automated control of the printing module 10 by a controller, such as a computerized servo-controller or the like, signals indicative of the status or configuration of one or more components of the module may be provided as inputs to the controller, as will be described in further detail below. Accordingly, in one embodiment, the bracket expander 220 includes a detector or other means for generating a signal indicative of the status or position of the bracket expander 220—and thereby, the status, opened or closed, of the expandable printing mechanism 50.

In one embodiment, as shown in FIGS. 4 and 6, the bracket expander 220 includes an index wheel 236 coaxially mounted to the driven shaft 222. An optical sensor, such as a slotted optical sensor 238 mounted within the module, for example to the upper flange 102 of the print head bracket 100, detects the passage of a detectable feature of the index wheel 236, such as one or more radial slots 237, 239, formed in the wheel 236. In one embodiment, the optical sensor 238 comprises a slotted optical sensor forming an emitter/receiver pair, whereby a beam from the emitter to the detector is broken by the presence of the index wheel 236, until the wheel rotates such that one of the slots 237, 239 passes through the sensor, thereby completing the optical circuit from the emitter to the receiver and generating a signal indicative of the passage of the slot. Thus, by means of a detector such as the optical sensor 238 and the index wheel 236, a signal indicative of the position of the bracket expander, e.g., a bracket expanding position or in a bracket contracting position, can be generated.

With the expandable printing mechanism 50 in an open configuration—i.e., with the roller bracket 52 and the print head bracket 100 spread apart from each other by the bracket expander 220—a tubular container 12 can be inserted into an access opening 30 formed in the upper flange 22 of the mounting frame 20. The access opening 30 may be surrounded by a tube guide 28 defined by a plurality of resilient fingers that project downwardly and radially inwardly. When the tubular container 12 is inserted into the access opening 30, the distal ends of the fingers of the tube guide 28, which may be spaced apart by a distance that is less than the diameter of the tubular container 12, deflect outwardly to permit the tube to be inserted while pressing resiliently against the external surface of the tubular container, thereby holding the tubular container in a relatively stable lateral position.

Figure 19:
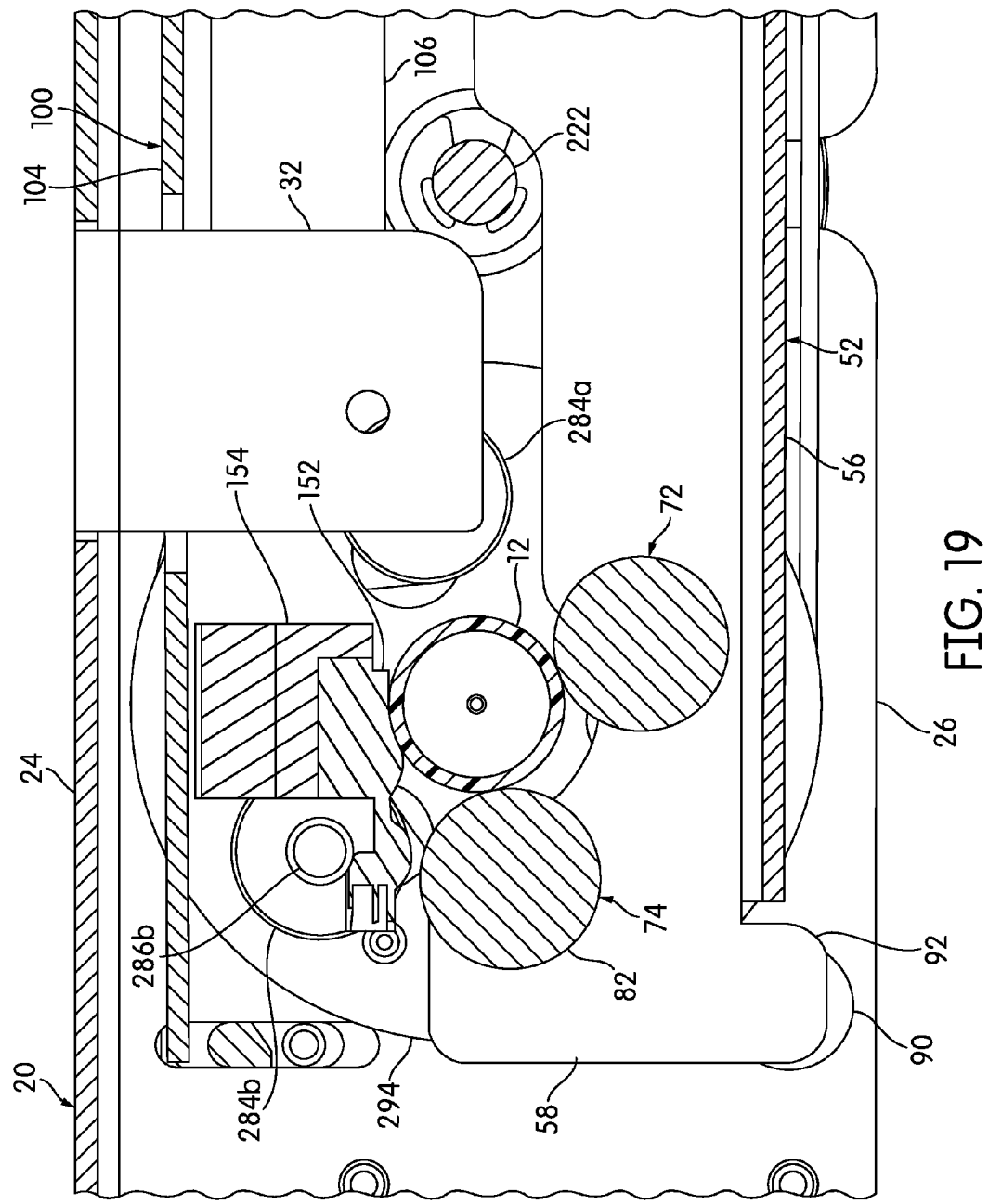
FIG. 19 is a partial cross-sectional view along the line A-A in FIG. 2.

When the tubular container 12 has been fully inserted into the expandable printing mechanism 50, the bracket expander 220 is activated to permit the roller bracket 52 and print head bracket 100 to close upon the tubular container 12. When the roller bracket 52 closes, the rollers 72 and 74 press against the tubular container 12, thereby pushing an opposite side of the tubular container 12 into operative contact with the print head 152 of the print head assembly 150. An embodiment of this arrangement is shown in FIG. 19, which is a partial transverse cross-sectional view of the module showing the rollers 72 and 74, including the tube bearing portion 82 of lower head 80 of the dumbbell roller 74, and the print head 152 engaged with the container 12 when the roller bracket 52 and print head bracket 100 are in the closed position.

The convex clamping roller 72, having a larger diameter at an axial center portion thereof than at the axial ends thereof, provides operable physical contact between the curved external surface of the tubular container 12 and the print head 152 along the entire length of the print head 152. In one embodiment, the tubular container 12 may have a convex shape with a diameter that increases from the axial ends thereof toward an axial middle portion thereof. This is described in further detail below. In other instances, the tubular container 12 may have a warped, or "banana" shape whereby the sides are curved from one end to the other. The dumbbell roller 74, having tube-bearing portion 78 at the upper head 76 and tube-bearing portion 82 at the lower head 80 bears against the upper and lower axial ends, respectively, of the tubular container 12, thereby ensuring that the tube is maintained in a stable position. One main function of the convex roller 72 is to straighten out the bowed sides of the tubular container 12. This functionality may be useful for "banana-shaped" or outwardly bowed containers where a concave side of the container does not mate flush with the print head 152, thereby leaving one or more gaps between the print head and the printable surface on the container side. The convex roller 72 helps push the tube wall flat up against the print head 152. In other embodiments, a clamping roller 72' (see FIG. 5A) having a cylindrical shape can provide sufficient pressure to effect sufficiently constant contact between the print head and the printable surface. The tube bearing portions 78, 82 of the dumbbell roller 74 press primarily at the upper and lower ends of the tubular container 12, thereby preventing lateral drift of the container without pressing on the side of the container in a manner that may counteract the straightening pressure applied by the convex roller 72.

In an embodiment, it is preferable that the clamping roller 72, 72' and the capture roller 74 be substantially parallel to the print head 152 so as to hold the tube against the print head 152 with substantially even pressure along the length of the print head. It is also preferable that the clamping roller 72, 72' and the capture roller 74 be parallel to the tube 12. In this regard, it is preferable that the roller bracket support 90 support the roller bracket 52 at the proper position so that the clamping roller 72, 72' and the capture roller 74 are parallel to the print head 152 and the tube 12.

Container Rotation Assembly

Figure 12:
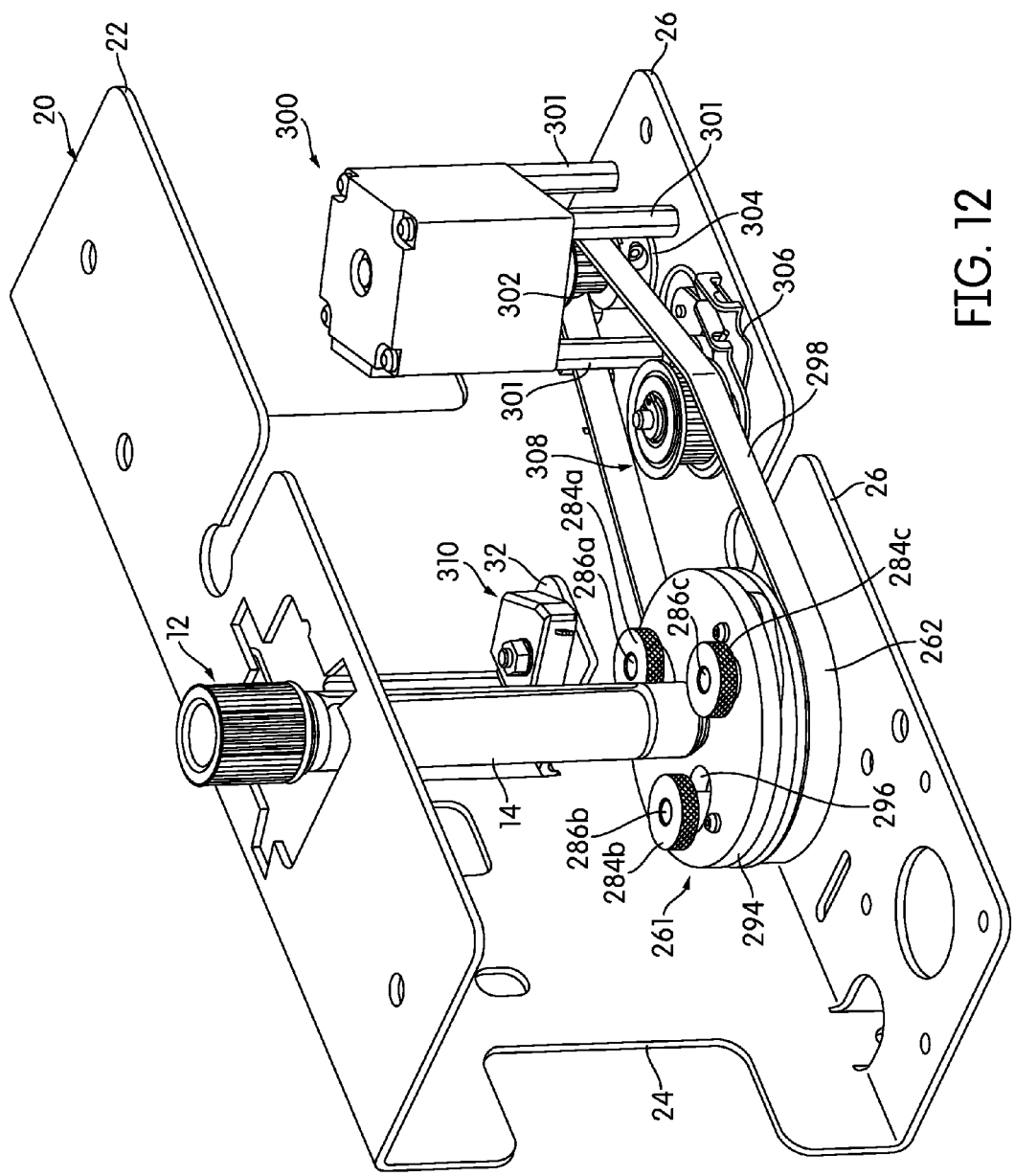
FIG. 12 is a frontal, right-hand partial perspective view of a container rotation assembly with a tubular container supported thereon and isolated from the remaining components of the printing module.

Aspects of the container rotation assembly 260, are shown in FIG. 12, which is a partial, top perspective view of the container rotation assembly 260 and mounting frame 20 isolated from the remaining components of the printing module 10.

The container rotation assembly 260 includes a carousel 261 on which the tubular container 12 is supported and which is operatively coupled for powered rotation to a motor 300 by means of a drive belt or timing belt 298. Drive belt 298 is trained around a drive wheel 302 mounted to an output shaft of the motor 300, e.g., by hub fastener 304, and the carousel 261. An exemplary, suitable drive wheel is the Fairloc® timing belt pulley available from SDP/SI New Hyde Park, N.Y. An idler wheel 308 attached to a belt tensioner 306 may be provided for ensuring and adjusting proper tension in the belt 298. An exemplary, suitable tensioner is available from York Industries, Inc., Garden City Park, N.Y., part no. DP3UB-2G24A74-B53PE-PS.

Motor 300 may comprise a stepper motor and is mounted above the lower flange 26 of the mounting frame 20 on a plurality (e.g., four) stand-offs 301 (see FIGS. 1 and 2). An exemplary, suitable stepper motor is available from Lin Engineering, Morgan Hill, Calif., model no. WO-211-13-02F.

A timing mark sensor 310 is positioned adjacent to the tubular container 12 carried on the carousel 261 and is configured to detect a timing mark, such as a darkened rectangle or other detectable graphic symbol provided on an external surface 14 of the tubular container 12, e.g., on a label secured to the external surface. In the illustrated embodiment, sensor 310 is supported on a depending shelf 32 extending laterally from the mounting frame 20 and through the print head bracket 100 (see also FIGS. 18 and 19). Timing mark sensor 310 is constructed and arranged to detect a timing mark on the printable surface, as will be described in further detail below, but is also operable to detect the presence of a tubular container 12 inserted into the expandable printing mechanism 50. In various embodiments, sensor 310 is a reflective sensor, such as Optek #OPB70FWZ or Optek #OPB748WZ.

In an embodiment, the capture roller 74 is located diametrically across from the sensor 310 (see FIG. 19, showing roller 74 across from the sensor-supporting shelf 32). Thus, in such embodiment, a dark-colored coating (e.g., black) may be applied to the roller 74 to minimize reflectance from the roller 74. The coating may be an epoxy powder coating.

Further details of the carousel 261 are shown in FIGS. 13, 14, 16, 17, and 18.

Figure 13:
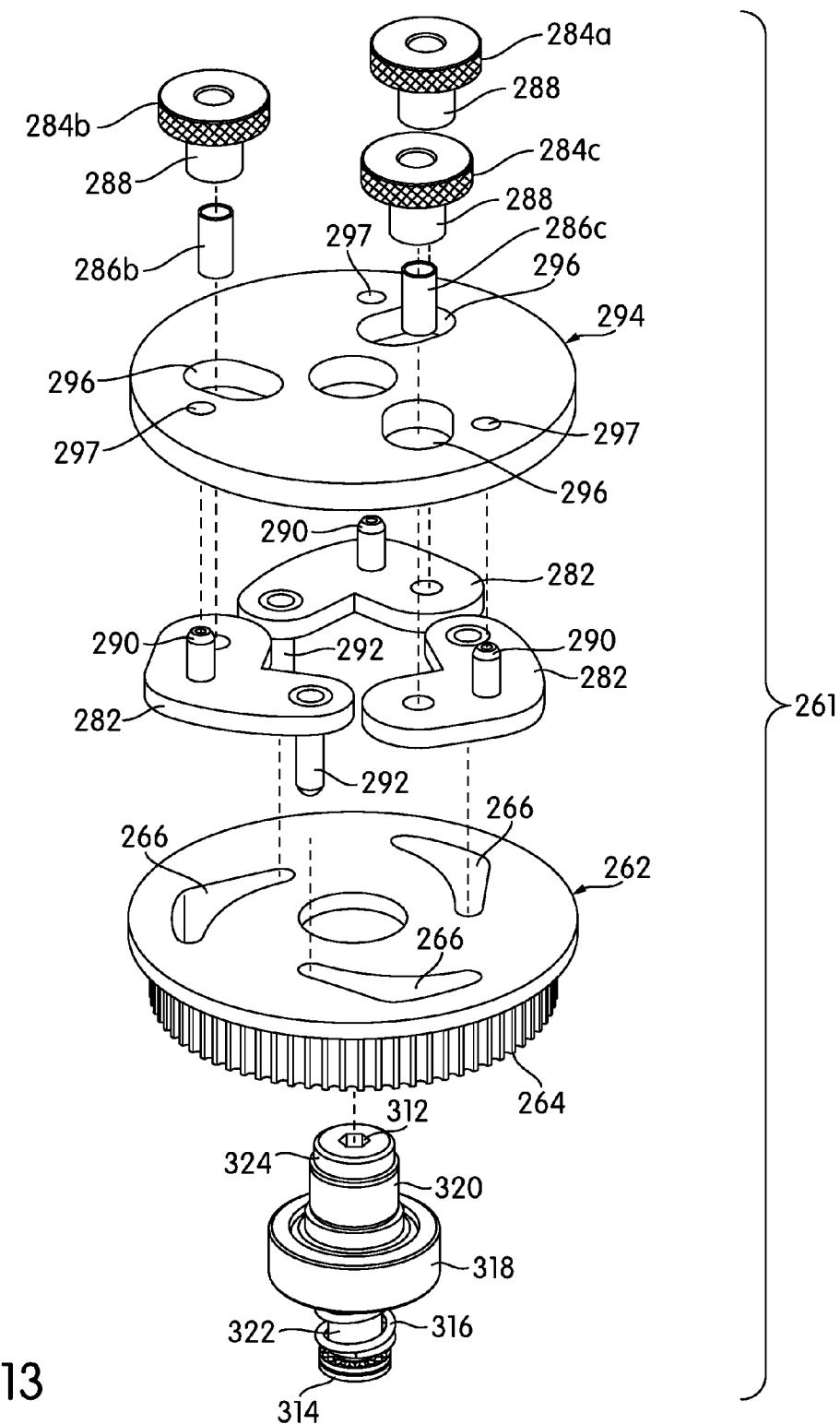
FIG. 13 is a top, exploded perspective view of a carousel of the container rotation assembly.
Figure 14:
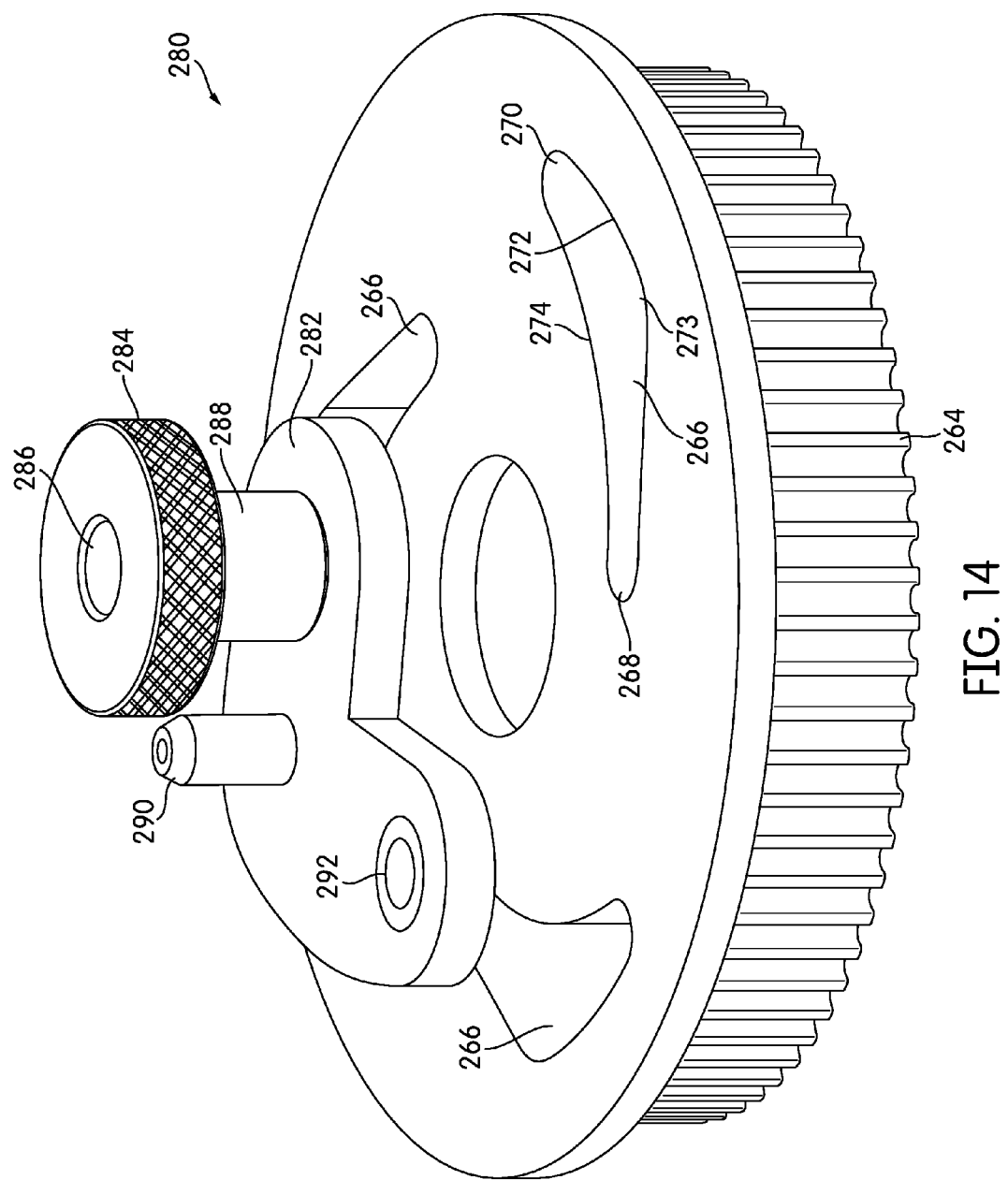
FIG. 14 is a top partial perspective view of the carousel of the container rotation assembly with a top disc omitted for the drawing.
Figure 16:
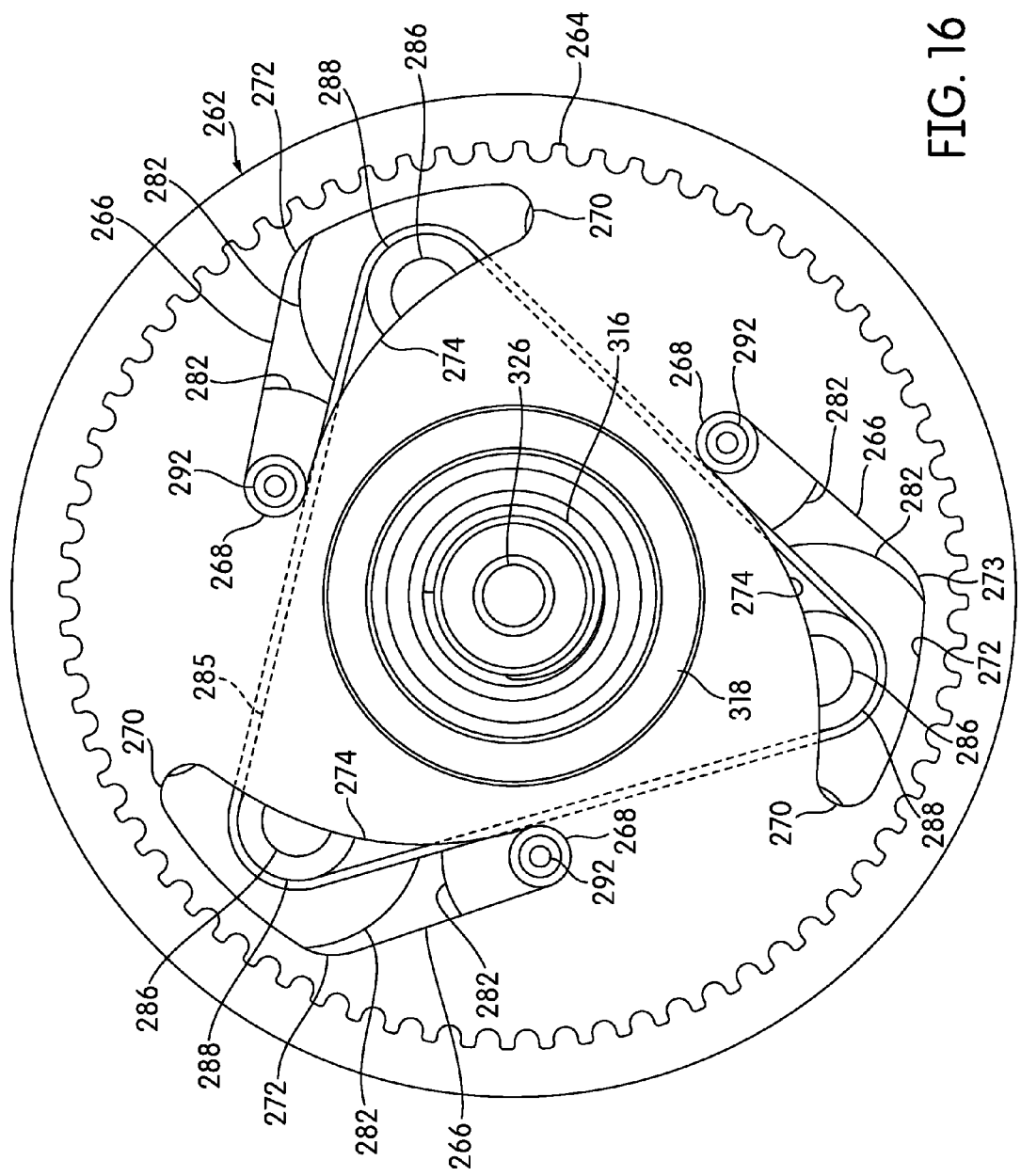
FIG. 16 is a bottom plan view of the carousel.

FIG. 13 is a top, exploded perspective view of the carousel 261 isolated from the remainder of the container rotation assembly 260. FIG. 14 is a partial, top perspective view of a portion of the carousel 261. FIG. 16 is a bottom plan view of the carousel 261.

Carousel 261 includes an upper disc 294 and a lower disc 262 mounted on a shaft 322 so as to be rotatable with respect to each other. Referring to FIGS. 13, 14 and 16, the lower disc 262 includes peripheral gear teeth 264 that are engaged by the drive belt 298. Lower disc 262 further includes three guide slots 266 each having a first end 268 and a second end 270. First end 268 is located radially inwardly from second end 270 relative to the center of the lower disc 262. Each guide slot 266 further includes a curved inner portion 274 extending from first end 268 to second end 270 and an outer portion 272 having a first curvature for a first extent from the first end 268 to a point 273 at which the curvature of outer portion 272 changes and a second curvature from the point 273 to the second end 270. In another embodiment, the inner and outer portions of each guide slot have the same or substantially the same curve profile and the width of each slot is substantially constant along its length.

Figure 15:
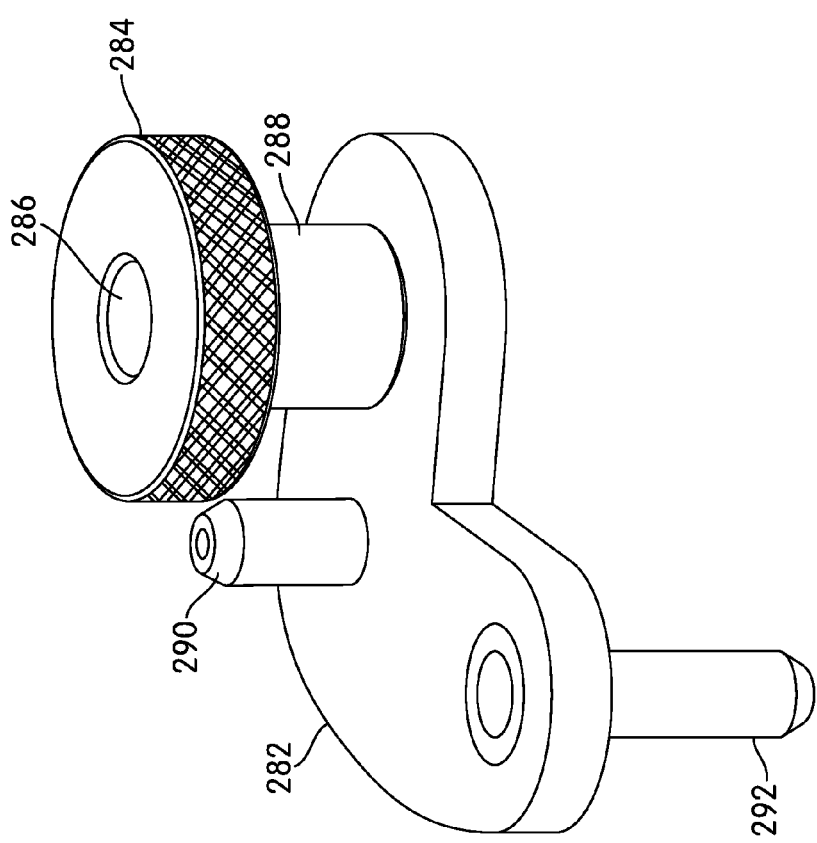
FIG. 15 is a top perspective view of a pivoting gripper assembly of the carousel of the container rotation assembly.
Figure 17:
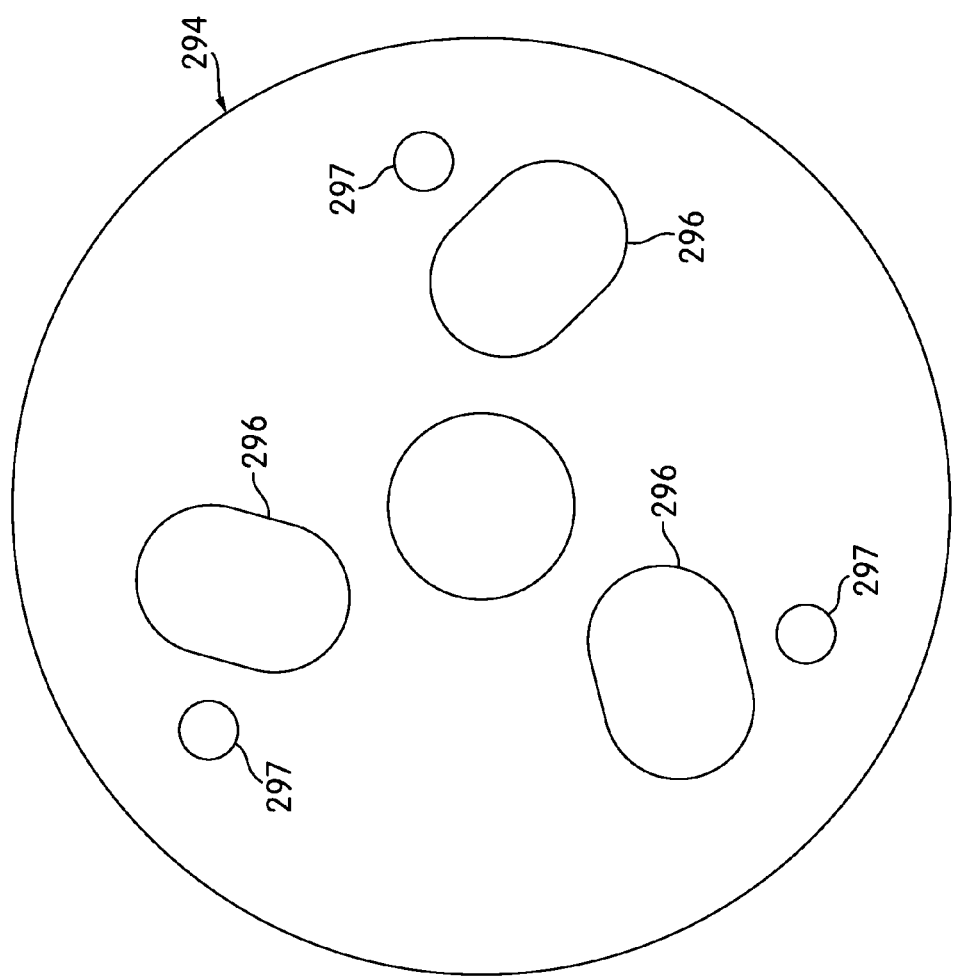
FIG. 17 is a top plan view of an upper disc of the carousel.

Referring to FIGS. 13 and 17, which is a top plan view of the upper disc 294, upper disc 294 includes three slots 296. Carousel 261 further comprises three pivoting gripper assemblies 280 disposed partially between the lower disc 262 and the upper disc 294. As shown in FIGS. 13, 14 and 15, each pivoting gripper assembly 280 includes a pivot arm 282, a knurled wheel 284, a mounting shaft 286 on which the knurled wheel is mounted, a spacer 288 beneath the knurled wheel 284 and surrounding the mounting shaft 286, a pivot pin 290, and a guide pin 292. In one embodiment, the carousel comprises three gripper assemblies comprising three knurled wheels 284a, 284b, 284c mounted on three mounting shafts 286a, 286b, 286c, respectively. As shown in FIG. 16, in various embodiments, resilient band 285 may be disposed over the spacers 288 on the mounting shafts 286a, 286b, 286c beneath the knurled wheels 284a, 284b, 284c to bias the knurled wheels of all the pivoting gripper assemblies 280 radially inwardly. Referring to FIG. 14, showing the lower disc 262 and only one of the gripper assemblies 280, each pivoting gripper assembly 280 is disposed atop the lower disc 262 with the guide pin 292 disposed within one of the guide slots 266 of the lower disc 262. The pivot pin 290 of each gripper assembly 280 extends upwardly from the pivot arm 282 into a pivot hole 297 of the upper disc 294, which is disposed atop the pivot arm 282. The mounting shaft 286 and spacer 288 extend through one of the slots 296 of the upper disc 294, and the knurled wheels 284a, 284b, 284c are disposed above the upper disc 294 (see FIG. 13).

Figure 18:
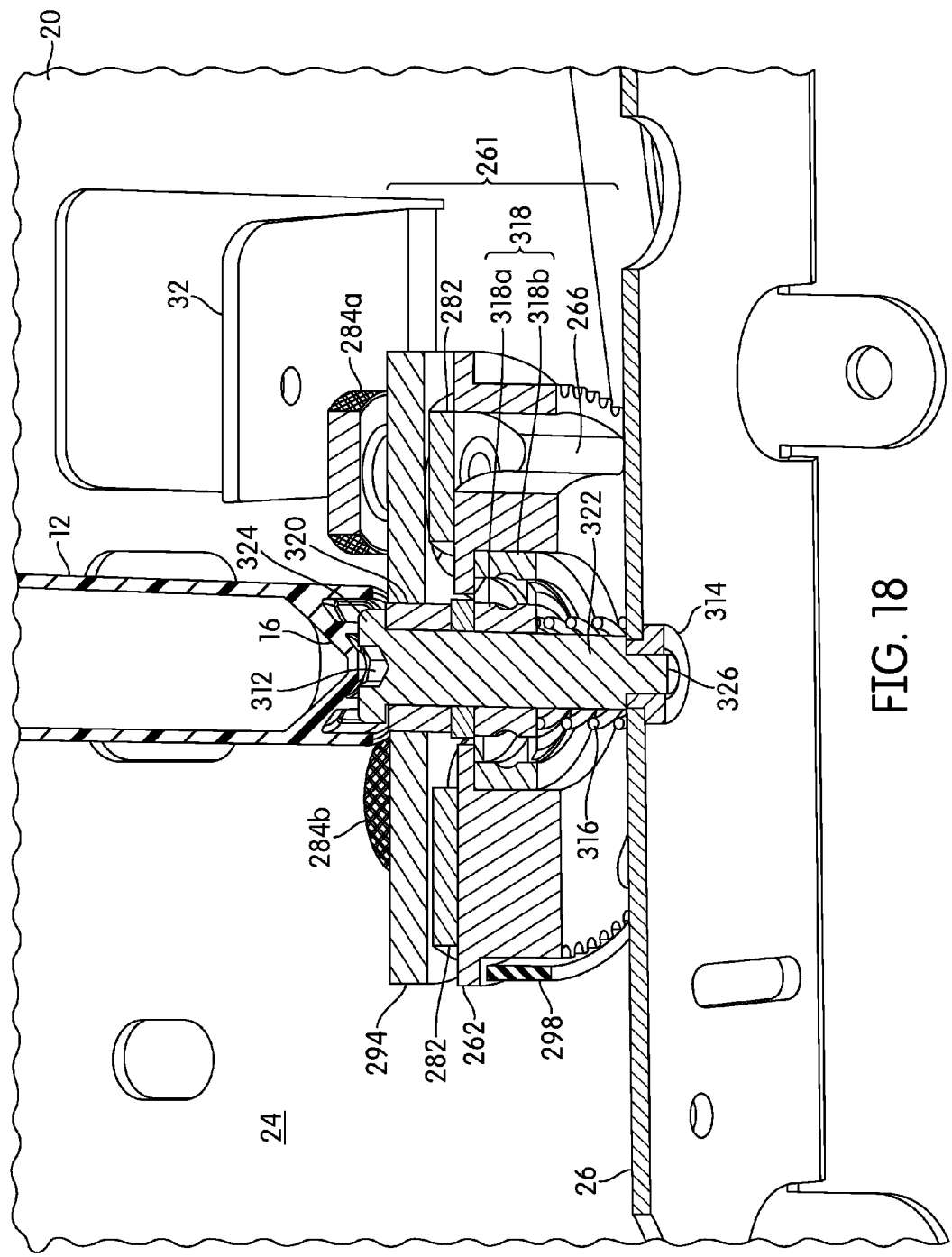
FIG. 18 is a bottom, partial perspective, cross-sectional view of the carousel, a container supported thereon and a mounting frame of the printing module.

FIG. 18 is a cross-sectional, perspective view showing the carousel 261 in cross-section and a portion of the mounting frame 20.

Referring to FIGS. 13 and 18, the carousel 261 is rotatably mounted to the lower flange 26 of the mounting frame 20 by means of a shaft 322 extending through the centers of the upper disc 294 and lower disc 262 and through the lower flange 26. In one embodiment, the container 12 includes a conical bottom portion 16 that nests within a recess 312 formed in the top of the shaft 322 for centering the container 12 and retaining the container 12 in that centered position. A lower end 326 of the shaft 322 may be secured within the lower flange 26 by means of a retainer 314, which may comprise a snap fit or threaded retainer. The upper disc 294 is rotatably mounted upon the shaft 322 by means of a roller bearing 320 or the like. The lower disc 262 is rotatably mounted upon the shaft 322 by means of a bearing race 318—comprising inner race 318a and outer race 318b—or the like. A coil spring 316 is disposed between the bearing race 318 (inner race 318a) and the lower flange 26 of the mounting frame 20. A cap portion 324 of the shaft 322 retains the upper disc 294 and lower disc 262 on the shaft 322. Spring 316 urges the assembly—comprising the bearing race 318, lower disc 262, pivot arms 282, upper disc 294, and roller bearing 320—against the cap 324 of the shaft 322.

Operation of the pivoting gripper assemblies 280 will now be described. Rotation of the lower disc 262 in a first direction (counter-clockwise for the configuration shown in FIG. 16) will cause the pivoting gripper assemblies 280 to pivot about their respective pivot pins 290 as their respective guide pins 292 move within an associated guide slot 266 from one end 268 to the opposite end 270, thereby moving their respective knurled wheels 286a, b, c radially inwardly and into contact with the end of a tubular container. As each guide pin 292 has reached the end of travel within the associated guide slot 266 so that relative movement between the guide pin 292 and the lower disc 262 is no longer possible, further rotation of the lower disc 262 will also rotate the upper disc 294, to which the pivoting gripper assemblies 280 are coupled via their pivot pins 290, and the tubular container. In addition, resilient band 285 helps bias the knurled wheels 284 radially inwardly into contact with the tubular container.

Reversing the rotation of the lower disc 262 will reverse the pivot of the gripper assemblies 280 as the respective guide pins 292 move within their associated guide slots 266 from end 270 to the opposite end 268, thereby withdrawing the knurled wheels 286 radially outwardly—against the bias of the resilient band 285—from the tubular container.

Note that the variation in the shape of the inner portion 274 and outer portion 272 of each guide slot 266 allows manual manipulation of the pivoting gripper assembly 280 when the guide pin 292 is at the widest portion, at point 273, of the slot 266.

Hardware and Software

Aspects of the subject matter disclosed herein may be implemented via control and computing hardware components, software (which may include firmware), data input components, and data output components. Hardware components include computing and control modules (e.g., system controller(s)), such as microprocessors, embedded controllers, application specific integrated circuits (ASICS), and computers, configured to effect computational and/or control steps by receiving one or more input values, executing one or more algorithms stored on non-transitory machine-readable media (e.g., software) that provide instruction for manipulating or otherwise acting on or in response to the input values, and output one or more output values. Such outputs may be displayed or otherwise indicated to a user for providing information to the user, for example information as to the status of the instrument or a process being performed thereby, or such outputs may comprise inputs to other processes and/or control algorithms. Data input components comprise elements by which data is input for use by the control and computing hardware components. Such data inputs may comprise signals generated by, for example, position sensors, motor encoders, barcode scanners, or RFID scanners, as well as manual input elements, such as keyboards, stylus-based input devices, touch screens, microphones, switches, manually-operated scanners, etc. Data inputs may further include data retrieved from memory. Data output components may comprise hard drives or other storage media, monitors, printers, indicator lights, or audible signal elements (e.g., chime, buzzer, horn, bell, etc.).

Control System

Figure 20:
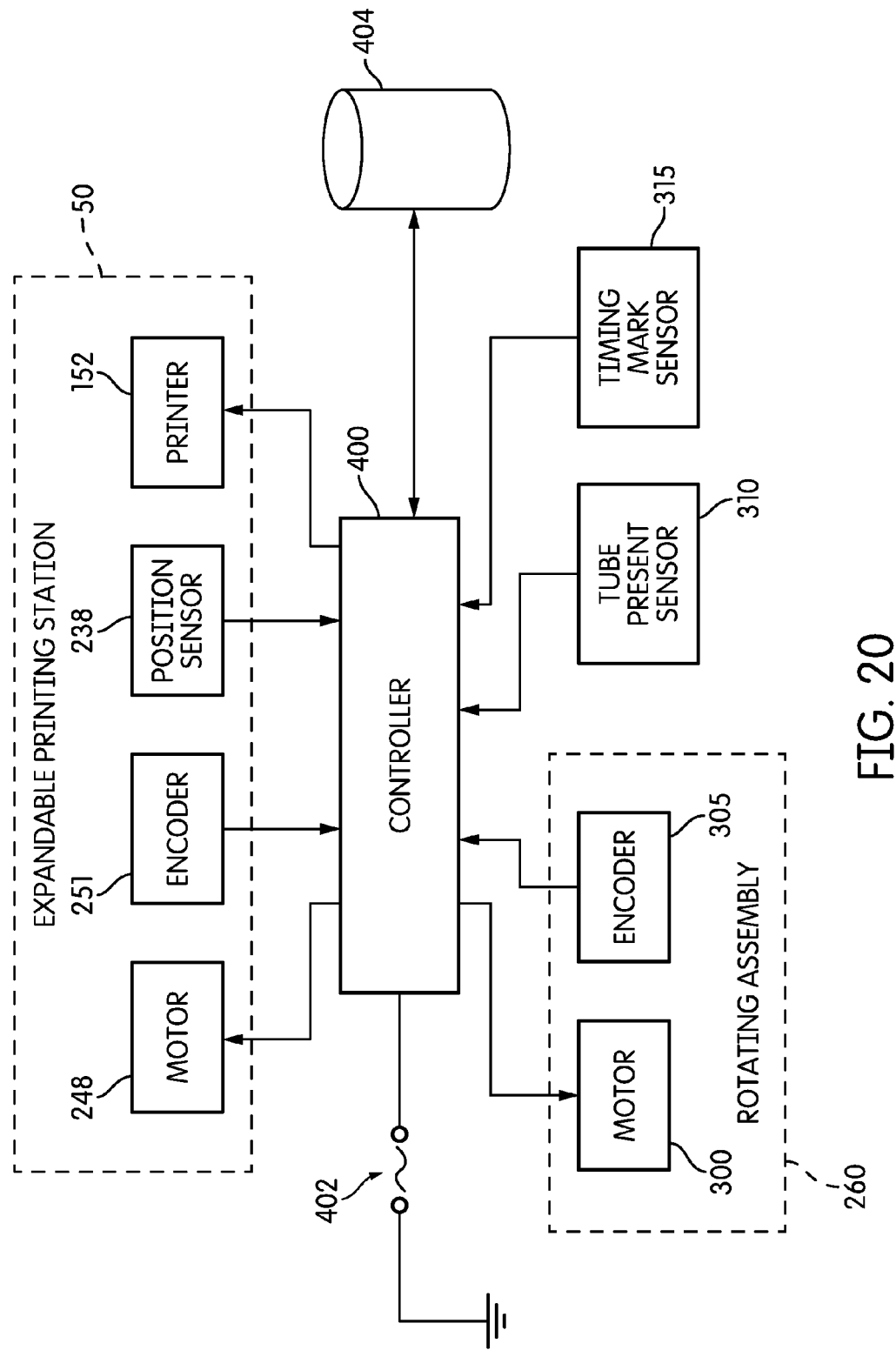
FIG. 20 is a block diagram that schematically illustrates a control architecture of the printing module.

FIG. 20 is a block diagram that schematically illustrates s control architecture for the printing module 10. An exemplary control architecture may include a controller 400, which monitors, communicates with, and controls aspects of printing module 10, including the expandable printing mechanism 50, the container rotation assembly 260, a tube-present sensor 310, and the timing mark sensor 315 (in an embodiment, the tube present sensor and the timing mark sensor may be the same sensor 310). The motor 248 of the expandable printing mechanism 50, and the motor 300 of the container rotation assembly 260 are coupled to and controlled by the controller 400, which is also connected to a controllable power supply 402. Controller 400 provides power and operational control signals to the motor 248 and motor 300. Controller 400 may also receive data from the motors 248, 300 in the form of rotary encoder counts from encoders 251, 305, respectively, as well as other feedback sensor signals.

Controller 400 comprises a computer system for executing software (which may include firmware) that effects operation, control, and monitoring of the printing module 10. Controller 400 is implemented via one or more logic elements, e.g., a computer, embedded controller, application specific integrated circuit, etc., and may include or access data storage memory 404, which may include random access memory (RAM), read only memory (ROM), flash memory, and other types of memory now known or later developed. Controller 400 may also include additional memory, including, for example, a hard disk drive and/or a removable storage drive, representing a magnetic tape drive, an optical disk drive, USB slot, memory card interface, internet memory, cloud-based memory, or any storage medium or format now known or later developed. Memory devices and storage units used herein may comprise any storage medium for persistent and/or volatile storage of electronic data now known or later developed. Such data may be stored within the storage medium in a database, which may comprise any data structure and format now known or later developed, including, for example, a relational database, an object database, a flat file, list, and so on, or some combination thereof.

In alternative embodiments, some or all of the memory may include other similar means for allowing computer programs or other instructions to be loaded into a computer system. Such means can include, for example, a removable storage unit and an interface. Examples of such can include a memory stick and memory stick interface, a secure digital card and interface, and other portable media and interfaces which allow software and data to be transferred to controller 400.

Software comprises instructions stored on non-transitory computer-readable media which, when executed by the logic element(s) of the controller 400, cause the control and computing hardware to perform one or more automated or semi-automated processes.

The computer system of controller 400 may also include a communications interface, which allows information (e.g., power, control and feedback signals, software, data, etc.) to be transferred between controller 400 and external devices. Examples of communications interface can include a modem, a network interface (such as an Ethernet card), a communications port, a PCMCIA slot and card, a USB-port, a Firewire port, or any interface now known or later developed. Information transferred via a communications interface is in the form of signals which can be electronic, electromagnetic, optical or other signals capable of being received by the communications interface.

The computer system of controller 400 can also include one or more input devices, such as a touch screen, stylus, keyboard, mouse or other pointing device, microphone, data scanners (e.g., barcode, RFID, etc.), and so on. Various output devices may also be included in the computer system, including indicator lights, a display, printer, tactile (e.g., vibratory) indicators, and audio speakers.

In this document, terms such as "computer program medium," "computer-readable medium," "computer usable medium," and the like are used to generally refer to media, such as removable storage units, a hard disk installed in hard disk drive, and other means for providing software and data to controller 400.

Computer programs (also called computer control logic) are stored in one or more portions of the memory 404 that is part of or accessed by controller 400. Computer programs can also be received via a communications interface. Such computer programs, when executed, enable the computer system of controller 400 to control the operation of the printing module 10 in accordance with aspects disclosed herein.

In an embodiment in which aspects of the subject matter disclosed herein are implemented using software, the software may be stored in a computer program product and loaded into the computer system of controller 400 using a removable storage drive, a hard drive, an interface, and/or a communications interface. The control logic (software), when executed by the processor of the controller 400, causes the processor to perform functional aspects of the subject matter as described herein via the systems, devices, apparatuses, sensors, encoder, etc. described above. An operating system may perform basic tasks such as recognizing input from an input device, sending output to an output device, managing files and system resources, and managing the various processes embodying computer programs running on the computer system.

Controller 400 may comprise a stand-alone system dedicated to the printing module 10, or one or more components of controller 400—e.g., processor, memory, interfaces, input/output devices, etc.—may be a shared part of a global controller that controls one or more components of an instrument or laboratory of which the printing module 10 is a component, in addition to the printing module 10.

As shown schematically in FIG. 20, with respect to the expandable printing mechanism 50, controller 400 receives signals from motor 248, and/or from an encoder 251, and from a position sensor of the bracket expander 220, such as the optical sensor 238 that detects the passage of slots 237, 239 of the index wheel 236. Controller 400 sends control (power) signals to the motor 248 to effect selective operation of the motor—and the bracket expander 220—and to the print head 152 to effect selective printing 248.

The controller 400 may also retrieve from the memory 404 the information that is to be printed by the pint head 152 or information that is to be associated with information to be printed by the print head 152. In the case of a container for biological or chemical samples or reactions, that information may comprise identification of the sample—e.g., type of sample material (e.g., chemical compound or sample, such as water, blood, urine, amniotic fluid, etc.), the source of the sample (e.g., origin of the compound or sample, such as clinical, industrial, environmental, or food sources, patient name, and other source information), the date the sample was acquired, or other identifying parameters. The information may also include the type of assay(s) or test(s) to be performed on the sample, identification of reagents or other materials added to or to be added to the sample, or any other information relevant to the contents of the container and/or procedures to be performed on the contents. Although identifying information itself may be printed directly onto the surface of the container, in many instances, the information that is printed onto the surface is a code that is human readable (e.g., a graphic and/or alphanumeric code) and/or machine readable (e.g., one and/or two dimensional barcode), and that code is associated, e.g., in a relational database, with the information associated with the container and/or its contents.

The information is retrieved by the controller 400 from memory 404 and is converted to control signals for operation of the print head 152 to print the required information (e.g., a barcode) onto the surface.

With respect to the container rotation assembly 260, controller 400 may receive signals from the motor 300, and/or encoder 305, and send control (power) signals to the motor 300 to effect selective operation of the motor 300.

Controller 400 may also receive signals from the tube present sensor 310 and the timing mark sensor 310, which signals are processed to generate control signals to motor 248 to effect operation of the bracket expander 220, to motor 300 to effect operation of the container rotation assembly 260, and to the print head 152 which, in combination with operation of the container rotation assembly 260, applies the printed information to a curved surface of the tube.

Figure 21:
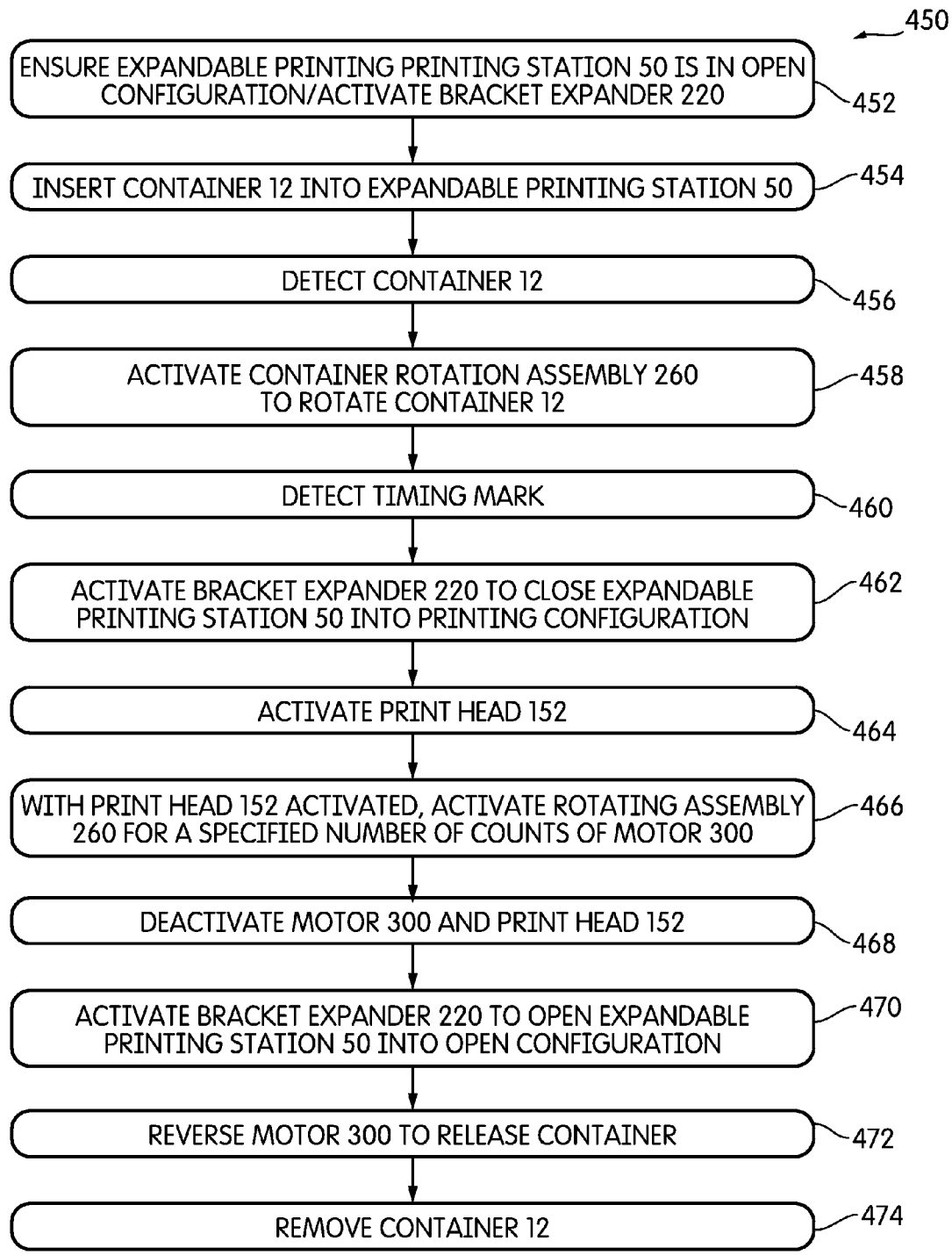
FIG. 21 is a flowchart showing a control algorithm of the printing module.

A process or algorithm 450 implemented in the operation of the printing module 10 is represented by a flow chart in FIG. 21. In one embodiment, algorithm 450 is an automated process whereby the printing module 10 can be operated to print information onto the curved surface of an article wholly or substantially without human intervention. In an embodiment, all or part of the algorithm 450 may be encoded as executable software (e.g., firmware) using any suitable programming language, such as Assembly, C, or C++, and/or all or part of the algorithm may be "hard coded" or "hard wired" in a control module, such as an embedded controller, for example, an application specific integrated circuit ("ASIC"). The algorithm 450 may be executed by a controller module, such as controller 400 described above, and all or part of any executable software may be stored in a manner that is functionally accessible to the controller 400, for example in memory 404.

In an initial step 452 of the algorithm 450, the module 10 is readied to receive an article, such as container tube 12, having a curved surface by insuring that the expandable printing mechanism 50 is in an open configuration and thus in a configuration amenable to receiving the article. That the expandable printing mechanism 50 is in the open configuration can be ascertained and/or confirmed by receiving signals from sensors or other indicators monitoring certain parameters that are indicative of the configuration—opened or closed—of the expandable printing mechanism. For example, in one embodiment, step 452 can be performed by, e.g., the controller 400 receiving a signal from the slotted optical sensor 238 that detects features of the index wheel 236 to thereby indicate the position of the cam disc 226 of the bracket expander 220. If the position of the cam disc 226, as indicated by the signal from the sensor 238 corresponding to a rotational position of the index wheel 236, is such that the portions 228 of the cam disc 226 are in contact with the roller bracket 52 and print head bracket 100 of the expandable printing mechanism 50, the printing mechanism 50 is in the open configuration. On the other hand, if the position of the cam disc 226 is such that portions 230 of the cam disc 226 are in contact with the roller bracket 52 and print head bracket 100, the expandable printing mechanism is in the closed or printing configuration.

If the expandable printing mechanism 50 is not in the open configuration, the bracket expander 220 is activated by controller 400 sending an activation signal (control and power signal) to the motor 248 to rotate the shaft 222 and cam disc 226 until the portions 228 of the cam disc are in contact with the roller bracket 52 and the print head bracket 100, thereby opening the expandable printing mechanism 50 into the open configuration. If motor 248 is a stepper motor, it can be activated for a specified number of steps to rotate the shaft 222 and cam disc 226, e.g., 90°, into position for opening the expandable printing mechanism 50, provided that the initial rotational position of the shaft 222 and cam disc 226 is known. In addition, or alternatively, the motor 248 can be activated until a signal is received from the optical sensor 238 indicating that the portions 228 of the cam disc 226 are in contact with the roller bracket 52 and print head bracket 100. When a signal indicating that the expandable printing mechanism 50 is in the open configuration is received by the controller 400, controller 400 deactivates the motor 248.

In step 454, the article, e.g., container tube 12, is inserted into the access opening 30 of the module 10. The article can be placed into the module 10 by any suitable means or mechanism, including manually or by a robotic pick-and-place mechanism.

In step 456, the container 12 is detected, e.g., by sensor 310, to confirm that it has been fully and properly inserted into the module 10. The container's presence can be confirmed by, for example, tube present sensor 310 and/or any suitable sensor, such as, for example, a contact sensor, an optical sensor, or a proximity sensor in communication with the controller 400.

In step 458, the rotation assembly 260 is activated by the controller 400 to begin rotating the container 12. The rotation assembly 260 can be activated by sending a control and power signal to the motor 300 to rotate the carrousel 261.

In step 460, the article, e.g., container 12, is rotated until a timing mark located on the container 12 is detected by the timing mark sensor 310. In an embodiment, detection of the timing mark indicates that the container 12 is in a predetermined position with respect to the print head assembly 150. The predetermined position could be the position at which printing should be commenced, or it could be a position that is at a known rotational offset from the printing position, such that printing will commence after the container has been rotated from the predetermined position by the offset amount.

Thus, in the context of this disclosure, the timing mark on the surface of the container does not necessarily relate to time or a temporal parameter, but instead is a spatial parameter for detecting locations and/or distances with respect to the detected location and/or with respect to one or more dimensions of the timing mark.

Further details regarding exemplary methods for detecting a timing mark and for positioning the tube at a print-ready position are described below.

After the timing mark has been located, in step 462, the bracket expander 220 is activated by the controller 400 to alter the expandable printing mechanism 50 into a closed or printing configuration. Bracket expander 220 can be activated and controlled by sending a control and power signal to motor 248 to operate the motor for a specified number of steps to rotate the cam disc 226, e.g., 90°, from a first position corresponding to the open configuration of the expandable printing mechanism 50, i.e., a position in which the portions 228 of the cam disc 226 are in contact with the roller bracket 52 and print head bracket 100, to a second position corresponding to the closed configuration of the expandable printing mechanism 50, i.e., a position in which portions 230 of the cam disc 226 are in contact with the roller bracket 52 and the print head bracket 100. Optical sensor 238 can be monitored by the controller 400 to confirm that the shaft 222 and cam disc 226 have rotated to the proper position for the closed configuration of the expandable printing mechanism 50. Alternatively, or in addition, the motor 248 can be activated by sending power to the motor 248 to rotate the shaft 222 and the cam disc 226 until the slotted optical sensor 238 indicates that the cam disc 226 has rotated from the first position corresponding to the open configuration of the expandable printing mechanism 50 to the second position corresponding to the closed or printing configuration of the expandable printing mechanism 50, at which time power to the motor 248 is terminated.

In step 464, when the article, e.g., container 12, is in the printing position with respect to the print head assembly 152, the print head assembly 152 is activated by the controller 400 to begin printing on the curved surface. The rotation assembly 260 can be controlled such that detection of the timing mark in step 462 results in a momentary pause in the rotation of the carousel 261 and container 12, at which time the print head 152 is activated in step 464 before rotation of the carousel 261 and container 12 is resumed. Alternatively, rotation assembly 260 can be controlled such that rotation of the carousel 261 and container 12 continues, and detection of the timing mark 462 results in the activation of the print head assembly 150 while the carousel 261 continues to rotate.

In step 466, with the print head assembly 152 activated, the rotation assembly 260 is activated to effect rotation of the container 12 and movement of the curved surface with respect to the activated print head assembly 150. In one embodiment, the motor 300 is activated for a specified number of counts or steps, thereby effecting the correct angular relative movement between the curved surface of the article 12 and the print head assembly 152 so as to apply the desired image to the curved surface.

Further details regarding an exemplary printing process are described below. In an embodiment described below, a timing mark modifier, which may be an extension of or other detectable alteration of the timing mark or which may be a secondary timing mark, is printed during the printing process to provide an indication that the tube has been printed on. Detection of such a timing mark modifier by the timing mark sensor 310 indicates that the tube has been previously printed on and may result in the tube being rejected for further processing.

In step 468, after step 466 is completed, the motor 300 is deactivated to halt rotation of the carousel 261, and the print head assembly 152 is deactivated to terminate printing onto the curved surface.

In step 470, the bracket expander 220 is activated to rotate the shaft 222 and the cam disc 226 and open the expandable printing mechanism 50 to the open configuration so that the article, e.g., container 12, can be removed from the printing module 10. In the reverse of the operation previously described, the bracket expander 220 can be activated and controlled by sending a control and power signal to motor 248 to operate the motor for a specified number of steps to rotate the cam disc 226 from a second position corresponding to the closed configuration of the expandable printing mechanism 50, i.e., a position in which the portions 230 of the cam disc 226 are in contact with the roller bracket 52 and print head bracket 100, to a first position corresponding to the opened configuration of the expandable printing mechanism 50, i.e., a position in which portions 228 of the cam disc 226 are in contact with the roller bracket 52 and the print head bracket 100. Again, optical sensor 238 can be monitored by the controller 400 to confirm that the shaft 222 and cam disc 226 have rotated to the proper position for the opened configuration of the expandable printing mechanism 50. Alternatively, or in addition, the motor 248 can be activated by sending power to the motor 248 to rotate the shaft 222 and the cam disc 226 until the slotted optical sensor 238 indicates that the cam disc 226 has rotated from the second position corresponding to the closed configuration of the expandable printing mechanism 50 to the first position corresponding to the opened configuration of the expandable printing mechanism 50, at which time power to the motor 248 is terminated.

In step 472, the motor 300 is activated to operate in reverse to cause reverse rotation of the carousel 261 and the lower disc 262 and withdraw the knurled wheels 284 radially away from the container 12.

As the article, e.g., tube 12, is rotated by the article moving assembly 260 while the article is being pressed against the print head 152 by the rollers 72 (or 72') and 74, it is possible that the tube 12 may slip within the knurled wheels 284 of the pivoting gripper assemblies 280. If the tube slips, the carousel 261 may rotate by a prescribed amount, but the tube 12 will have rotated less than the prescribed amount. As there should be relative movement between the print head 152 and the tube 12 as an image is applied to the curved surface of the tube 12 by the print head 152, slippage will interrupt that relative movement thereby leading to errors and inaccuracies in the image printed by the print head. Thus, in an embodiment described below, before step 472 is performed, a slip detection process may be performed to determine if the tube may have slipped within the knurled wheels 284 during the printing process.

In step 474, container 12 is removed from the module 10 through the access opening 30. The container or other article can be removed from the printing module 10 by any suitable means or mechanism, including manually or by a robotic pick-and-place mechanism.

Tubular Container

Figure 22:
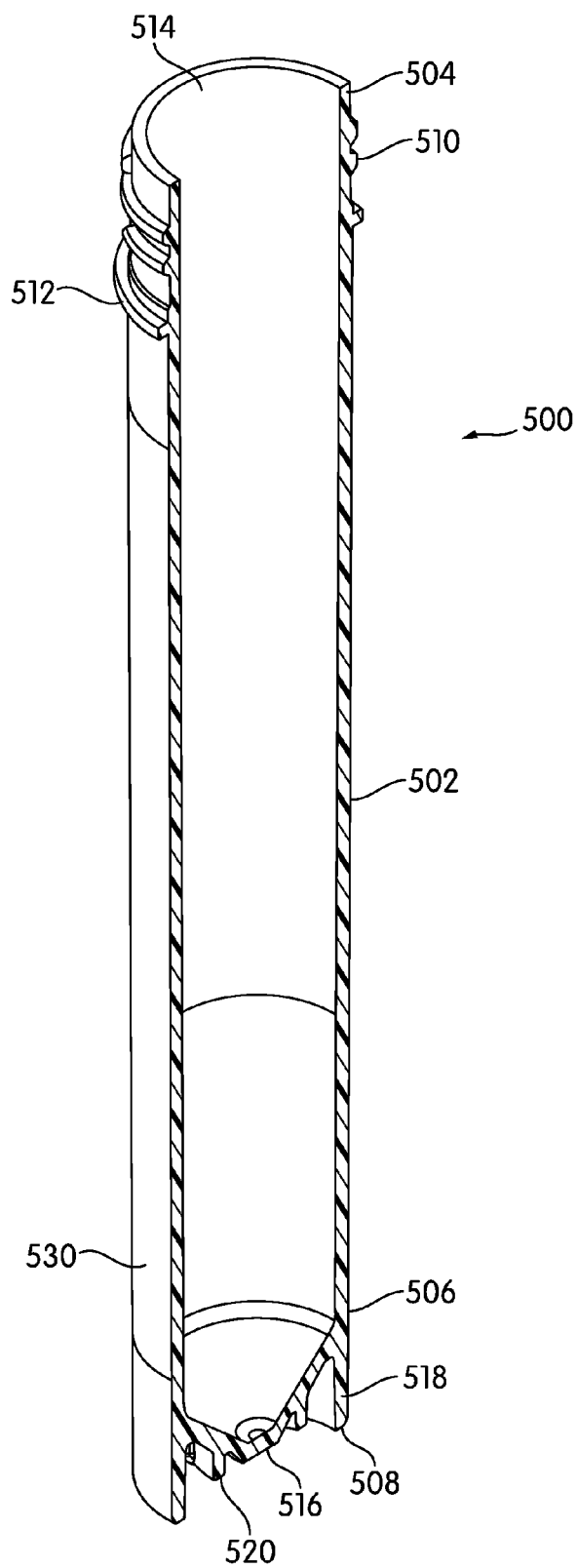
FIG. 22 is a perspective view in longitudinal cross-section of a container on which information can be printed on an external surface thereof by the printing module of the present disclosure.
Figure 23:
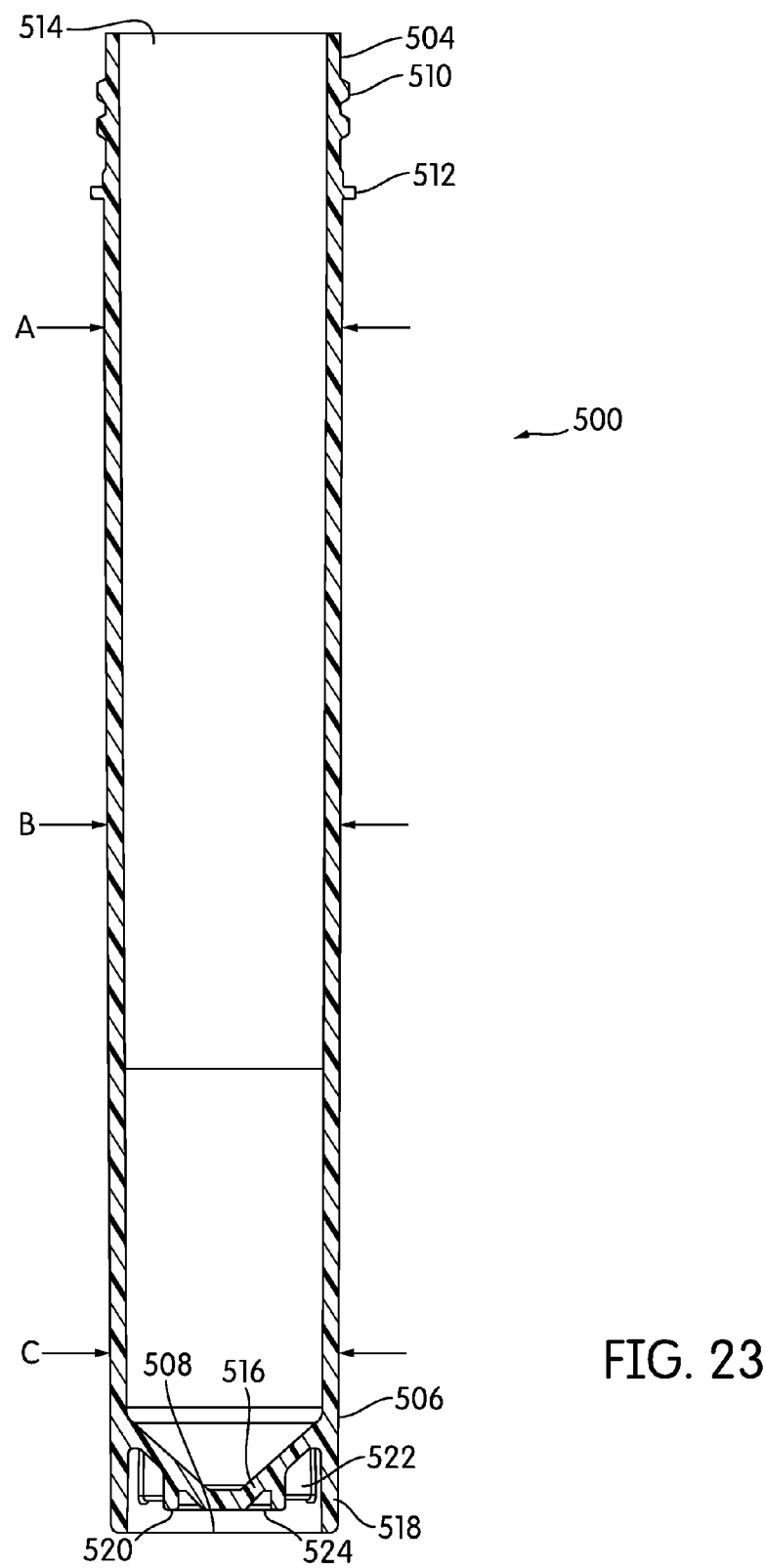
FIG. 23 is a side cross-sectional view of the container.
Figure 24:
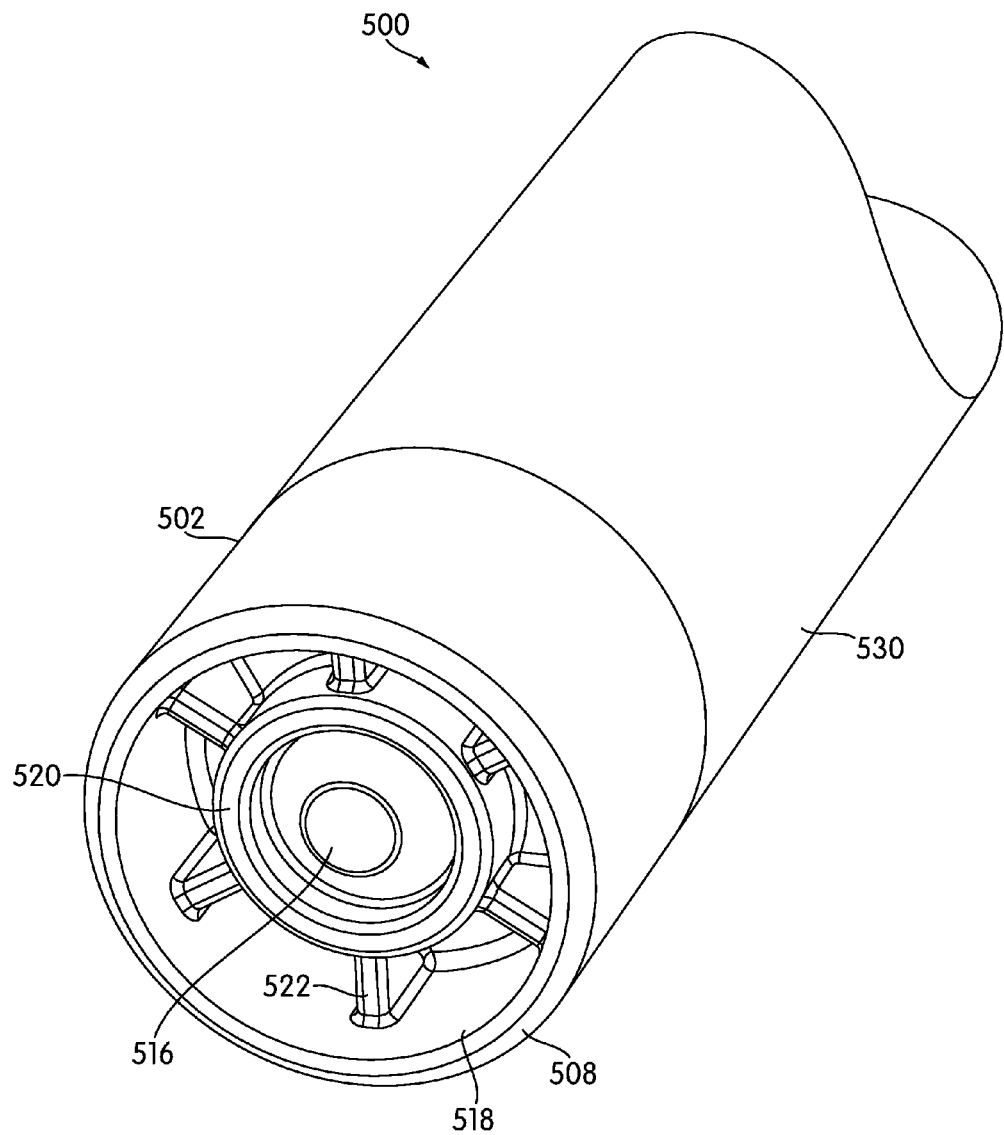
FIG. 24 is a bottom, perspective view of the container.

A specific embodiment of a container, e.g., container 12, for use in the printing module 10 is generally indicated by reference number 500 in FIGS. 22-25. FIG. 22 is a perspective view, in longitudinal cross-section, of the container 500, FIG. 23 is a side cross-sectional view of the container 500, FIG. 24 is a bottom, perspective view of the container 500, and FIG. 24 is a bottom plan view of the container 500.

The container 500 is a generally tubular container having a sidewall 502 with an exterior surface 530 and a generally circular opening 514 at an upper end 504 and a bottom wall 516 near the lower end 506 of the container. In the illustrated embodiment shown in FIGS. 22 and 23, the bottom wall 516 has a frustoconical shape. Exterior surface 530 may include a label made from, e.g., a thermal print medium, secured to the exterior surface of the side wall 502 by adhesive or the like.

The container 500 can be made of any suitable material, and is preferably made from an injection molded plastic, such as polypropylene, or other similar material. The material of which the container 500 is made preferably has sufficient strength and pliability to withstand the forces applied to the sidewall 502 by the print head assembly 150 as well as rollers 72 and 74 without breaking or permanently deforming the container 12.

The container 500 may be configured to hold chemical and/or biological sample material, including biological samples commonly collected and delivered to clinical laboratories for analysis, such as blood, urine, sputum, saliva, pus, mucous and cerebrospinal fluid and/or chemical and/or biological process materials, such as chemical compounds or reagents that react with the sample material and/or each other within the container 500.

Container 500 may be configured at its upper end 504 to cooperatively receive a cap or other closure element for temporarily or permanently closing off the upper opening 514 of the container 500. Features provided for cooperating with a cap may include threads 510 formed on an exterior surface of the sidewall 502 of the container 500 and configured to cooperate with mating threads formed on an interior surface of a cap. Alternatively, threads may be formed on the interior surface of the sidewall 502 and configured to cooperate with mating threads formed on an exterior surface of the cap. Other features for securing a cap to the container 500 may include cooperating flanges, recesses, and/or tabs that allow the cap to snapped into place on the container.

A ring flange 512 extending circumferentially about the sidewall 502 of the container 500 can be included to be abutted by a bottom, annular edge of a cap side wall when the cap is placed on the upper end of the container 500.

Suitable caps for use with the container 500 include penetrable caps described by Kacian et al. in U.S. Pat. No. 6,893,612.

An axially depending skirt 518 extends from the side wall 502 below the bottom wall 516 at the lower end 506 of the container 500. In the illustrated embodiment, the depending skirt 518 comprises an axial extension of the sidewall 502 below the frustoconical bottom wall 516. A lower end of the skirt 518 defines an edge ring 508 that is generally perpendicular to a longitudinal axis of the container 500, so as to define a bottom edge upon which the container can be set in an upright position on a flat surface, such as a table or counter top. The skirt 518 also provides a surface at the bottom of the tubular container 500 to be contacted by the knurled wheels 284 of the container rotation assembly 260.

In the illustrated embodiment, circular intermediate skirt 520 surrounds the frustoconical bottom wall 516 and extends below an exterior surface of the bottom wall 516 in a configuration that is generally concentric with the axially depending skirt 518. A lower end 524 of the intermediate skirt 520 is generally perpendicular to the longitudinal axis of the container 500 and, in the illustrated embodiment, is co-terminal with the tip of the frustoconical bottom wall 516.

Figure 25:
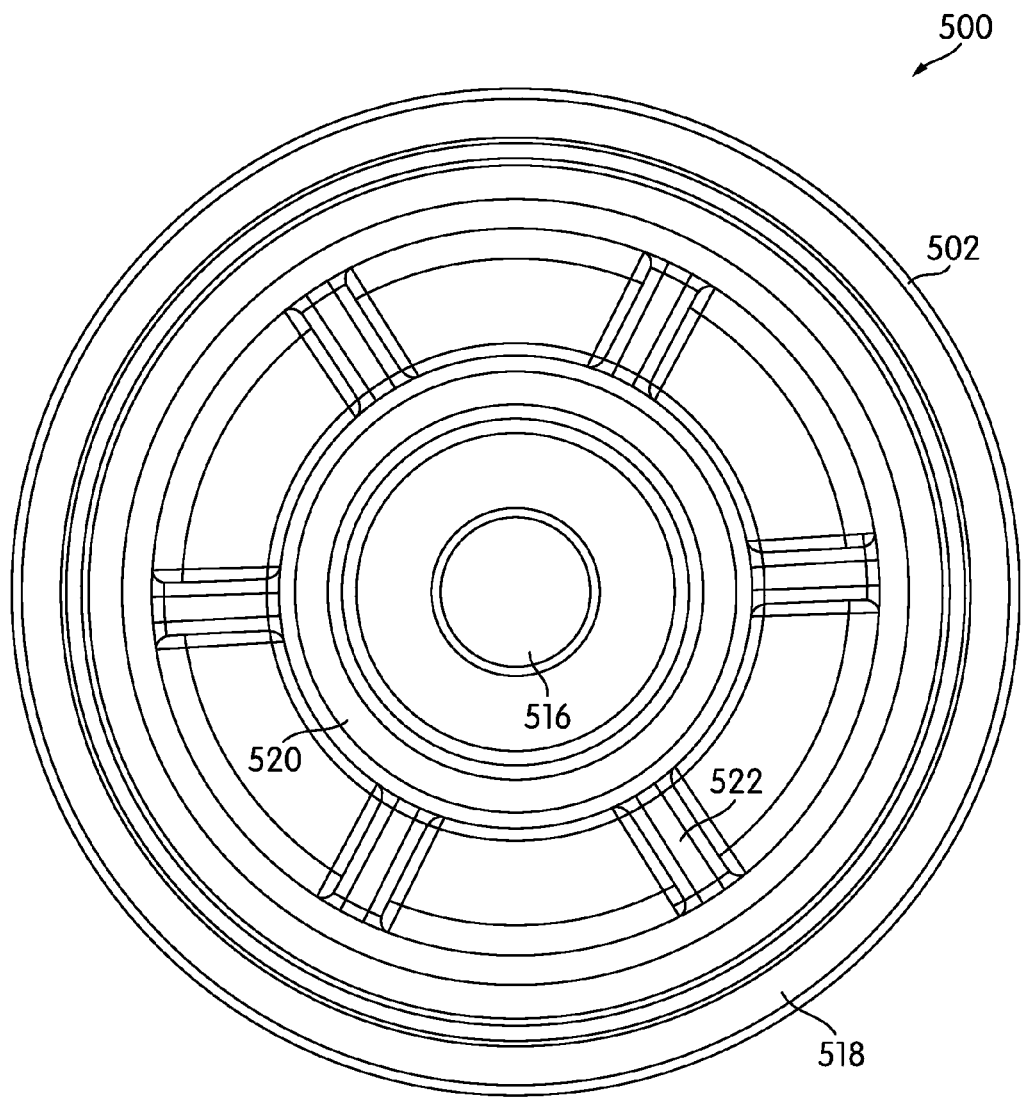
FIG. 25 is a bottom plan view of the container.

As shown in FIGS. 23-25, a plurality of radially oriented spoke ribs 522 extend between the intermediate skirt 520 and the axially depending skirt 518. The illustrated embodiment includes six radial spoke ribs 522. The spoke ribs 522 may be equiangularly-spaced, as shown, and each spoke rib 522 extends radially between the skirts 518 and 520 and extends axially from the outer surface of the frustoconical bottom wall 516 to a terminal edge that is above the lower edge 524 of the intermediate skirt 520.

In one embodiment, the container 500 may have a tubular, e.g., cylindrical, configuration with a generally constant diameter from the upper end 504 to the lower end 506. In another embodiment the diameter of the sidewall 502 of the container 500 may vary along the axial length of the container 500. For example, as shown in FIG. 23, the sidewall 502 may be defined by a diameter "A" near the upper end 504 of the container, a diameter "B" at an axial midpoint of the sidewall 502, and a diameter "C" near the lower end 506 of the container 500. In one embodiment, the sidewall 502 has a convex shape in which the diameter B is greater than the diameter C and the diameter A. Diameters A and C may be roughly equal. The diameter of the container 500 may vary continuously, e.g., linearly, from diameter A to diameter B to diameter C. The convex outer shape of the sidewall 502 of the container 500 can facilitate sufficient contact between the surface 530 and a print head, such as print head assembly 152, of the printing module 10, especially when combined with a convex contact element, such as convex roller 72, for pressing the external surface of the side wall 502 into contact with the print head 152. The container 500 may also be formed from a material that is somewhat pliable, so that as the convex side wall 502 is pressed against the print head assembly 150 by the rollers 72, 74, the sidewall 502 will flex into substantially uninterrupted contact between the sidewall 502 and the print head assembly 150 so as to compensate for slight dimensional irregularities or tolerances that may be inherent in the process for manufacturing the container 500.

Figure 26:
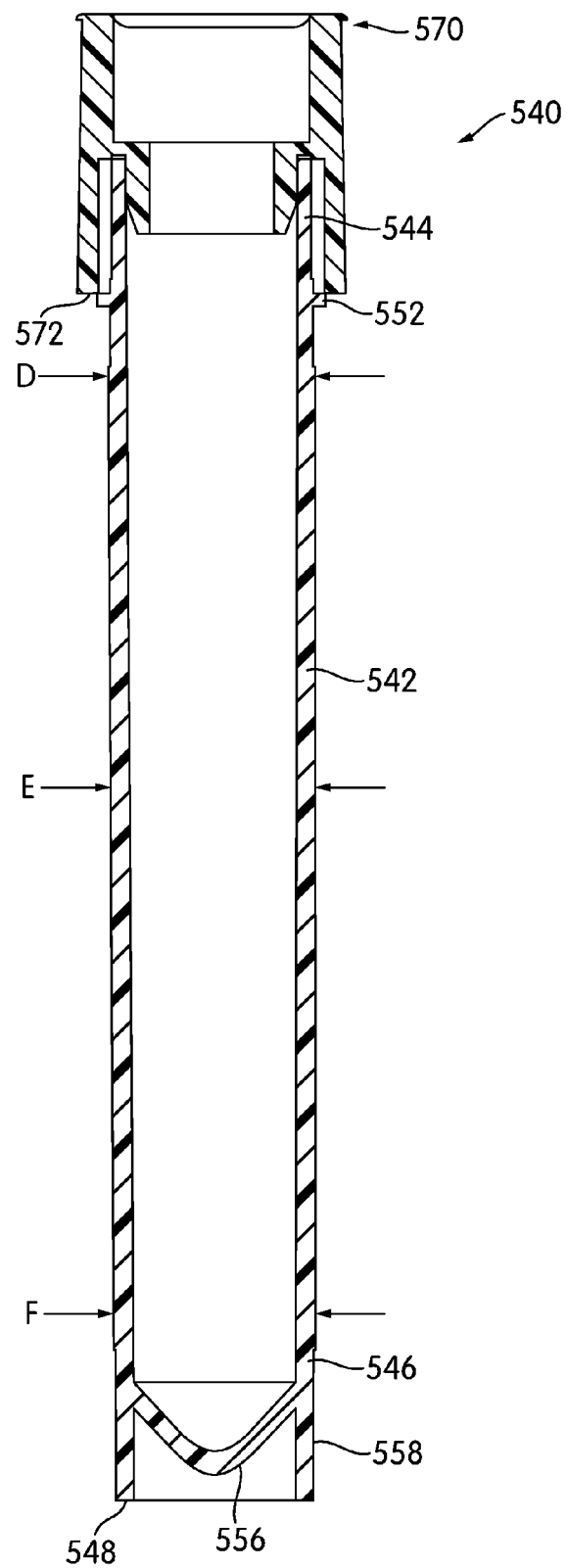
FIG. 26 is a side view in longitudinal cross-section of an alternative embodiment of a container and further including a cap.

An alternative specific embodiment of a container for use in the printing module 10 is generally indicated by reference number 540 in FIG. 26. FIG. 26 is a side cross-sectional view of the container 540. As with container 500, container 540 is a generally tubular container having a sidewall 542 with a generally circular opening at an upper end 544 and a bottom wall 556 near the lower end 546 of the container. In the illustrated embodiment of FIG. 26, the bottom wall 556 has a conical shape. Side wall 542 may include a label (not labeled in FIG. 26) made from, e.g., a thermal print medium, secured to the exterior surface of the side wall 542 by adhesive or the like.

The container 540 can be made of any suitable material, and is preferably made from an injection molded plastic, such as polypropylene, or other similar material.

Container 540 may be configured at its upper end 544 to cooperatively receive a cap 570 or other closure element for temporarily or permanently closing off the upper opening of the container 540. Features provided for cooperating with a cap, such as cap 570, include external threads that cooperate with mating internal threads of the cap 570. Again, as an alternative, threads may be formed on the interior surface of the sidewall 542 and configured to cooperate with mating threads formed on an exterior surface of the cap, or cooperating flanges, recesses, and/or tabs may be provided to allow the cap 570 to snapped into place on the container 540.

A ring flange 552 extending circumferentially about the sidewall 542 of the container 540 is abutted by a bottom edge 572 of the cap 570. Suitable caps for use with the container 540 include a penetrable cap described Kacian et al. in U.S. Pat. No. 6,893,612.

An axially depending skirt 558 extends from the side wall 542 below the conical bottom wall 556 at the lower end 546 of the container 540. In the illustrated embodiment, the depending skirt 558 comprises an axial extension of the sidewall 542 below the conical bottom wall 546. A lower end of the skirt 558 defines an annular edge ring 548 that is generally perpendicular to a longitudinal axis of the container 540, so as to define a bottom edge upon which the container can be set in an upright position on a flat surface, such as a table or counter top.

The container 540 may have a tubular, e.g., cylindrical, configuration with a generally constant diameter from the upper end 544 to the lower end 546. In another embodiment, however, the diameter of the sidewall 542 of the container 540 may vary along the axial length of the container 540. For example, as shown in FIG. 26 the sidewall 542 may be defined by a diameter "D" near the upper end 544 of the container, a diameter "E" at an axial midpoint of the sidewall 542, and a diameter "F" near the lower end 546 of the container 540. In one embodiment, the sidewall 542 has a convex shape in which the diameter E is greater than the diameter D and the diameter F. Diameters D and F may be roughly equal. The diameter of the container 540 may vary continuously, e.g., linearly, from diameter D to diameter E to diameter F.

Sample Processing Instrument

Figure 27:
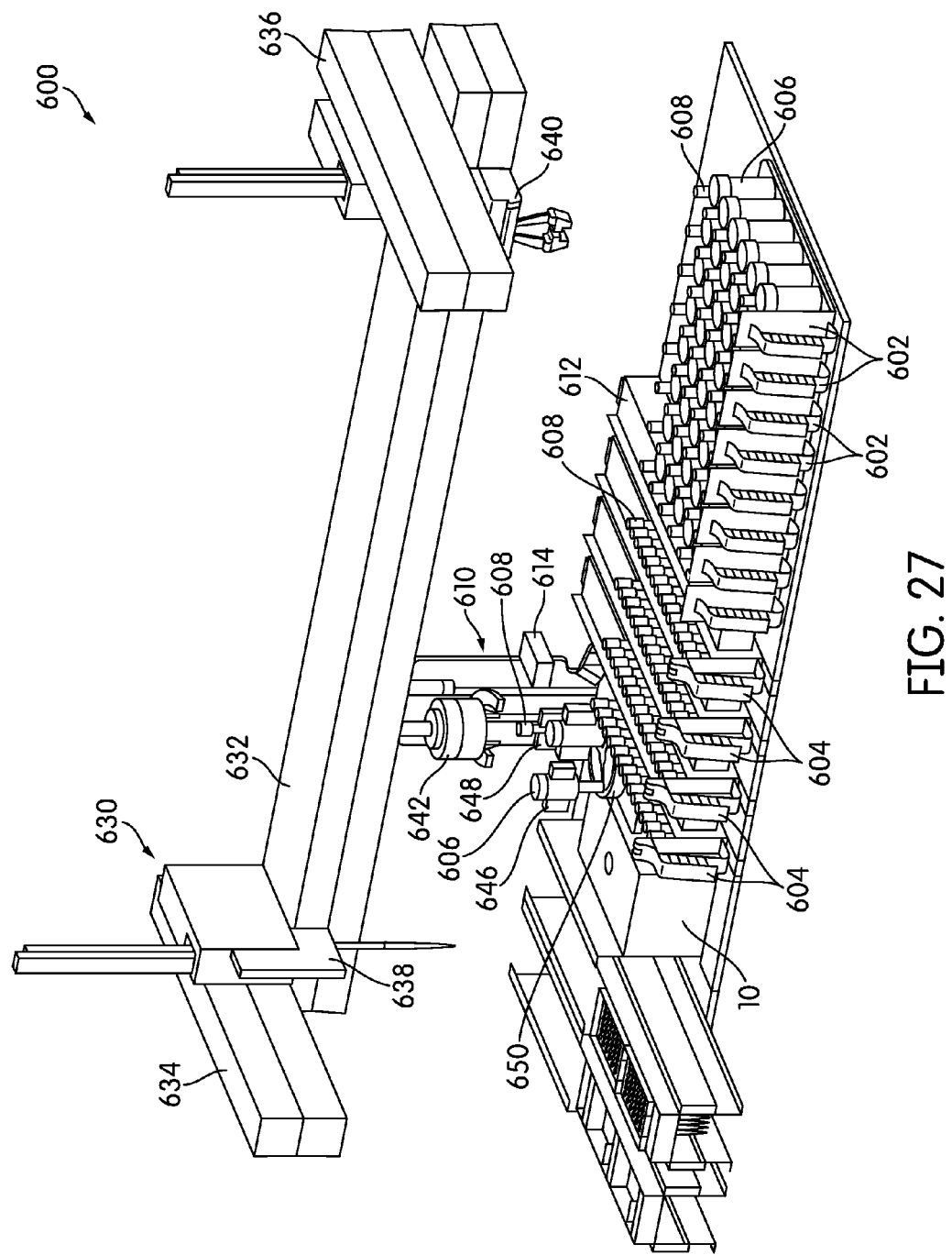
FIG. 27 is a perspective view of a sample processing instrument in which the printing module may be incorporated.

The tube printing module 10 may be incorporated in a sample processing instrument, such as an automated instrument for transferring materials from one container to another. An exemplary instrument is described in U.S. Patent Application Publication No. 2013-0065797, "Automated Sample Handling Instrumentation, Systems, Processes, and Method." Referring to FIG. 27, an automated instrument 600 of the type in which the printing module 10 may be incorporated includes one or more input racks 602, one or more output racks 604, a robotic arm 630, a sample processing station 610, a sample transfer apparatus, such as a sample pipettor 638 or other substance transfer device, a robotic pick-and-place mechanism, such as a container gripper 640, and one or more incubators 612. In one embodiment, the sample transfer apparatus comprises a Cavro® Air Displacement Pipettor available from Tecan Group Ltd. Männedorf, Switzerland. Each input rack 602 carries a plurality of first sample containers 606, which may comprise capped sample vials, and a plurality of second sample containers 608, which may comprise capped sample tubes, for example in a one-to-one arrangement. Each output rack 604 is configured to hold a plurality of second sample containers 608, each after an amount of sample material is transferred from a first sample container 606 to the second sample container 608 and, optionally, after transferring one or more other material(s), e.g., reagents, probes, buffers, etc., to the second sample container and/or incubating the contents of the second sample container 608.

Each of these components may be located within an instrument housing.

In one embodiment, the instrument 600 is configured to move first sample containers 606 and second sample containers 608 between the input racks 602, the sample processing station 610, and the output racks 604. As described in U.S. Patent Application Publication No. 2013-0065797, the sample processing station 610 is configured to receive and hold a first sample container 606, automatically remove a lid from the first sample container 606, position the opened first sample container 606 so that an aliquot of sample material can be aspirated from the first sample container 606, replace the cap onto the first sample container 606, receive and grasp a second sample container 608, automatically remove a lid from the second sample container 608, position the opened second sample container 608 so that all or a portion of the aliquot of sample material removed from the first sample container 606 can be dispensed into the second sample container 608, and replace the lid onto the second sample container 608.

In an embodiment, the sample pipettor 638 transfers specimens from first sample containers 606, such as liquid based cytology (LBC) specimen containers, to second sample containers 608 (e.g., Aptima® transport tubes available from Hologic, Inc., San Diego, Calif.) while also performing liquid level detection and reagent dispensing. The sample processing station 610 preferably is also configured to hold the first sample containers 606 and second sample containers 608, perform barcode reading, barcode positioning, and specimen mixing, in addition to uncapping/recapping of the first sample container 606 and second sample container 608. The incubator(s) 612 may be incorporated into the instrument 600 and may be, such as in the depicted embodiment, adapted to hold one or more sample output racks 604 and utilized to incubate sample directly within the second sample container(s) 608 held in the output rack(s) 604. LBC samples, such as samples collected in SurePath® vials (Becton Dickinson, Inc., Franklin Lakes, N.J.), often require reagent addition and heated incubation prior to further processing, such as a molecular assay. Other LBC sample types, such as those collected in ThinPrep® vials (Hologic, Inc., Bedford, Mass.), often do not require incubation.

More particularly, the sample processing station 610 may include a turntable 650 on which are mounted container holders 644, 646, 648 configured to hold individual first sample containers 606 or second sample containers 608. The sample processing station 610 may be configured so that the turntable 650 may rotate to selectively position a first sample container 606 or second sample container 608. The turntable 650 and the container holders 644, 646, 648 may rotate simultaneously about respective axes of rotation to effect mixing of the contents of the first sample containers 606 and/or second sample containers 608 carried in the container holders. The sample processing station 610 may further include a capping/decapping mechanism 642 configured to selectively uncap or recap a first sample container 606 or second sample container 608 carried on the turntable 650. The sample processing station further includes a mechanism to effect relative movement between a container and the capping/decapping mechanism 642 to enable the mechanism 642 to engage the cap of a first sample container or second sample container. After engaging, e.g., gripping or clamping, the cap, the capping/decapping mechanism rotates to remove the threaded cap from the first sample container or second sample container or replace a previously-removed threaded cap onto the first sample container or second sample container.

In one embodiment, specimens are tracked within the instrument 600 by providing matching barcodes on both the first sample container 606 and the second sample container 608. For example, an onboard barcode scanner 614, or other code-reading device, reads the tube barcodes, or other machine-readable codes, once each tube is placed in the sample processing station 610. System process controls, tube barcodes, time/date stamps, user information, and system status are frequently stored in an onboard tracking system that may be queried via a barcode on the first sample container 606 and/or the second sample container 608. In various embodiments, a user can manually enter an identifier associated with the barcode by use of a keyboard or keypad, an instrument touch screen, or through the use of an optional handheld barcode scanner to perform such a query. The system software can be adapted to monitor the overall system status, reagent and supply inventories, processed specimen records, and maintenance.

In one embodiment, the robotic arm 630 is translatable in mutually orthogonal X, Y, and Z directions to move first sample containers 606 and second sample containers 608 between modules in the instrument 600 (e.g., between the sample processing station 610, the input rack(s) 602, the output rack(s) 604, and the printing module 10). In one embodiment, such as that depicted in FIG. 27, the robotic arm 630 includes a first arm 632 extending in a longitudinal, side-to-side orientation and two or more robotic arms 634, 636 carried on the first arm 632 and extending in a lateral, front-to-back orientation with respect to the first arm 632. In an embodiment, arms 634, 636 are configured for powered translation in a longitudinal (X-axis) direction along the first arm 632, actuated, for example, by a motorized belt and pulley arrangement, rack and pinion, or threaded rod. In the illustrated embodiment, the robotic arm 634 includes the sample pipettor 638, and the robotic arm 636 includes a container gripper 640. The sample pipettor 638 is configured for powered translation in a lateral direction (Y-axis) along the robotic arm 634, and the container gripper 640 is configured for powered translation in a lateral direction (Y-axis) along the robotic arm 636, each actuated, for example, by a motorized belt and pulley arrangement, rack and pinion, or threaded rod. The sample pipettor 638 and the container gripper 640 is each configured for powered movement in a vertical direction (Z-axis), actuated, for example, by a motorized rack and pinion or threaded rod.

Motors employed for powered movement of components of the robotic arm 630 in the X, Y, and Z directions may comprise independently-controllable stepper motors and may include rotary encoders. Home and/or limit sensors may be employed along each axis to detect movement to a specified home and/or limit position, respectively.

In a preferred embodiment, the sample pipettor 638 of the robotic arm 630 incorporates an air-based pipettor system to aspirate sample material from first sample containers 606 and dispense samples and reagents into second sample containers 608.

In alternate embodiments, the sample pipettor 638 and container gripper 640 are incorporated on the same robotic arm (e.g., a signal, laterally-extending robotic arm), but each is independently operable in the Y-axis and Z-axis directions.

One example of a contemplated sample pipettor 638 is a fully-integrated OEM module (e.g., such as that available from Tecan Group Ltd., Männedorf, Switzerland) capable of dispensing volumes from 10-1000 µL with a CV of 0.75%. In a preferred embodiment the pipettor is compatible with Tecan disposable tips (e.g., 10 µl, 50 µl, 200 µl, 1000 µl, with or without filter), and is an air-based-pipettor that does not require tubing, valves, or syringes. The pipettor head frequently contains advanced on-board pump diagnostics, self-test, and error reporting. Moreover, a preferred pipettor has configurable liquid level detection with an integrated pressure sensor (pLLD), is compatible with external capacitive liquid level detection hardware (cLLD), can provide real time streaming data from one or more pressure sensor(s) for process monitoring, and has a DiTi (disposable tip) presence sensor and DiTi ejection mechanism.

The container gripper module 640 is configured to pick-and-place first sample containers 606 and second sample containers 608 within the instrument 600. The container gripper module 640 may employ a chuck or caliper mounted on a movable boom for movement in the Z direction and configured to selectively open and close to grasp and release either a first sample container 606 or a second sample container 608. In one embodiment, the gripper mechanism 640 employs a cam disk that opens and closes the gripper when rotated CW/CCW. In an embodiment, the cam disk is optionally driven by a small high torque DC gear motor or stepper motor. A variety of additional gripper mechanisms are also contemplated and known in the art.

As explained above, ensuring sample identification accuracy is another problem encountered when automating a sample handling process. For example, as a sample is prepared, an aliquot of sample material is transferred from the first sample container 606 to the second sample container 608 by the sample pipettor 638. Therefore, it is important to ensure that the sample in the second sample container 608 is accurately correlated with the sample in the first sample container 606 so that the sample is processed according to the proper protocol and that the correlation of that sample with the sample source, e.g., the donor patient, is maintained. To address these issues the instrument 600 advantageously tracks the identification of each sample throughout processing, including following the sample as it is transferred from the first sample container 606 to the second sample container 608. One exemplary method of tracking this information provided herein is to utilize barcodes on both the first sample container 606 and the second sample container 608. This process maintains sample-to-result positive identification tracking.

The instrument 600 may also incorporate a controller, which may communicate with and/or be part of the controller 400 of the printing module 10 described above. The instrument controller manages and processes system-wide activities by delegating, monitoring, and controlling specific tasks to instrument sub-components or modules. Exemplary system activities include capping/decapping sample and second sample containers, vortexing (i.e., mixing), pick-and-place of sample and second sample containers, pipetting, waste reservoir monitoring, monitoring consumable (e.g., pipette tip) inventory, monitoring sample queues, maintaining run logs, monitoring process controls, monitoring system alarms, etc.

In one embodiment, the laboratory workflow for processing samples, such as LBC samples, requires that both the first sample container 606 and the second sample container 608 have a barcode containing sample identification information. This requires that the first sample container 606 and second sample container 608 have barcodes that are identical, at least partially identical, or otherwise correlated so that independently-trackable sample identification information is encoded in both barcodes. This enables downstream analytical instruments, such as instruments capable of performing sample processing (e.g., isolation and purification of targeted molecules), hybridization assays, amplification procedures, sequencing reactions, and/or immunoassays to communicate with the laboratory's LIS via the barcoded information provided on the second sample container 608.

In this context, barcodes are identical if the same data, e.g., the same alphanumeric sequence, is encoded into each barcode. In various embodiments, barcodes that are of different formats, e.g., 1-D versus 2D, may be consider identical if each has the same data encoded into the barcode. Barcodes are partially identical if some, but not all, of the same data is encoded into each barcode.

In one embodiment, a barcode containing or associated with sample-identifying information is applied to the first sample container 606. The second sample container 608, in turn, contains no label, a blank label, or a different label. A first sample container 606 is moved by the robotic arm 630 and container gripper 640 from an input rack 602 to the sample processing station 610 to be processed. In addition, a corresponding second sample container 608 is transferred from the input rack 602 to the printing module 10 by the robotic arm 630 and container gripper 640. The instrument 600 then reads barcode on the first sample container 606, for example with the barcode reader 614 in the sample processing station 610. After reading the first sample container barcode, the instrument 600 creates a corresponding barcode (with optional additional metadata in the form of barcode prefixes, suffixes, etc.) directly on the second sample container 608 with the printing module 10. In some embodiments, a different, additional barcode or other human and/or machine-readable information is printed on the second sample container 608 containing additional metadata (e.g., time, volume, type, reagents, error codes, processing information (for example, tests or process to be performed or that have been performed), test results, etc.) related to the processing of the corresponding sample. As will be described in further detail below, the printer may also print a code or graphic feature indicating that the second sample container has been "used," and the printer may include a sensor, such as the timing mark sensor 310, configured to detect this "vessel-used" mark. After the barcode is printed onto the second sample container 608, the second sample container 608 is transferred by the robotic arm 630 and container gripper 640 from the printing module 10 to an output rack 604.

In an alternative application of the printing module 10 as disclosed herein, containers having curved surfaces can be passed between two or more stations (processing modules) of a process system on a conveyor system. One or more of the stations may include a printing module 10 to print process data to the tube—human and/or machine readable—with subsequent stations printing additional process data as the container traverses the process system. Thus, in one embodiment, the entire history of the container can be printed on the container, results, error codes, process control data, aliquoting data, time-date stamps, next process station to be routed to, material (e.g., patient) ID, lab address, etc.

Sample Processing Workflow

Figure 28:
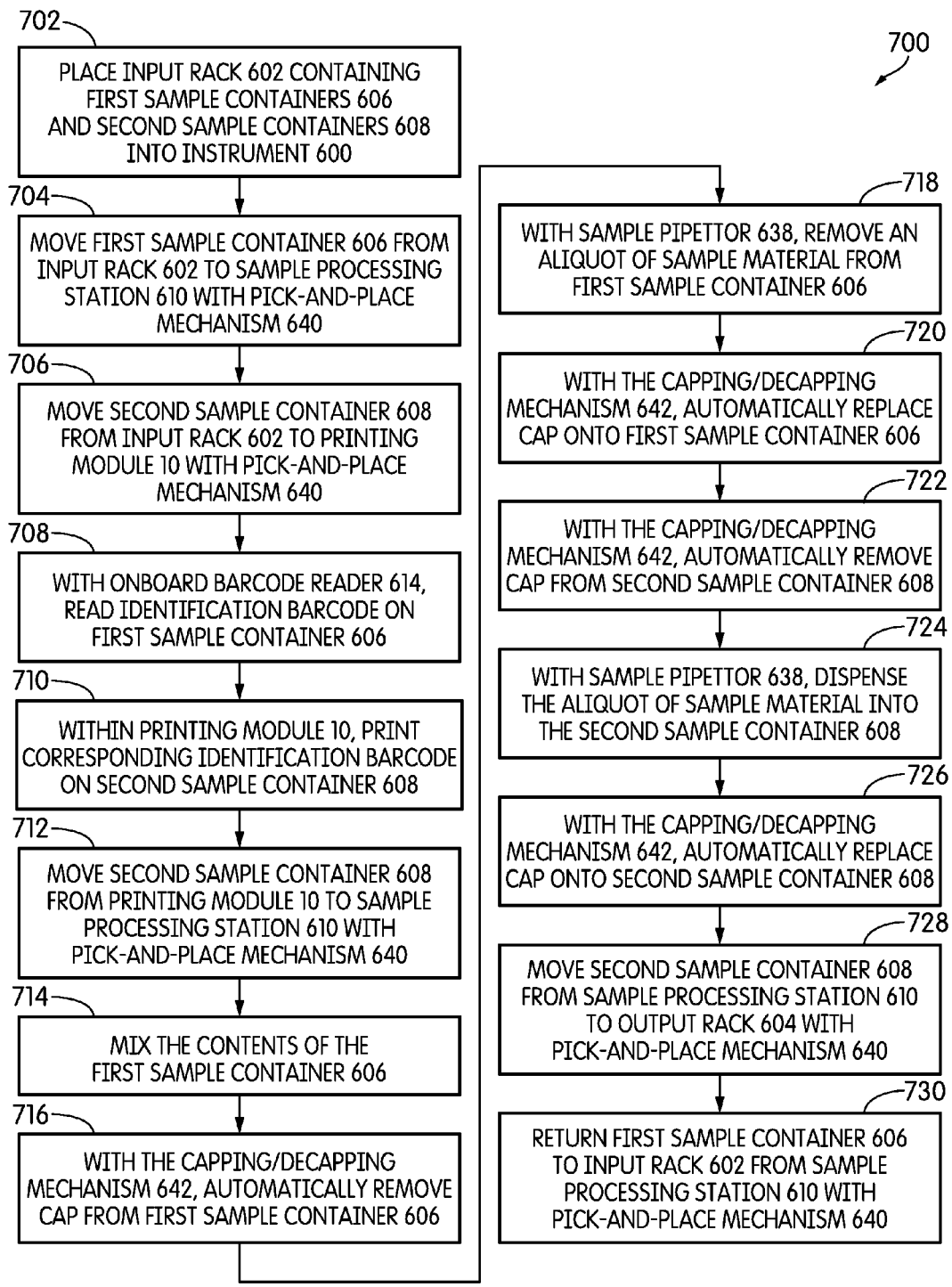
FIG. 28 is a flow chart showing a work flow for processing a sample with the sample processing instrument.

FIG. 28 is a flow chart showing a work flow 700 for processing a first sample container and a second sample container in an instrument, such as instrument 600, which employs a printing module 10.

In step 702, an input rack 602 containing first sample containers 606 and second sample containers 608 is placed into an appropriate slot or other receptacle within the instrument 600. Typically, each first sample container 606 will have labels with machine-readable, identifying indicia, such as barcodes, and may also include human-readable labels. The second sample containers 608 will contain blank or partially blank labels. Furthermore, each first sample container 606 and each second sample container 608 will typically be capped by a screw-on threaded cap. In one implementation the first sample containers 606 and second sample containers 608 will be provided in a one-to-one configuration, meaning that the number of first sample containers 606 and the number of second sample containers 608 on the input rack 602 will be the same.

In step 704, a first sample container 606 is moved from the input rack 602 to the sample processing station 610 with the robotic pick-and-place mechanism 640.

In step 706, an empty second sample container 608 is moved from the input rack 602 to the printing module 10 with the robotic pick-and-place mechanism 640. Note that steps 704 and 706 can be performed in reverse order.

In step 708, which may occur before or after step 706, the machine-readable label on the first sample container 606 is read. For example, a barcode on the sample container 606 may be read by the on-board barcode reader 614. In an alternate embodiment, the barcode or other machine-readable label on the sample container 606 may be read before the sample container is moved to the sample processing station 610. The information encoded in or acquired from the machine-readable label on the sample container 606 is thereafter stored, for example in a storage media accessible to the instrument controller.

In step 710, the printing module 10 prints a machine-readable identification label on the second sample container 608 that was moved to the printing module in step 706. The machine-readable label may be a barcode corresponding to the barcode or other machine-readable label on the first sample container 606 and includes information based on the information that was acquired and stored from the machine-readable label on the first sample container 606. As explained above, in one embodiment, the machine-readable label printed onto the second sample container 608 may be a barcode that is identical to a barcode on the first sample container 606 and may have encoded therein an identification number, such as an accession number, of a patient from whom the sample was obtained.

In step 712, after the machine-readable label is printed onto the second sample container 608, the second sample container 608 is moved from the printing module 10 to the sample processing station 610 with the robotic pick-and-place mechanism 640.

In step 714, the contents of the first sample container 606 are mixed, for example by simultaneously rotating the turntable 650 and one of the container holder 644, 646, 648 holding the first sample container 602.

In step 716, a cap is automatically removed from the first sample container 606 using the capping/decapping mechanism 642.

In step 718, an aliquot of sample material is removed from the first sample container 606 using the sample pipettor 638.

In step 720, the cap is replaced onto the first sample container 606 using the capping/decapping mechanism 642.

In step 722, a cap is automatically removed from the second sample container 608 using the capping/decapping mechanism 642.

In step 724, the aliquot of sample material is dispensed into the second sample container 608 using the sample pipettor 638.

In step 726, the cap is replaced onto the second sample container 608 using the capping/decapping mechanism 642.

In step 728, the second sample container 608 is moved from the sample processing station 610 to an output rack 604 using the robotic pick-and-place mechanism 640. The output rack will have been previously placed in the instrument 600 in an appropriate slot or other receptacle, for example at the time of set up when one or more input rack holding first sample containers and second sample containers are placed in the instrument.

In an optional step, the second sample container may first be moved to an incubator where it remains for a predetermined dwell time or where all or some portion of the output rack 640 holding the second sample container 608 is incubated.

In step 730, the first sample container 606 is moved from the sample processing station 610 back to the input rack 602 using the robotic pick-and-place mechanism 640.

After all the first sample containers on the input rack have been processed and all second sample containers containing an aliquot of sample material are placed on an output rack, the output rack may be removed from the instrument 600 for further processing of the contents of each second sample container.

Printer Label and Timing Mark

Figure 29:
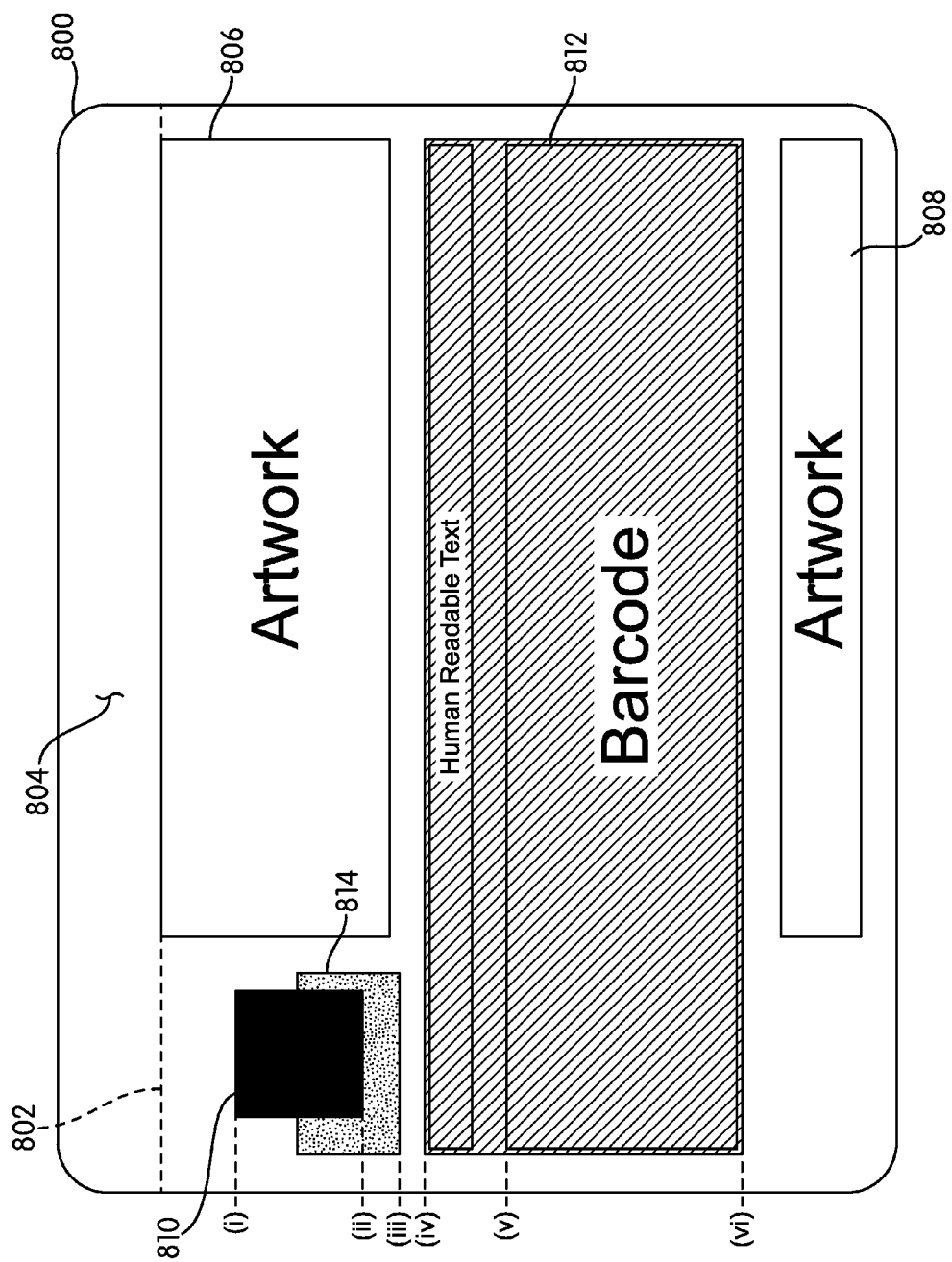

An embodiment of a tube printer label configured to be placed on the surface 14 of a tube 12 is indicated by reference number 800 in FIG. 29. Label 800 may comprise a paper label, such as thermal print paper, secured to the tube 12 by an adhesive such that line 802 is generally parallel to the longitudinal axis of the tube. The label may extend completely around the tube, with line 802 defining an area 804 that is overlapped by the label. Alternatively, label 800 may be printed on or otherwise integrally formed on a surface of the tube.

Tube printer label 800 may include areas 806, 808, which include pre-printed text and/or graphic labeling (e.g., "Artwork"), a pre-printed timing mark 810 extending between ends (i) and (ii), a printable area 812 between a leading edge or image position (iv) starting at a predefined distance from the timing mark 810 and ending at a trailing edge (vi) on which text and/or graphic indicia, such as a barcode or other machine-readable indicia, are printed by the printing module 10, and a timing mark modifier 814 that is printed onto the label 800 by the printing module 10 as an indicator for later detection that the tube has been previously printed on. In the illustrated embodiment, the timing mark modifier 814 is an extension that increases at least one dimension, e.g. length, of the timing mark 810. In other embodiments, the timing mark modifier decreases at least one dimension of the timing mark 810, such as length. In still other embodiments, the timing mark modifier does not directly alter the timing mark, but instead is an additional, discrete mark that is printed onto the label 800 by the printing module 10 as an indicator for later detection that the tube has been previously printed on. In an embodiment, the printable area 812 may have a portion dedicated to machine-readable indicia, such as the "Barcode" position between (v) and (vi). As shown in FIG. 29, the width of the timing mark modifier 814 in the horizontal direction in FIG. 29 (which corresponds to a vertical or longitudinal direction when the label is placed on an upright tube 12) is greater than the width of the timing mark 810. This is to account for manufacturing tolerances in the relative positions of the sensor 310 and/or the print head 152 and to ensure that some portion of the timing mark modifier 814 will be detected by the sensor 310.

Timing mark 810 and timing mark extension 814 are preferably readily detectable by the sensor 310. If the sensor 310 is a reflectance sensor and the label background is a light color (e.g., white), the timing mark 810 and the timing mark extension 814 are preferably solid, dark colors (e.g., black) so as to provide a clear, readily-detectable distinction between the marks and the background portions of the label.

Figure 30:
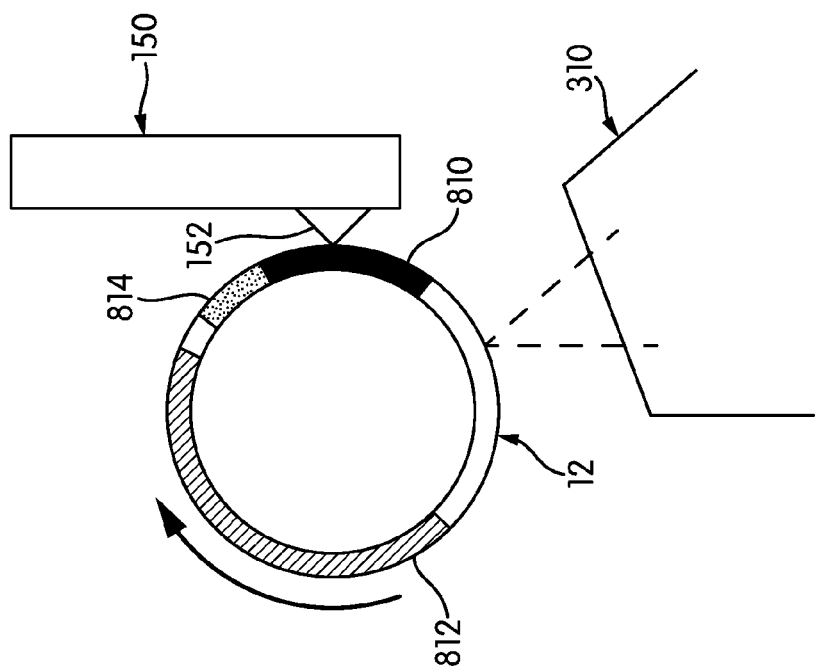
FIG. 30 is a schematic, top view of a timing mark sensor, a print head and a tubular container.

FIG. 30 shows the relative positions of the print head 152, the timing mark sensor 310, and the tube 12. In an embodiment, the rotation assembly 260 rotates the tube 12 clockwise, thereby placing the print head 152 rotationally ahead of the sensor 310 during printing and scanning. The positions of the timing mark 810, the timing mark modifier 814, and the printable area 812 on the tube 12 are shown. The remaining surface areas of the label 800 are typically not used during a normal print process.

In an embodiment, the sensor 310 is configured to measure the reflectance of the label 800 on a tube 12 that is currently positioned in front of the sensor 310. An unprinted (white) area generates a detectably higher sensor value (reflectance) compared to the pre-printed timing mark 810, and thus the controller 400 can detect from the output of the sensor when the timing mark 810 is passing in front of the sensor 310.

Figure 31:
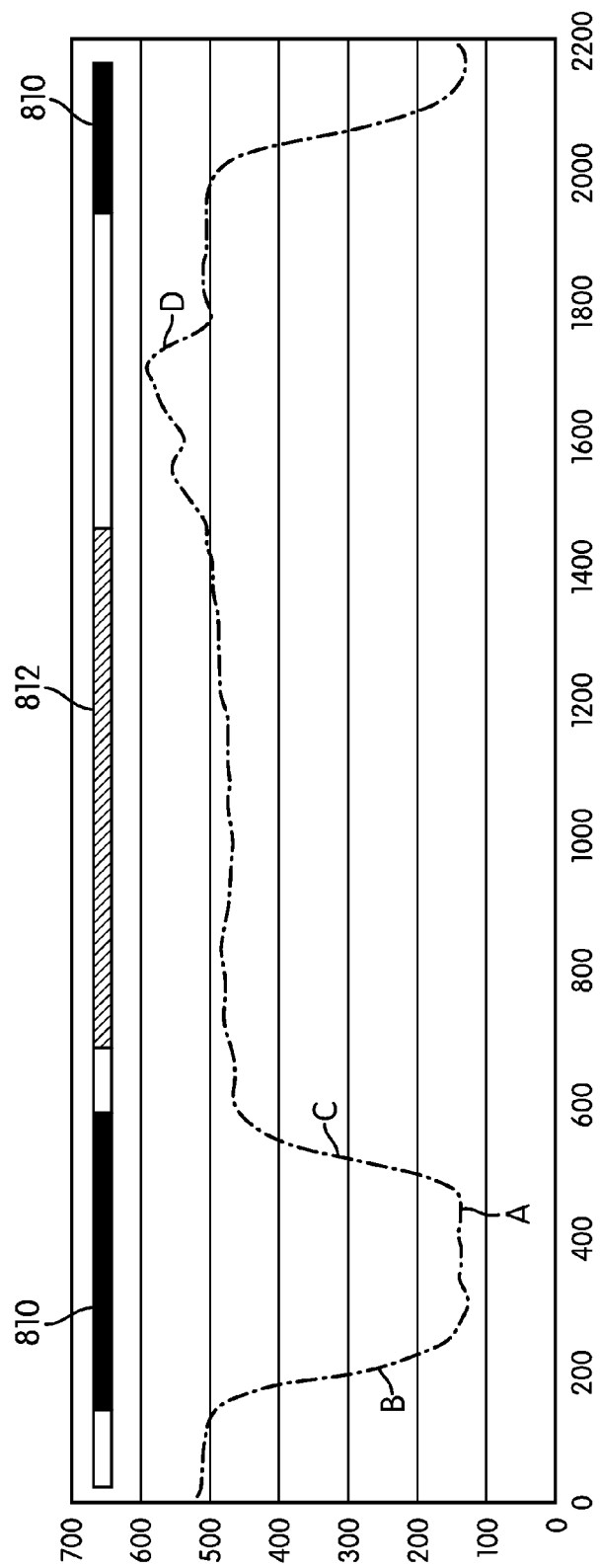
FIG. 31 is a plot of an exemplary waveform from the timing mark sensor as the label passes by the sensor over one revolution of the tube prior to any printing being applied on the label.

FIG. 31 shows an exemplary output waveform of the sensor 310 scanning a label 800—prior to printing any indicia onto the label—as a portion of the label 800 passes by the sensor 310. The waveform shown in FIG. 31 represents the output from the sensor 310, such as a plurality of sequentially recorded data points, over a little more than one revolution of the tube 12, and the locations of the timing mark 810 and the printable area 812 are shown in the bar plot above the waveform. Since this is a pre-print scan, the timing mark modifier 814 has not yet been printed on the label 800. In an embodiment, the output of the sensor 310 is in the form of discrete values recorded at specified intervals. For example, in one embodiment, the sensor is sampled (i.e., the sensor value is recorded) every half step of motor 300 during the rotation of the tube 12 by the container rotating assembly 260.

As shown, for example, in FIG. 12, the timing mark sensor 310 is located proximate a lower end of the tube 12 positioned within the printing module 10 (i.e., near the carousel 261). In an embodiment, the label 800 is applied to the outer surface of the tube 12 so that the left edge of the label 800 (as shown in FIG. 29) is proximate the lower end of the tube 12. Accordingly, the timing mark 810, the timing mark modifier 814 (when printed), and the left side (lower end) of the printable area 812 will pass in front of the sensor 310 and be detected during the rotation of the tube 12. Areas 806 and 808, which do not extend to the lower end of the label 800 (left side of label 800 in FIG. 29), will not pass before the sensor 310 and will not be detected.

Referring again to FIG. 31, the timing mark 810 can be seen at part A of the waveform between samples 200 and 500 (and again after sample 2000) where the reflectance measured by the sensor 310 drops appreciably due to the low reflectance of the timing mark 810. The leading and trailing edges of the timing mark 810 relative to the direction of rotation (points (i) and (ii) in FIG. 29) are represented by downslope portion B and upslope portion C, respectively, of the waveform. A bump D in the waveform between samples 1500 and 1800 is caused by the sensor 310 detecting an increase in reflectance adjacent the label edge.

The printing process begins with determining with the sensor 310 whether a tube 12 has been inserted into the printing module 10. In an embodiment, the determination of whether a tube is present in the printing module 10 is based on the value registered by the sensor 310. A sensor value that is lower than a specified threshold, which may be a predefined control parameter stored in memory 404, indicates that no tube is present, and a sensor value that is greater than or equal to the threshold indicates a tube is present. A specified tube-present, or print-surface-present, threshold can be determined empirically.

If a tube 12 is present within the module 10, the tube is then rotated by a full revolution by the container rotating assembly 260 to allow pivoting gripper assemblies 280 to fully engage the tube 12 and to urge the tube to settle into its correct position. A sensor luminance calibration may be performed during this first rotation to adjust the luminance of the sensor 310 to account for variations between different sensors and labels (e.g., darkness of the timing mark 810, shininess of the paper, etc.) and to account for degradation of sensor performance with age. In one embodiment, the calibration process starts with the sensor 310 set at a brightness level for which the sensor output is expected to be saturated, and then the tube is rotated. Upper and lower output limits of the sensor output waveform are predefined control parameters stored in memory 404. As the tube is rotated, the sensor brightness is reduced if the sensor output exceeds the predefined upper output limit of the tube sensor waveform (e.g., luminance value is decreased by 0.1% from the current value with each half step of the motor 300), or the sensor brightness is increased if the sensor output is less than the predefined lower output limit. The sensor brightness is set so that the sensor output is between the upper and lower output limits throughout the rotation of the tube 12.

In various embodiments incorporating a reflectance sensor for the sensor 310, the illumination source (e.g., an LED) of the sensor is energized only when needed and only with as much power as is necessary for a given operation.

The next step is to perform a seek start procedure to find the timing mark 810 on the label 800 and to rotate the tube 12 from the timing mark to a print start position.

The seek start procedure includes two steps. The first step is to find the position of the timing mark 810 and then determine at least one dimension of the timing mark, such as its circumferential length. The second step is to rotate the tube 12 to a print start position.

During the first step, the rotation assembly 260 rotates the tube 12, and the controller 400 monitors the output of the sensor 310 to locate falling and rising values within the sensor output waveform (sections B and C of the waveform shown in FIG. 31), marking the start and the end, respectively, of the timing mark 810 (and possibly the timing mark modifier 814, if present). The falling and rising edges of the sensor output waveform are located by calculating the difference between the present output sample of the sensor 310 and an output sample that was collected at a predefined earlier period (e.g., a specified number of motor steps or samples earlier, such as 128 steps) and comparing the difference between the two output samples to a predefined timing mark threshold (e.g., 200). The predefined earlier period (i.e., to which earlier sample is the present sample compared) and the predefined timing mark threshold may be predefined control parameters stored in memory 404. That is, if the sensor output between two samples separated by the specified time period drops by an amount exceeding the threshold, this abrupt transition is taken as an indication that the sensor has passed over the leading edge (i) of the timing mark 810, and the controller correlates the rotational position coinciding with the drop in output as the relative position of the leading edge of the timing mark 810. Similarly, if the sensor output rises by an amount exceeding the threshold, this is taken as an indication that the sensor has passed over the trailing edge (ii) of the timing mark 810 (or the trailing edge (iii) of the timing mark modifier 814), and the controller 400 correlates the rotational position coinciding with the rise in output as the position of the trailing edge of the timing mark 810, or the rotational position of the trailing edge of the timing mark modifier 814.

Figure 32:
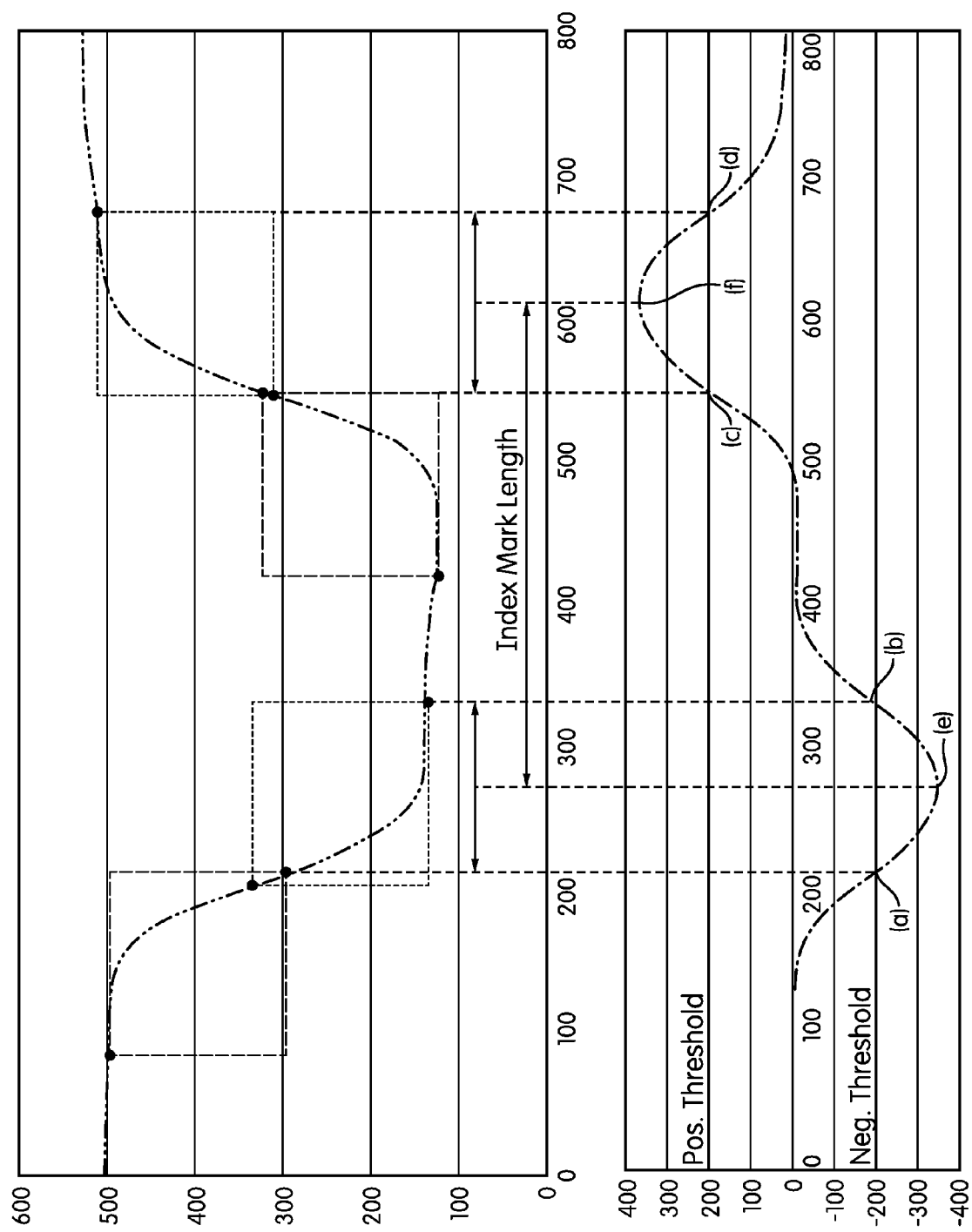
FIG. 32 is a plot of a waveform from the timing mark sensor and a plot of a differential waveform as the timing mark passes before the timing mark sensor.

FIG. 32 illustrates an exemplary algorithm for computing the length of the timing mark 810 (and possibly the timing mark modifier 814) from the waveform data. FIG. 32 shows an example sensor waveform (top curve) in the vicinity of the timing mark portion of the waveform (portions A, B, C in FIG. 31) and the results of the difference calculation (lower curve). The rectangles define "filters" for computing the difference and determining when the difference exceeds a threshold (long-dashed lines indicating the filter for detecting the beginning of a transition, short-dashed lines indicating the filter for detecting the end of a transition). The width of the filter corresponds to the predefined earlier period (e.g., 128 samples), and the height corresponds to the timing mark threshold value (e.g., ±200).

The difference calculation, as shown in the lower curve in FIG. 32, identifies four conditions that are detected: (a) the filter result (i.e., difference between samples separated by the predefined period) falls under the negative timing mark threshold, (b) the filter result rises over the negative timing mark threshold, (c) the filter result rises over the positive timing mark threshold, and (d) the filter result falls back under the positive timing mark threshold. These four points are used to calculate the length of the timing mark 810 (and possibly the timing mark modifier 814) as detected by the sensor 310 by taking the distance between a point (f) bisecting points (c) and (d) and a point (e) bisecting points (a) and (b). The calculated length between points (f) and (e) is used to determine whether the label 800 of the tube 12 includes a printed timing mark modifier 814, indicating that the tube has been previously used and the label printed on, to thereby prevent an already used (and printed on) tube from being reused. The length of the timing mark 810 and the length of the timing mark modifier 814 are control parameters stored in memory 404. In an exemplary embodiment, the length of the timing mark 810 is 7.0 mm, and the trailing edge (iii) of the timing mark modifier 814 extends 2.0 mm beyond the trailing edge (ii) of the timing mark 810. Thus, in such an embodiment, if the distance between points (f) and (e) in the waveform, is approximately the length of the timing mark 810 (e.g., 7.0 mm), the controller determines that the tube 12 has not been previously used. On the other hand, if the distance between points (f) and (e) in the waveform is approximately equal to the length of the combination of the timing mark 810 and the timing mark modifier 814 (e.g., 9.0 mm), the controller determines that the tube 12 has been previously used. In an embodiment, a single length threshold may be defined (e.g., 8.0 mm in the example above, which is the average of 7.0 mm and 9.0 mm), and a calculated timing mark length below the length threshold is deemed to indicate an un-used tube, and a calculated timing mark length above the length threshold is deemed to indicate a previously-used tube.

Assuming the tube has not been previously used and printed on, point (f) identifies the position of the trailing edge (ii) of the timing mark 810 within the waveform, and the controller 400 correlates the rotational position coinciding with that point.

After determining the position of the trailing edge of the timing mark 810, in the second step of the seek start procedure, tube 12 is rotated by the container rotating assembly 260 by a specified distance (e.g., number of motor steps) so as to place the sensor 310 at a predefined, print start position, such as the far edge of the label 800 (the lower edge of the label 800 as oriented in FIG. 29). In an embodiment, the control algorithm needs to account for the distance the motor 300 requires to decelerate at the end of this step, so that the amount of rotation commanded (e.g., the number of motor steps) is less than the amount of rotation required to place the tube in the print start position. For example, assuming a distance of 28.5 mm from the trailing edge (ii) of the timing mark 810 to the print start position, a motor velocity of 60 rad/s, and a motor deceleration of 1000 rad/s$^2$, the commanded distance of (constant velocity) movement needs to be 2.4 mm less than the actual required distance of 28.5 mm, leading to a 26.1 mm movement command.

At this stage, the tube is rotationally positioned at its print start position with respect to the sensor 310 and the print head 152, and the bracket expander 220 is activated to close the expandable printing station 50. After the printing station is closed, the print process is performed, which, in general, includes three sub-processes: re-locating the timing mark 810, printing the timing mark modifier 814, and printing the image (e.g., a barcode) on the printable area 812.

More specifically, the print process consists of seven steps. These seven steps (1)-(7) are illustrated in FIG. 33, which shows the sensor waveform, the velocity of the motor 300, and five snapshots—(j), (k), (l), (m), (n)—of the sensor 310, the print head 152, and the tube 12 throughout the print process.

Figure 33:
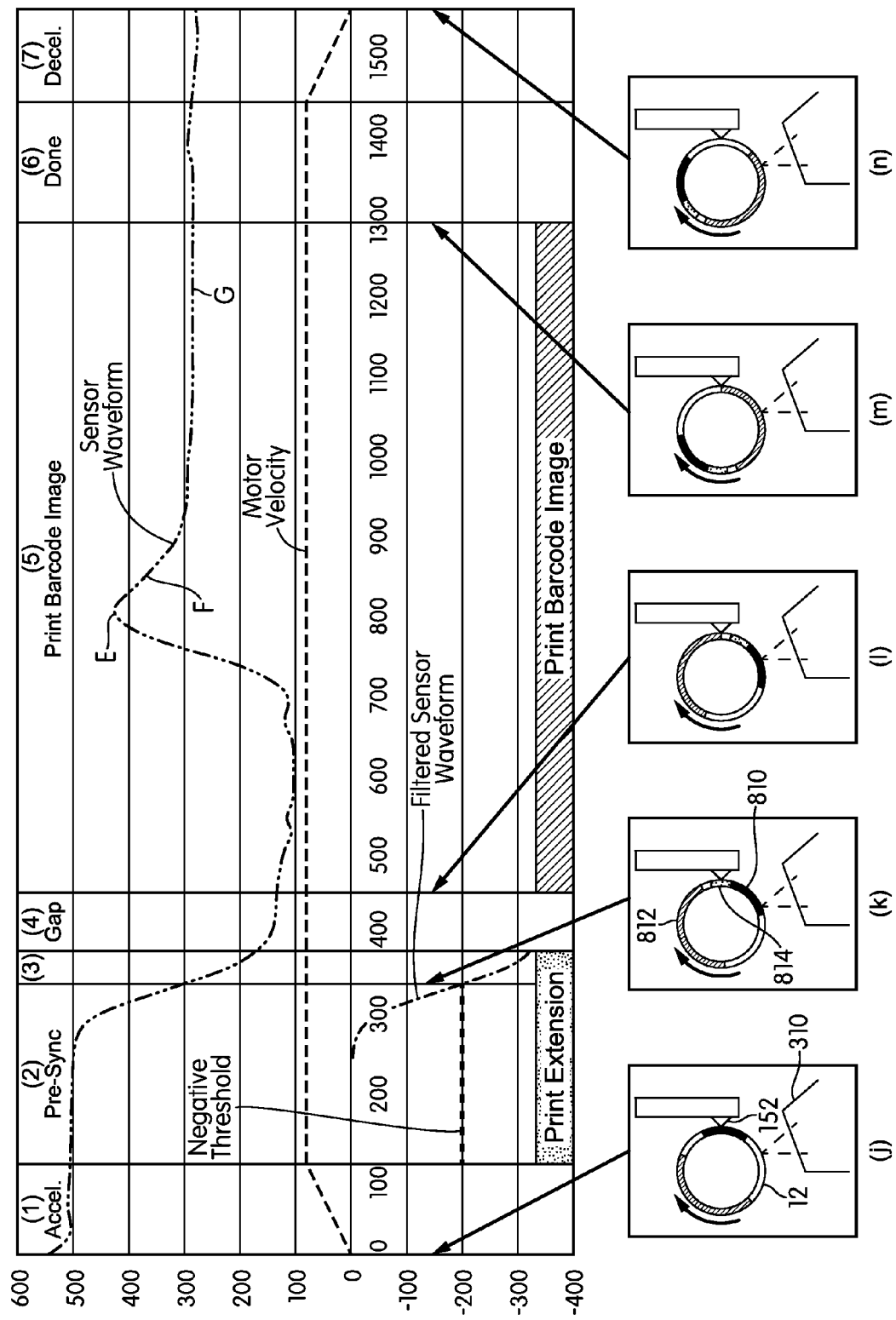
FIG. 33 is a plot illustrating steps of a printing process for printing an image and a timing mark modifier on the label.

In step (1), the motor 300 accelerates to a constant velocity, and the waveform is relatively flat, since, as shown in part (j) of FIG. 33, the sensor 310 is at the print start position, which is a portion of the label 800 preceding the timing mark 810. Note also that in the illustrated embodiment, the print head 152 is disposed over the timing mark 810 at this instant.

Step (2) begins when motor 300 reaches constant speed at which time the controller 400 commands the print head 152 to start printing the timing mark modifier 814 (over the timing mark 810). In an embodiment, step (2) ends when the sensor difference signal (filtered sensor waveform) falls for the first time under the negative timing mark threshold (see point (a) in FIG. 32). As shown in part (k) of FIG. 33, at the end of step (2), the timing mark 810 begins to pass before the sensor 310 (which is the point at which the waveform falls below the negative timing mark threshold), and the print head begins to print a portion of the timing mark modifier 814 that extends beyond the trailing edge of the timing mark 810.

In an embodiment, during step (3), after the detection of the leading edge of the timing mark 810 signaling the end of step (2), the print head 152 continues to print the remainder of the timing mark modifier 814. Step (3) is concluded when the timing mark printing is complete. The duration of step (3) depends on the length of the extension mark 814—which controls the amount of relative movement between the print head 152 and the label 800 during step (3)—and a calibration value that compensates for variations in relative positions between the tube sensor and the print head. The length of the extension mark 814 may be predefined control parameters stored in memory 404. The calibration value can be computed for a given module—as described below—and then stored in memory 404.

Thus, the timing mark modifier 814 is printed over first and second periods defined by steps (2) and (3), respectively. The duration of step (2) (first period) is not controlled by a predetermined number of steps by motor 300, but is, instead, controlled by the detection of the leading edge of the timing mark 810. The duration of step (3) (second period) depends on the amount of relative movement between the print head 152 and the label 800 during step (3) required to the print the desired length of the extension mark 814. The first period is thereby controlled by the detection of the timing mark. And the second period is thereby controlled by a motor command for a specified number of motor steps to effect the necessary amount of relative movement.

In step (4), the print head 152 is deactivated while the tube 12 continues to rotate to effect a predetermined amount of relative movement between the print head 152 and the label to generate a gap of no printed content between the trailing edge (iii) of the timing mark modifier 814 and the next printed content, which may be the human-readable text and the barcode image beginning in the printable area 812.

During step (5), the print head 152 is commanded to print the image (e.g., human-readable text and/or the barcode) on the printable area 812. The length of step (5)—and the circumferential length of the image—are determined by the amount of tube rotation while the print head 152 is activated. This rotation moves the label by a specified image distance with respect to the print head 152 and may be controlled by commanding a number of steps of motor 300, which may be a predefined control parameter stored in memory 404, while the print head 152 is activated. As shown in part (l) of FIG. 33, at the beginning of step (5), the print head 152 is positioned at the beginning of the printable area 812, and the sensor 310 is roughly aligned with the middle of the timing mark 810. As shown in part (m) of FIG. 33, at the end of step (5), the print head 152 is positioned at the end of the printable area 812, and the sensor 310 is roughly aligned with the middle of the printable area 812. As shown in the portion of the sensor waveform during step (5), the waveform reaches a peak at point E corresponding to the gap (region of maximum reflectance) between the trailing edge (iii) of the timing mark modifier 814 and the printed content of the printable area 812 created during step (4). Following the peak at point E, the waveform drops at F to a lower, relatively constant level at G as the sensor 310 passes over the printable area 812 on which the print head 152 has just printed a barcode or other image that will reduce the reflectance and result in a lower value of the waveform.

The image that is printed may be wholly or partially stored in system memory 404. The image may be a previously-stored image that is retrieved from memory 404 for each tube on which it is to be printed or it may be temporarily stored from an input received just prior to printing, for example as an input from onboard barcode reader 614 after reading an identification barcode on a first sample container 606 (see steps 708, 710 of FIG. 28).

Step (5) concludes after the tube has rotated so as to move the label the specified image distance with respect to the print head 152 while the print head 152 is activated so as to form a complete image.

Step (6) begins after the image is printed and the print head 152 is deactivated. In step (6) the tube continues to be rotated at constant speed with the print head deactivated to create a gap adjacent the image formed in the printable area 812. In step (7) the motor 300 decelerates to a stop to conclude the printing process.

After printing is complete, the bracket expander 220 is activated to open the expandable printing station 50. The final step is to check for possible slippage of the tube 12 with respect to the pivoting gripper assemblies 280 during printing.

Slippage detection is performed by checking for the reoccurrence of the start of the timing mark 810. The position of this transition is a measure for the slippage that occurred during the print process (including any slippage that might occur while opening the expandable printing station 50). As shown in part (n) of FIG. 33, at the conclusion of the printing process, i.e., at the end of step (7), the sensor 310 is located at or near the trailing edge (vi) of the printable area 812. The distance between the trailing edge and the beginning of the timing mark 810 is known from the label geometry and may be a control parameter stored in memory 404. The sensor 310 and the label 800 are moved relative to each other, e.g., the tube 12 is rotated, and the waveform is monitored until the sensor difference signal (filtered sensor waveform) falls for the first time under the negative timing mark threshold (point (a) in FIG. 32), to indicate that the leading edge (i) of the timing mark 810 has been encountered. If the distance that the tube rotates before the timing mark 810 is encountered is within a predefined range of the known distance (e.g., number of motor steps) between the trailing edge (vi) of the printable area 812 and the leading edge (i) of the timing mark 810, then the tube is deemed to have rotated properly during the printing process. On the other hand, if the distance that the tube rotates before the timing mark is detected is not within the predefined range of the known distance between the printable area 812 and the timing mark 810, meaning that the printable area 812 is not the correct width, then the tube is deemed to have slipped during the printing process.

The process described above is used to detect slippage after printing by measuring the distance between the pintable area 812 and the timing mark 810. In addition, before printing is complete, slippage may be detected when the timing mark is re-synchronized at the beginning of the printing process by measuring the distance between the print start position (e.g., the edge of the label 800) and the timing mark 810. If the distance between the print start position and the timing mark 810—i.e., the distance covered during steps (1) and (2) in the process illustrated in FIG. 33—is not within a predefined range of the expected distance, it is possible that the tube has slipped, perhaps when the expandable printing station 50 was closed. The predefined range may be a control parameter stored in memory 404.

An optional additional step, after checking for slippage, is to rotate the tube 12 to a final orientation facing the just-printed image to the opposite side of the tube 12 from the print head 152, which may be done to avoid an additional barcode centering process after the tube is removed from the printing module 10.

In various embodiments incorporating a reflectance detector for the sensor 310, the illumination source (e.g., an LED) of the sensor is energized only when needed and only with as much power as is necessary for a given operation. Thus, for example, the illumination source may be energized while confirming the presence of the tube, while locating and measuring the timing mark, while locating and measuring the timing mark modifier, or during slippage detection. At other times when the sensor 310 is not being used, the illumination source is not energized so as to extend the life of the illumination source and improve the reliability of the sensor 310.

In an embodiment, a sensor calibration procedure is performed to compute the calibration value used to compensate for variations in the relative positions of the sensor 310 and the print head 152. Due to manufacturing tolerances, the rotational distance between the sensor 310 and the print head 152 may vary from one printing module 10 to another. To determine the rotational distance between the sensor 310 and the print head 152 for a particular module 10, a tube 12 is placed into the module 10, and the timing mark modifier 814 is printed—without other parts of the image, such as the barcode—using the print process described above in connection with FIG. 33. Next, the length of the printed timing mark modifier 814 is computed from the waveform using the process described above in connection with FIG. 32, and this value is compared to the expected length of the timing mark modifier 814. Any variation between the measured and expected lengths of the timing mark modifier, due to the sensor 310 and print head 152 being closer or further apart than expected, may be used to calculate a calibration value. Typically, the relative positions of print head 152 and sensor 310 are expected to be constant over the lifespan of the printing module 10 (not accounting for potential maintenance). Thus, in an embodiment, the sensor calibration process is executed once during manufacturing or installation.

As an alternative to the dark timing mark 810 and timing mark modifier 814 described above, if the label background is dark in color, the timing mark 810 may be formed of a solid, light color to provide a detectable distinction. For example, the timing mark may take the form of a white mark, such as a white square, rectangle, bar, etc., formed on a dark band extending across the label (i.e., surrounding the tube 12). In the case of a white timing mark, the timing mark modifier may not comprise an overlapping mark that extends the circumferential length of the timing mark, such as timing mark modifier 814 which extends the length of timing mark 810, but instead may comprise a dark mark overlapping the white timing mark so as to detectably reduce the length of the timing mark.

It can be appreciated that in such an embodiment in which the timing mark is lighter than its surroundings, the waveform generated by the timing mark sensor 310 would essentially be the inverse of the waveform shown in FIG. 31. Transitions in the waveform indicating the leading and trailing edges of the timing mark would be indicated by leading jump in the waveform that exceeds a positive threshold and a trailing drop in the waveform that falls below a negative threshold.

Yet another alternative timing mark may comprise a cut-out formed in the label where the optical properties, e.g., reflectance, of the material underlying the label and visible through the cut-out are different than the remainder of the label so that the hole can be detected by the timing mark sensor. Alternatively, the edges of a cut-out may be detectable by a suitably sensitive contact sensor. The print start position can located at a specified distance from the cut-out, as described above, and slippage detection can be performed by confirming the correct distance between the end of the printed image and the cut-out, as also described above. A separate, optically-detectable timing mark modifier can be printed at a predefined location relative to the cut-out, and the system can confirm that a tube has not been previously printed on by confirming the absence of a timing mark modifier prior to printing.

Yet another alternative timing mark may comprise a physical feature formed in the side of the tube, such as a raised bump or a recess, which is detectable by a mechanical sensor, such as a contact sensor. For such a timing mark formed on the tube itself, care must be taken to apply a printable label in the proper position with respect to the timing mark so as to ensure a proper location of the printed image on the label. The print start position can located at a specified distance from the physical feature, as described above, and slippage detection can be performed by confirming the correct distance between the end of the printed image and the physical feature, as also described above. A separate, optically-detectable timing mark modifier can be printed at a predefined location relative to the physical feature, and the system can confirm that a tube has not been previously printed on by confirming the absence of a timing mark modifier prior to printing.

Yet another alternative to timing mark 810 may comprise encoder ticks formed across the label so as to extend circumferentially around the tube. One of the encoder ticks may be formed differently than the other encoder ticks, e.g., longer, wider, narrower, etc., so as to define a "home" encoder tick that functions as the timing mark. The remaining ticks, being distributed at a known angular spacing, can provide position information relative to the home encoder tick simply by counting the ticks from the home tick using an incremental encoder.

The print start position can be found by counting a specified number of encoder ticks from the home tick. In addition, slippage detection can be performed while the image is being printed by ensuring that correct number of encoder ticks have passed the sensor when the image is complete. A separate, optically-detectable timing mark modifier can be printed at a predefined location—as determined from encoder ticks, and the system can confirm that a tube has not been previously printed on by confirming the absence of a timing mark modifier prior to printing.

Sensor 310 may be replaced or supplemented by a machine vision-based sensor that detects specific features on the label for providing relative locations on the label. Machine-vision based sensors can be used in an incremental encoder system to detect and count encoder ticks. Alternatively, machine-vision sensors can be used in an absolute encoder system in which encoder marks are sequentially labeled, e.g., incrementally numbered, and such sequential labels can be read by a machine-vision camera to provide absolute locations on the label.

Figure 35:
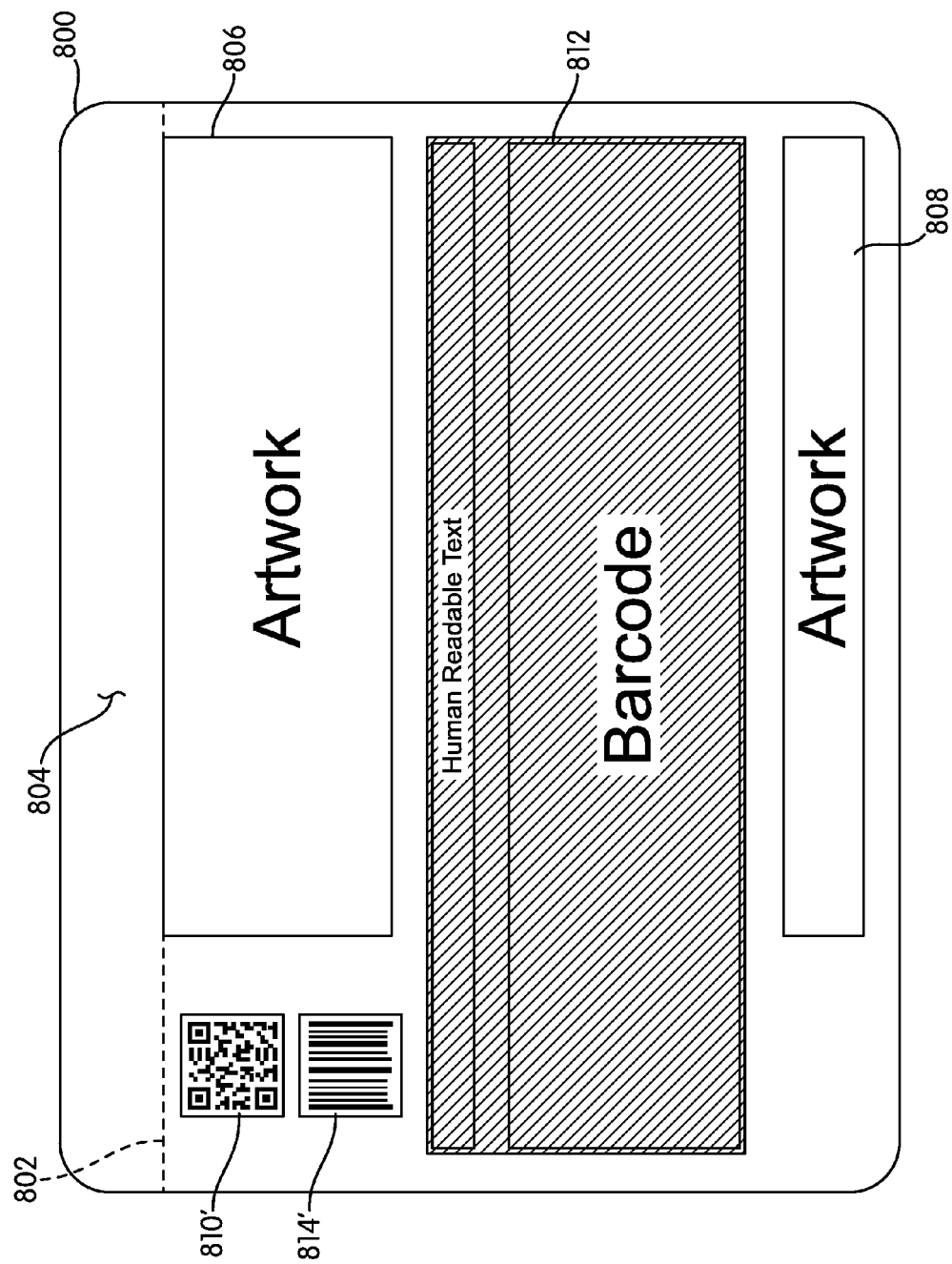
FIG. 35 is a plan view of a printable label including an alternate embodiment of a pre-printed timing mark and timing mark modifier.

In yet another alternative to timing mark 810, the timing mark sensor is a barcode reader, and the timing mark and the timing mark modifier may comprise 2-D and/or 1-D barcodes. Such an alternative is shown in FIG. 35 in which the timing mark 810' is a 2-D barcode and the timing mark modifier 814' is a 1-D barcode. FIG. 35 is exemplary; either the timing mark or the timing mark modifier could be a 2-D barcode or a 1-D barcode.

A 2-D barcode reader is able to identify a particular coordinate on the 2-D barcode, e.g., the origin (at the leading edge of the barcode) and/or a coordinate point on the trailing edge, and thus a specific location on the label can be identified by reading timing mark 810' without having to interpret positive and negative changes in a waveform as described above.

A 1-D barcode and barcode reader are also able to provide accurate location information without requiring analysis of a waveform. As the label is moved with respect to the barcode reader, the location at which the barcode reader is first able to read the 1-D barcode defines the leading edge of the barcode, and the last location at which the barcode reader is able to read the barcode defines the trailing edge of the barcode.

Using the leading edge position of the timing mark (either as determined by a leading edge coordinate of a 2-D barcode or as determined by the leading edge of a 1-D barcode), the print start position can be determined, as described above, and post-printing slippage detection can be performed, as described above. Using the leading and trailing edges of the timing mark modifier, pre-printing slippage detection can be performed as described above.

In addition, using a barcode reader that is within the printing module 10, the image formed on the label can read to ensure it is of adequately readable quality before the tube 12 is removed from the module.

In an embodiment, the printing module 10 will be configured to operate in an "alternate print" mode whereby the printing module will print an alternate image on the label 800 even if a tube 12 could not be detected or the timing mark 810 could not be found (e.g., because of a malfunctioning sensor 310). Thus, in the event of a sensor malfunction, it will not always be necessary to shut down the printing module 10 until the sensor can be repaired.

When the controller of the instrument 600 "knows" a tube 12 was placed into the printing module 10, for example, after step 706 of work flow 700 shown in FIG. 28, but the presence of the tube cannot be confirmed by the sensor 310 or if the presence of the tube can be confirmed but the timing mark 810 cannot be detected by the sensor 310, the printing module 10 will operate in alternate print mode and print an alternate, readable image on the tube so that the tube can thereafter be processed by the instrument 600. On the other hand, if a previously-used tube having a barcode is placed in the module 10, and the timing mark modifier is not detected, e.g., because the sensor 310 is malfunctioning, it is important that the tube not be re-used even if a new barcode is printed on the tube. Thus, in various embodiments, the sample processing station 610 is configured to scan for images at multiple locations on the tube 12 so that it can detect an image made in the printable area 812 as well as images printed elsewhere on the label 800. If multiple, inconsistent barcodes are detected, processing may be terminated for that tube.

Figure 34:
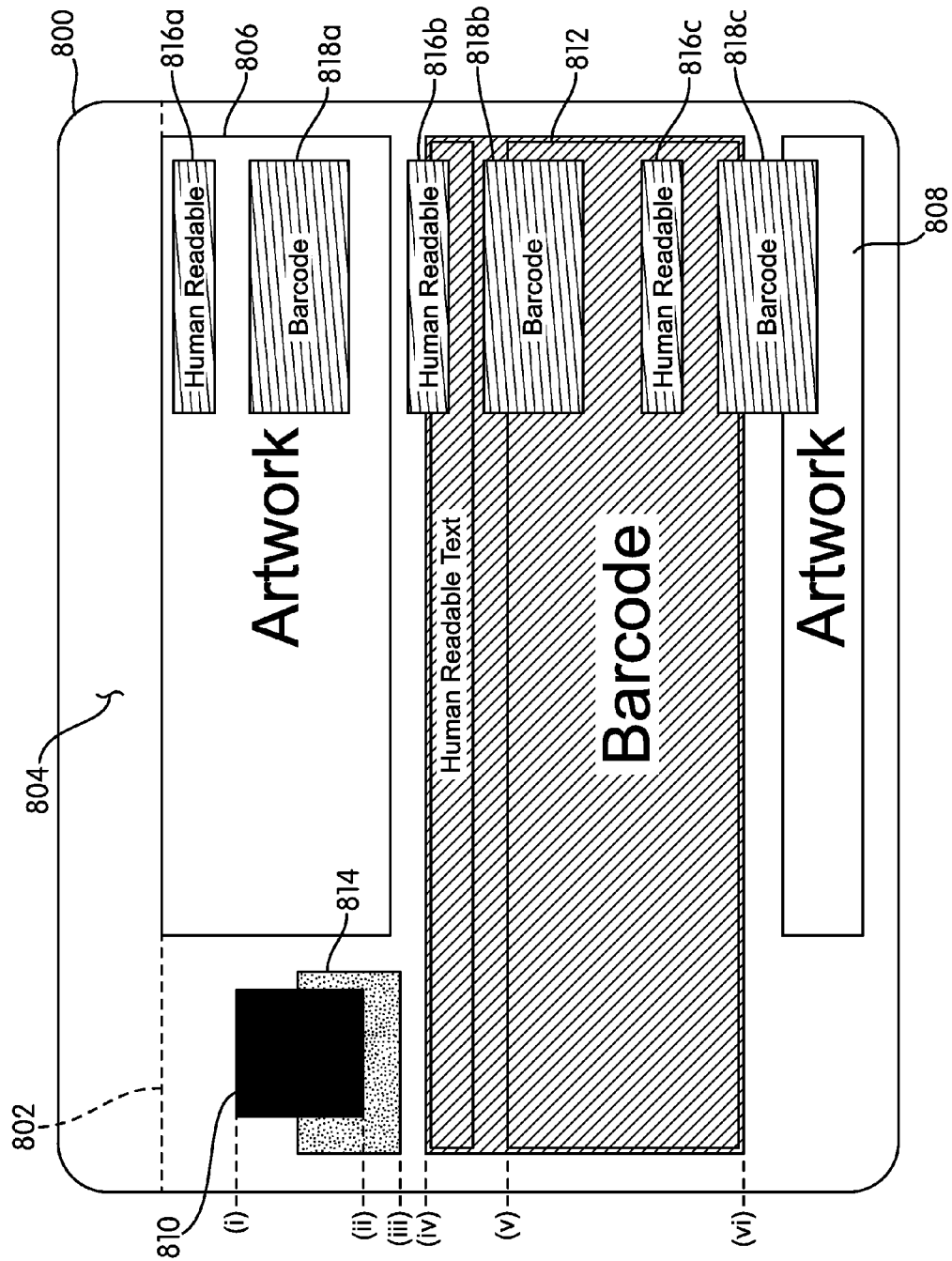
FIG. 34 is a plan view of a printable label on which alternate images have been printed.

As shown in FIG. 34, to allow both the old barcode made in the printable area 812 and new barcodes to be scanned and detected at the sample processing station 610, an alternate print mode does not print the normal image (e.g., human-readable label and barcode) in the printable area 812 of the label 800, which could potentially lead to overprinting the previously-printed image. Instead, during alternate print mode, the print head 152 is selectively activated during relative movement between the print head 152 and the label 800 to print smaller, alternate images on different portions of the label 800. The alternate images may comprise one or more human-readable labels 816*a*, 816*b*, 816*c* and/or one or more machine-readable images (e.g., 1-D or 2D barcodes) 818*a*, 818*b*, 818*c* that are the same images that would have been printed in the printable area 812 had the printer module functioned normally. In an embodiment, as shown in FIG. 34, labels 816*a-c* and/or barcodes 818*a-c* are smaller than an image printed in the printable area 812 and are preferably printed in multiple locations so that at least one of the images 816/818 is printed on an unprinted (e.g., white) portion of the label 800 outside the printable area 812. The pattern of the image(s) 816/818 (i.e., number, location, size, orientation, spacing, etc.) can be defined to account for the configuration of the label 800 and the location of other elements, such as the timing mark 810, areas 806, 808, and printable area 812. Although alternate images 816/818 in FIG. 34 are aligned (vertically as shown in FIG. 34, horizontally as applied to a tube 12), the alternate images 816/818 need not be so-aligned and could be printed at different locations depending on the configuration of the label 800, for example, so as to increase the likelihood that an alternate image will be printed on an unprinted area.

In an embodiment, the alternate print mode operates as follows.

In a first step, upon receiving a signal that the pick and place mechanism 640 has placed a tube 12 into the printing module 10 (after step 707 in FIG. 28 or step 454 in FIG. 21), the controller transmits a signal (e.g. a power and/or command signal) to the tube present sensor 310 to confirm the presence of the tube in the printing module 10. In other words, the system attempts to perform step 456 in FIG. 21.

In a conditional next step, if the tube present sensor 310 fails to generate a signal confirming the presence of the tube 12 in the printing module 10, e.g. because of a malfunction of the tube present sensor, the controller retrieves the image to be printed from memory 404 and transmits an alternate print command (e.g., power and/or control command) to the rotating assembly 260 to rotate the tube and to the print head 152 to selectively activate the print head so as to print the alternate images at multiple locations on the tube.

In an alternate conditional step, if the tube present sensor 310 generates a signal confirming the presence of the tube in the printing module 10, the controller transmits a command to the rotating assembly 260 and the timing mark sensor 315 (which may be the same sensor as tube present sensor 310) to perform a timing mark location procedure, such as a procedure described above.

In a conditional next step, if the timing mark sensor 315/310 fails to generate a signal indicating the detection and location of a timing mark on the tube, e.g. because of a malfunction of the timing mark sensor, the controller transmits the alternate print command to the rotating assembly 260 and to the printer 152 to print the alternate images at multiple locations on the tube.

In this embodiment, in the first instance, if the sensor fails to confirm the presence of the tube, there is no need to scan for the location of the timing mark, and the alternate images are then printed after fail to detect the presence of the tube. In the second instance, if the sensor is able to confirm the presence of the tube, but is unable to detect the location of the timing mark, the alternate images are printed after the failure to locate the timing mark.

It will be appreciated by those skilled in the art that the foregoing description of a printing control process, including the use of a timing mark sensor, a printer label, a timing mark, and a timing mark modifier is not exclusively applicable to printing on a curved surface, such as tube 12. Instead, the printing control process may be implemented in any method for controlling an automated printing process by which a print head prints an image onto predetermined printable area of a label during relative movement between the print head and the label.

EXEMPLARY EMBODIMENTS

The following embodiments are encompassed by the foregoing disclosure.

Embodiment 1

An apparatus for printing on a curved surface of an article comprising:
(A) an expandable printing mechanism including a print head and configured and controlled to be selectively:
  (1) expanded to an open configuration for enabling an article having a curved surface on which information is to be printed to be received within or removed from the apparatus, and
  (2) contracted to a printing configuration placing the curved surface of an article received within the apparatus in operative position with respect to the print head and maintaining the curved surface in an operative printing position with respect to the print head during relative movement of the curved surface with respect to the print head; and
(B) an article moving assembly configured and controlled to:
  (1) grasp an article received within the apparatus and effect relative movement between the curved surface of the article and the print head when the expandable printing mechanism is in the printing configuration, and
  (2) release the article when the expandable printing mechanism is in the open configuration, thereby allowing the article to be removed from the apparatus.

Embodiment 2

The apparatus of Embodiment 1, further comprising a housing at least partially enclosing the expandable printing mechanism and the article moving assembly.

Embodiment 3

The apparatus of Embodiment 2, further including an opening formed in the housing through which an article having a curved surface on which information is to be printed can be received within or removed from the apparatus.

Embodiment 4

The apparatus of any one of Embodiments 1 to 3, wherein the expandable printing mechanism comprises:
  a first support element having one or more contact element(s) operatively supported thereon; and
  a second support element supporting the print head thereon, wherein the first support element and the second support element are configured for relative movement with respect to each other between the open configuration of the expandable printing mechanism and the printing configuration of the expandable printing mechanism, and wherein the contact element(s) are configured to contact an article received within the apparatus to hold the curved surface in the operative position with respect to the print head when the expandable printing mechanism is in the printing configuration.

Embodiment 5

The apparatus of Embodiment 4, wherein the one or more contact elements comprise a first roller and a second roller rotatably mounted to the first support element.

Embodiment 6

The apparatus of Embodiment 4 or 5, further comprising an expander mechanism configured to effect relative movement of the first and second support elements between the open configuration and the printing configuration.

Embodiment 7

The apparatus of Embodiment 5 or 6, wherein the first roller is axially elongated, and the second roller comprises, extending axially along the length of the roller, a first head portion that is of a first diameter, an extension portion that is of a second diameter that is less than the first diameter, and a second head portion that is of a third diameter that is greater than the second diameter.

Embodiment 8

The apparatus of Embodiment 7, wherein the third diameter is equal to the first diameter.

Embodiment 9

The apparatus of Embodiment 7 or 8, wherein the first roller is cylindrical.

Embodiment 10

The apparatus of Embodiment 7 or 8, wherein the first roller has a varying diameter that increases from each axial end of the roller to the axial middle of the roller.

Embodiment 11

The apparatus of any one of Embodiments 5 to 10, wherein:
the first support element comprises a roller bracket having an upper flange, a lower flange, and a web extending between the upper and lower flanges, and wherein the first roller and the second roller are rotatably mounted between the first and second flanges;
the second support element comprises a print head bracket having an upper flange, a lower flange, and a web extending between the upper and lower flanges, the roller bracket and the print head bracket being oriented such that the webs of the roller bracket and the print head bracket are generally parallel to one another; and
the roller bracket and the print head bracket are pivotably mounted to a common pivot shaft so that the roller bracket and the print head bracket are pivotable with respect to each other in a hinge-wise fashion about the pivot shaft between the open configuration and the printing configuration.

Embodiment 12

The apparatus of any one of Embodiments 6 to 11, wherein:
the first and second support elements are pivotably mounted to a common pivot shaft so that the first and second support elements are pivotable with respect to each other in a hinge-wise fashion about the pivot shaft between the open configuration and the printing configuration, and wherein the expander mechanism comprises:
a driven shaft located between the first and second support elements, the driven shaft being generally parallel to the pivot shaft; and
a cam element attached to and rotatable with the driven shaft and in contact with both the first and second support elements, wherein the cam element has a varying dimension so that in one orientation of the cam element, portions of the cam element contacting the first and second support elements hold the first and second support elements apart by a first distance corresponding to the open configuration of the expandable printing mechanism and in another orientation of the cam element, portions of the cam element contacting the first and second support elements hold the first and second support elements apart by a second distance corresponding to the printing configuration of the expandable printing mechanism.

Embodiment 13

The apparatus of Embodiment 12, wherein the cam element comprises a cam disc fixed to the driven shaft and coaxial therewith, the cam disc having a variable radius so that in a first rotational position of the cam disc, portions of the cam disc having a first radius are in contact with the first and second support elements and holding the first and second support elements apart by the first distance corresponding to the open configuration, and in a second rotational position of the cam disc, portions of the cam disc having a second radius that is smaller than the first radius are in contact with the first and second support elements and holding the first and second support elements apart by the second distance corresponding to the printing configuration.

Embodiment 14

The apparatus of Embodiment 12 or 13, wherein the expander mechanism further comprises a spring extending between the first and the second support elements and configured to bias the first and the second support elements into contact with the cam element.

Embodiment 15

The apparatus of any one of Embodiments 12 to 14, wherein each of the first and second support elements further includes a roller bearing mounted thereon, wherein the cam element contacts the roller bearing of each of the first and second support elements.

Embodiment 16

The apparatus of any one of Embodiments 12 to 15, further comprising a drive mechanism comprising:

a pulley wheel coaxially mounted to the driven shaft;
a motor having an output shaft and a drive wheel; and
a drive belt coupling the drive wheel to the pulley wheel.

Embodiment 17

The apparatus of any one of Embodiments 12 to 16, wherein the expander mechanism further comprises a rotational position sensor configured to detect a rotational position of the driven shaft and cam element.

Embodiment 18

The apparatus of Embodiment 17, wherein the rotational position sensor comprises:
an index wheel coaxially coupled to the driven shaft and having one or more detectable features formed therein or attached thereto at specified rotational positions; and
an optical sensor configured to detect the one or more detectable features as the driven shaft and the index wheel rotate with respect to the optical sensor.

Embodiment 19

The apparatus of any one of Embodiments 12 to 18, further comprising a hand wheel mounted to the driven shaft and configured to enable manual rotation of the driven shaft and the cam element.

Embodiment 20

The apparatus of any one of Embodiments 4 to 19, wherein the second support element comprises a print head platen on which the print head is mounted.

Embodiment 21

The apparatus of Embodiment 20, wherein the print head platen is configured and mounted so that its position on the second support element can be laterally adjusted.

Embodiment 22

The apparatus of Embodiment 21, further comprising a platen shaft mounted to the second support element, wherein the platen shaft extends through a portion of the print head platen, so as to permit lateral movement of the print head platen along the platen shaft.

Embodiment 23

The apparatus of Embodiment 22, further comprising a platen adjustment lever pivotably mounted to the second support element and including a contact point in contact with a portion of the print head platen and configured such that pivoting movement the platen adjustment lever effects lateral movement of the print head platen along the platen shaft.

Embodiment 24

The apparatus of Embodiment 23, wherein the platen adjustment lever includes a protuberance that is configured to be inserted into one of a plurality of holes formed in the second support element to secure the platen adjustment lever at a selected rotational position.

Embodiment 25

The apparatus of any one of Embodiments 1 to 24, further comprising a timing mark sensor configured to detect a timing mark on the curved surface.

Embodiment 26

The apparatus of any one of Embodiments 1 to 25, wherein the article moving assembly comprises:
carousel configured for powered rotation; and
moveable gripper elements configured to be movable between a release position permitting an article to be placed within or removed from the apparatus and a gripping position for securing the article with respect to the carousel so that the article rotates with the carousel.

Embodiment 27

The apparatus of Embodiment 26, wherein each gripper element comprises a gripper assembly that is coupled to the carousel and is configured so that rotation of the carousel in a first direction causes all the gripper assemblies to move radially inwardly to the gripping position with respect to an article placed between the gripper assemblies and rotation of the carousel in a second direction opposite the first direction causes all the gripper assemblies to move radially outwardly to the release position with respect to the article.

Embodiment 28

The apparatus of Embodiment 27, comprising three gripper assemblies.

Embodiment 29

The apparatus of any one of Embodiments 26-28, wherein the carousel comprises:
an upper disc; and
a lower disc, coaxially arranged with the upper disc, the upper and lower discs being rotatable relative to one another.

Embodiment 30

The apparatus of Embodiment 29, wherein each gripper element comprises a pivoting gripper assembly comprising:
a pivot arm disposed between the upper disc and the lower disc of the carousel and pivotably attached to the upper disc;
a knurled wheel rotatably mounted above the upper disc on a shaft extending from the pivot arm through the upper disc; and
a guide pin extending from the pivot arm into an associated guide slot formed in the lower disc.

Embodiment 31

The apparatus of Embodiment 30, wherein a first end of each guide slot formed in the lower disc is closer to a radial center of the lower disc than a second end of the guide slot.

Embodiment 32

The apparatus of any one of Embodiments 26 to 31, wherein the article moving assembly further comprises a drive mechanism comprising:

a motor having an output shaft and a drive wheel; and
a drive belt coupling the drive wheel to the carousel.

Embodiment 33

The apparatus of Embodiment 32, wherein the carousel includes peripheral gear teeth for engagement by the drive belt.

Embodiment 34

The apparatus of any one of Embodiments 1 to 33, wherein the print head comprises a thermal print head.

Embodiment 35

A method for printing on a curved surface of an article with a printing module configured to receive an article having a curved surface, secure the article so that the curved surface is in an operative position with respect to a print head of the printing module, effect relative movement between the curved surface and the print head while the print head is activated and while maintaining the curved surface in the operative position with respect to the print head, thereby printing information onto the curved surface, and then release the article so that it may be removed from the printing module, the method comprising:
  confirming that the printing module is in an open configuration for enabling the article having a curved surface to be placed within the module;
  inserting the article into the printing module;
  moving the curved surface with respect to the print head;
  detecting a timing mark on the curved surface;
  configuring the printing module into a printing configuration whereby the curved surface of the article placed within the printing module is in an operative position with respect to the print head of the printing module;
  activating the print head;
  imparting an image onto the curved surface by moving the curved surface with respect to the print head while the print head is activated and maintaining the curved surface in the operative position with respect to the print head for a specified amount of relative movement;
  after imparting the image onto the curved surface, deactivating the print head and terminating relative movement between the curved surface and the print head;
  configuring the printing module into the open configuration whereby the article can be removed from the printing module; and
  removing the article from the printing module.

Embodiment 36

The method of Embodiment 35, wherein the timing mark is detected with a timing mark sensor configured to detect a change in the reflectivity of a portion of the curved surface.

Embodiment 37

The method of Embodiment 36, wherein the timing mark sensor generates a waveform based on the reflectivity of a portion of the curved surface, and wherein the timing mark is detected by detecting a change in the waveform the exceeds a predefined threshold.

Embodiment 38

The method of any one of Embodiments 35 to 37, further comprising the step of imparting a timing mark modifier onto the curved surface to indicate that the article has been printed on.

Embodiment 39

The method of any one of Embodiments 35 to 38, further comprising the step of, after detecting the timing mark, determining one or more dimensions of the timing mark and comparing the determined one or more dimensions of the timing mark to at least one predetermined threshold dimension.

Embodiment 40

The method of any one of Embodiments 35 to 39, further comprising the step of, after configuring the printing module into the open configuration, determining whether each determined dimension of the image is within a predefined range of an expected dimension of the image.

Embodiment 41

A method for printing on a curved surface of an article with a printing module, the method comprising:
  configuring the printing module in an open configuration to receive an article having a curved surface on which information is to be printed;
  placing an article into the printing module;
  configuring the printing module in a printing configuration and securing the article so that the curved surface is in an operative position with respect to a print head of the printing module;
  activating the print head and effecting relative movement between the curved surface and the print head while the print head is activated and while maintaining the curved surface in the operative position with respect to the print head;
  after printing an image onto the curved surface, configuring the printing module into an open configuration enabling the article to be removed from the printing module; and
  removing the article from the printing module.

Embodiment 42

A system for processing a sample comprising:
  a sample transfer apparatus configured to remove an amount of sample material from a first container and dispense at least a portion of the removed sample material in a second container;
  a code reading device configured to read a first machine-readable graphic code on a surface of the first container, the first machine-readable graphic code having encoded therein information relating to the sample material contained in the first container;
  a controller configured to generate a second machine-readable graphic code having encoded therein information relating to the information encoded in the first machine-readable graphic code; and a printing module configured and controlled to print the second machine-readable graphic code on a curved surface of the second container, the printing module comprising:
(A) an expandable printing mechanism including a print head and configured and controlled to be selectively:
(1) expanded to an open configuration for enabling the second container to be received within or removed from the printing module, and
(2) contracted to a printing configuration placing the curved surface of the second container in an operative printing position with respect to the print head and maintaining the curved surface in the operative printing position with respect to the print head during relative movement of the curved surface with respect to the print head; and
(B) a moving assembly configured and controlled to:
(1) grasp the received second container and effect relative movement between the curved surface of the second container and the print head when the expandable printing mechanism is in the printing configuration, and
(2) release the article when the expandable printing mechanism is in the open configuration, thereby allowing the article to be removed from the printing module.

Embodiment 43

The system of Embodiment 42, wherein the sample transfer apparatus comprises a pipettor carried on a robotic arm.

Embodiment 44

The system of Embodiment 42 or 43, further comprising a pick-and-place mechanism configured and controlled to selectively move either or both of the first and second containers from a first location within the system to a second location within the system.

Embodiment 45

The system of Embodiment 44, wherein the pick-and-place mechanism comprises a container gripper carried on a robotic arm.

Embodiment 46

The system of any one of Embodiments 42 to 45, wherein the printing module further comprises a housing at least partially enclosing the expandable printing mechanism and the moving assembly.

Embodiment 47

The system of Embodiment 46, further including an opening formed in the housing through which the second container can be moved into or out of the housing of the printing module.

Embodiment 48

The system of any one of Embodiments 42 to 47, wherein the expandable printing mechanism comprises:
a first support element having one or more contact element(s) operatively supported thereon; and
a second support element supporting the print head thereon,
wherein the first support element and the second support element are configured for relative movement with respect to each other between the open configuration of the expandable printing mechanism and the printing configuration of the expandable printing mechanism, and wherein the contact element(s) are configured to contact the second container received within the printing module to hold the curved surface in the operative position with respect to the print head when the expandable printing mechanism is in the printing configuration.

Embodiment 49

The system of Embodiment 48, wherein the expandable printing mechanism further comprises an expander mechanism configured to effect relative movement of the first and second support elements between the open configuration and the printing configuration.

Embodiment 50

The system of Embodiment 48 or 49, wherein the one or more contact elements comprise a first roller and a second roller rotatably mounted to the first support element.

Embodiment 51

The system of Embodiment 50, wherein
the first roller is axially elongated, and
the second roller comprises, extending axially along the length of the roller, a first head portion that is of a first diameter, an extension portion that is of a second diameter that is less than the first diameter, and a second head portion that is of a third diameter that is greater than the second diameter.

Embodiment 52

The system of Embodiment 51, wherein the third diameter is equal to the first diameter.

Embodiment 53

The system of any one of Embodiments 50 to 52, wherein the first roller is cylindrical.

Embodiment 54

The system of any one of Embodiments 50 to 52, wherein the first roller has a varying diameter that increases from each axial end of the roller to the axial middle of the roller.

Embodiment 55

The system of any one of Embodiments 50 to 54, wherein
the first support element comprises a roller bracket having an upper flange, a lower flange, and a web extending between the upper and lower flanges, and wherein the first roller and the second roller rotatably mounted between the first and second flanges;
the second support element comprises a print head bracket having an upper flange, a lower flange, and a web extending between the upper and lower flanges, the roller bracket and the print head bracket being oriented such that the webs of the roller bracket and the print head bracket are generally parallel to one another; and the roller bracket and the print head bracket are pivotably mounted to a common pivot shaft so that the roller bracket and the print head bracket are pivotable with respect to each other in a hinge-wise fashion about the pivot shaft between the open configuration and the printing configuration.

Embodiment 56

The system of any one of Embodiments 49 to 55, wherein:
the first and second support elements are pivotably mounted to a common pivot shaft so that the first and second support elements are pivotable with respect to each other in a hinge-wise fashion about the pivot shaft between the open configuration and the printing configuration, and wherein the expander mechanism comprises:
a driven shaft located between the first and second support elements, the driven shaft being generally parallel to the pivot shaft; and
a cam element attached to and rotatable with the driven shaft and in contact with both the first and second support elements, wherein the cam element has a varying dimension so that in one orientation of the cam element, portions of the cam element contacting the first and second support elements hold the first and second support elements apart by a first distance corresponding to the open configuration of the expandable printing mechanism and in another orientation of the cam element, portions of the cam element contacting the first and second support elements hold the first and second support elements apart by a second distance corresponding to the printing configuration of the expandable printing mechanism.

Embodiment 57

The system of Embodiment 56, wherein the cam element comprises a cam disc fixed to the driven shaft and coaxial therewith, the cam disc having a variable radius so that in a first rotational position of the cam disc, portions of the cam disc having a first radius are in contact with the first and second support elements and holding the first and second support elements apart by the first distance corresponding to the open configuration, and in a second rotational position of the cam disc, portions of the cam disc having a second radius that is smaller than the first radius are in contact with the first and second support elements and holding the first and second support elements apart by the second distance corresponding to the printing configuration.

Embodiment 58

The system of Embodiment 56 or 57, wherein the expander mechanism further comprises a spring extending between the first and second support elements and configured to bias the first and second support elements into contact with the cam element.

Embodiment 59

The system of any one of Embodiments 56 to 58, wherein each of the first and second support elements further includes a roller bearing mounted thereon, wherein the cam element contacts the roller bearing of each of the first and second support elements.

Embodiment 60

The system of any one of Embodiments 56 to 59, further comprising a drive mechanism comprising:

a pulley wheel coaxially mounted to the driven shaft;
a motor having an output shaft and a drive wheel; and
a drive belt coupling the drive wheel to the pulley wheel.

Embodiment 61

The system of any one of Embodiments 56 to 60, wherein the expander mechanism further comprises a rotational position sensor configured to detect a rotational position of the driven shaft and cam element.

Embodiment 62

The system of Embodiment 61, wherein the rotational position sensor comprises:
an index wheel coaxially coupled to the driven shaft and having one or more detectable features formed therein or attached thereto at specified rotational positions; and
an optical sensor configured to detect the one or more detectable features as the driven shaft and the index wheel rotate with respect to the optical sensor.

Embodiment 63

The system of any one of Embodiments 56 to 62, further comprising a hand wheel mounted to the driven shaft and configured to enable manual rotation of the driven shaft and the cam element.

Embodiment 64

The system of any one of Embodiments 48 to 63, wherein the second support element comprises a print head platen on which the print head is mounted.

Embodiment 65

The system of Embodiment 64, wherein the print head platen is configured and mounted so that its position on the second support element can be laterally adjusted.

Embodiment 66

The system of Embodiment 65, further comprising a platen shaft mounted to the second support element, wherein the platen shaft extends through a portion of the print head platen, so as to permit lateral movement of the print head platen along the platen shaft.

Embodiment 67

The system of Embodiment 66, further comprising a platen adjustment lever pivotably mounted to the second support element and including a contact point in contact with a portion of the print head platen and configured such that pivoting movement the platen adjustment lever effects lateral movement of the print head platen along the platen shaft.

Embodiment 68

The system of Embodiment 67, wherein the platen adjustment lever includes a protuberance that is configured to be inserted into one of a plurality of holes formed in the second support element to secure the platen adjustment lever at a selected rotational position.

Embodiment 69

The system of any one of Embodiments 42 to 68, further comprising a timing mark sensor configured to detect a timing mark on the curved surface.

Embodiment 70

The system of any one of Embodiments 42 to 69, wherein the moving assembly comprises:
a carousel configured for powered rotation; and
moveable gripper elements configured to be movable between a release position permitting an article to be placed within or removed from the printing module and a gripping position for securing the second container with respect to the carousel so that the article rotates with the carousel.

Embodiment 71

The system of Embodiment 70, wherein each gripper element comprises a gripper assembly that is coupled to the carousel and is configured so that rotation of the carousel in a first direction causes all the gripper assemblies to move radially inwardly to the gripping position with respect to the second container placed between the gripper assemblies and rotation of the carousel in a second direction opposite the first direction causes all the gripper assemblies to move radially outwardly to the release position with respect to the second container.

Embodiment 72

The system of Embodiment 71, comprising three gripper assemblies.

Embodiment 73

The system of any one of Embodiments 70 to 72, wherein the carousel comprises:
an upper disc; and
a lower disc, coaxially arranged with the upper disc, the upper and lower discs being rotatable relative to one another.

Embodiment 74

The system of Embodiment 73, wherein each gripper element comprises a pivoting gripper assembly comprising:
a pivot arm disposed between the upper disc and the lower disc of the carousel and pivotably attached to the upper disc;
a knurled wheel rotatably mounted above the upper disc on a shaft extending from the pivot arm through the upper disc; and
a guide pin extending from the pivot arm into an associated guide slot formed in the lower disc.

Embodiment 75

The system of Embodiment 74, wherein a first end of each guide slot formed in the lower disc is closer to a radial center of the lower disc than a second end of the guide slot.

Embodiment 76

The system of any one of Embodiments 70 to 75, wherein the moving assembly further comprises a drive mechanism comprising:
a motor having an output shaft and a drive wheel; and
a drive belt coupling the drive wheel to the carousel.

Embodiment 77

The system of Embodiment 76, wherein the carousel includes peripheral gear teach for engagement by the drive belt.

Embodiment 78

The system of any one of Embodiments 42-77, wherein the print head comprises a thermal print head.

Embodiment 79

A method for processing a sample material within a sample processing system, the method comprising:
(a) with a code reading device, automatically reading first machine-readable indicia on a surface of a first sample container containing a volume of a sample material, wherein information relating to the sample material contained in the first sample container is encoded in the first machine-readable indicia;
(b) automatically applying second machine-readable indicia on a curved surface of a second sample container,
wherein the second machine-readable indicia applied to the curved surface includes indicia relating to the first machine-readable indicia read from the first sample container in step (a), and
wherein automatically applying the second machine-readable indicia on the curved surface comprises printing the second machine-readable indicia directly onto the curved surface with a printing module comprising:
(i) a print head;
(ii) one or more contact elements configured to hold the second sample container with respect to the print head so as to hold the curved surface in an operative position with respect to the print head; and
(iii) a moving assembly configured to hold the second sample container and rotate the second sample container so as to move the curved surface with respect to the print head; and
(c) with an automated substance transfer device, automatically transferring an amount of sample material from the first sample container to the second sample container.

Embodiment 80

The method of Embodiment 79, further comprising the step of moving a second sample container from an input rack to the printing module with a robotic pick-and-place mechanism prior to step (b).

Embodiment 81

The method of Embodiment 79 or 80, further comprising the step of moving a second sample container from the printing module to a sample processing station with a robotic pick-and-place mechanism after step (b) and prior to step (c).

Embodiment 82

The method of Embodiment 81, further comprising the step of moving the second sample container from the sample processing station to an output rack with the robotic pick-and-place mechanism after step (c).

Embodiment 83

The method of any one of Embodiments 79 to 82, wherein the first machine-readable indicia comprise a first barcode and the second machine readable indicia comprise a second barcode.

Embodiment 84

The method of Embodiment 83, wherein the first and second barcodes are at least partially identical.

Embodiment 85

The method of any one of Embodiments 79 to 84, wherein the second sample container initially includes a blank label and the second machine readable indicia are printed onto the blank label.

Embodiment 86

The method of any one of Embodiments 79 to 85, wherein the print head is a thermal print head and the curved surface comprises thermally sensitive print media.

Embodiment 87

The method of any one of Embodiments 79 to 86, wherein the information relating to the sample material comprises sample-identifying information.

Embodiment 88

The method of any one of Embodiments 79 to 87, wherein the information relating to the sample material comprises sample-identifying information, and wherein the second machine-readable indicia applied onto the curved surface of the second sample container are at least partially identical to the first machine-readable indicia on the first sample container.

Embodiment 89

The method of Embodiment 88, wherein the second machine-readable indicia applied onto the curved surface of the second sample container includes additional machine-readable indicia that are different from the first machine-readable indicia on the first sample container, wherein information relating to one or more of time, volume, sample type, reagents, test procedures, test results, and errors is encoded in the additional machine-readable indicia.

Embodiment 90

A method for controlling a printing process by which a print head prints an image onto predetermined printable area of a label, the method comprising:
 (a) effecting relative movement between a timing mark sensor and the label;
 (b) during step (a), detecting a position of a timing mark on with a timing mark sensor;
 (c) after step (b), effecting relative movement between the print head and the label to position the print head at an image position at a specified distance from the position of the timing mark detected in step (b);
 (d) activating the print head; and
 (e) during step (d) effecting relative movement between the print head and the label for a specified image distance to print the image onto the printable area.

Embodiment 91

The method of Embodiment 90, wherein the image comprises a barcode.

Embodiment 92

The method of Embodiment 90 or 91, wherein the label is disposed on a curved surface of an article, and wherein effecting relative movement between the label and the timing mark sensor and between the label and the print head comprises rotating the article with respect to the timing mark sensor and the print head.

Embodiment 93

The method of any one of Embodiments 90 to 92, wherein the timing mark sensor is configured to detect reflectivity of a surface passing before the timing mark sensor, and step (b) comprises detecting the reflectivity of portions of the label passing by the timing mark sensor, wherein the reflectivity of the timing mark is different from the reflectivity of the remaining portions of the label passing by the timing mark sensor.

Embodiment 94

The method of any one of Embodiments 90-93, further comprising detecting the presence of the label before performing step (a).

Embodiment 95

The method of Embodiment 94, wherein the presence of the label is detected by the timing mark sensor based on a change in reflectivity due to the presence of the label that exceeds a predetermined print-surface-present threshold.

Embodiment 96

The method of Embodiment 93, further comprising generating a waveform from the output of the timing mark sensor based on the reflectivity of the portion of the label passing by the timing mark sensor, and wherein the timing mark is sensed by detecting a change in the waveform that exceeds a predefined timing mark threshold.

Embodiment 97

The method of Embodiment 96, further comprising detecting a first edge of the timing mark based on the change in the waveform falling below a negative timing mark threshold, and detecting a second edge of the timing mark based on the change in the waveform rising above a positive timing mark threshold.

Embodiment 98

The method of Embodiment 96 or 97, wherein the waveform comprises a plurality of data points sequentially-recorded from the output of the timing mark sensor and detecting a change in the waveform comprises comparing a first waveform value for a current data point with a second waveform value for a data point recorded at a predefined period earlier than the current data point to determine if the first waveform value varies from the second waveform value by more than the predefined timing mark threshold.

Embodiment 99

The method of any one of Embodiments 90 to 98, further comprising the step of printing a timing mark modifier that is detectable by the timing mark sensor onto the label to indicate that the label has been printed on.

Embodiment 100

The method of Embodiment 99, wherein printing the timing mark modifier comprises printing an image that alters the timing mark in a manner that is detectable by the timing mark sensor.

Embodiment 101

The method of Embodiment 99, wherein printing the timing mark modifier comprises printing an additional, mark distinct from the timing mark.

Embodiment 102

The method of any one of Embodiments 99 to 101, wherein step (c) comprises effecting relative movement between the print head and the label for a first predefined distance to place the print head at a print start position over the timing mark, and wherein printing the timing mark modifier comprises activating the print head and effecting a relative movement between the print head and the label.

Embodiment 103

The method of Embodiment 102, wherein printing the timing mark modifier comprises:
activating the print head and effecting a relative movement between the print head and the label for a first period;
terminating the first period when the timing mark is detected with the timing mark sensor; and
activating the print head and effecting a relative movement between the print head and the label for a second period defined by a specified amount of relative movement between the print head and the label.

Embodiment 104

The method of Embodiment 102 or 103, wherein step (c) further comprises effecting relative movement between the print head and the label for a third predefined distance without the print head activated to create a print gap following the timing mark modifier, wherein after relative movement for the third predefined distance, the print head is at the printable area.

Embodiment 105

The method of any one of Embodiments 90 to 104, wherein step (b) comprises locating a leading edge and a trailing edge of the timing mark relative to the direction of relative movement between the timing mark sensor and the label; and step (c) comprises effecting relative movement between the print head and the label to position the print head at the image position at the specified distance from the position of the trailing edge of the timing mark.

Embodiment 106

The method of any one of Embodiments 93 to 105, further comprising the step of calibrating the luminance of the timing mark sensor by:
setting the luminance of the timing mark sensor to a first level that will cause the output of the timing mark sensor to exceed an upper output limit; and
periodically changing the luminance of the timing mark sensor while effecting relative movement between the timing mark sensor and the label until the output of the timing mark sensor is between a lower output limit and the upper output limit throughout movement of the sensor relative to the entire label.

Embodiment 107

The method of any one of Embodiments 90 to 106, further comprising the step of determining the length of the timing mark and comparing the determined length of the timing mark to an expected length of the timing mark.

Embodiment 108

The method of Embodiment 107, further comprising completing steps (c) to (e) only if the length of the timing mark is within a predetermined range of the expected length of the timing mark.

Embodiment 109

The method of Embodiment 97, further comprising the step of determining the length of the timing mark and comparing the determined length of the timing mark to an expected length, wherein determining the length of the timing mark comprises:
computing a first point on the waveform where the change in the waveform falls below the negative timing mark threshold;
computing a second point on the waveform where the change in the waveform rises above the negative timing mark threshold;
computing a third point on the waveform where the change in the waveform rises above the positive timing mark threshold;
computing a fourth point on the waveform where the change in the waveform falls below the positive timing mark threshold; and
computing the length of the timing mark as the amount of relative movement between the timing mark sensor and the label between a point bisecting the first and second points and a point bisecting the third and fourth points.

Embodiment 110

The method of any one of Embodiments 90 to 109, further comprising:
after step (e), effecting relative movement between the timing mark sensor and the label;
(g) during step (f), with the timing mark sensor, detecting a position of the timing mark on the label;

(h) determining the amount of relative movement between the timing mark sensor and the label when the timing mark is detected in step (g); and (i) comparing the amount of relative movement detected in step (h) with an expected distance between an end of the image printed in step (e) and the timing mark.

Embodiment 111

The method of any one of Embodiments 93 to 110, wherein the timing mark is darker than its surroundings so that reflectivity of the timing mark is less than the reflectivity of its surroundings.

Embodiment 112

The method of any one of Embodiments 93 to 110, wherein the timing mark is lighter than its surroundings so that reflectivity of the timing mark is greater than the reflectivity of its surroundings.

Embodiment 113

The method of Embodiment 99 or 100, wherein printing a timing mark modifier comprises printing an extension to increase the length of the timing mark.

Embodiment 114

The method of any one of Embodiments 90 to 98, wherein the timing mark comprises a cut-out in the label.

Embodiment 115

The method of any one of Embodiments 90 to 98, wherein the timing mark comprises one or more encoder ticks of a series of encoder ticks.

Embodiment 116

The method of any one of Embodiments 90 to 92, wherein the timing mark comprises a physical feature formed on a surface of an article to which the label is affixed.

Embodiment 117

The method of any one of Embodiments 90 to 99, wherein the timing mark comprises a 1-D or 2-D barcode.

Embodiment 118

The method of Embodiment 99, wherein the timing mark comprises a 1-D or 2-D barcode, and wherein printing the timing mark modifier comprises printing a 1-D or 2-D barcode.

Embodiment 119

The method Embodiment 117, wherein the timing mark comprises a 2-D barcode, and detecting a position of the timing mark comprises identifying with a 2-D barcode reader a position of a known coordinate within the 2D barcode.

Embodiment 120

The method of Embodiment 117, wherein the timing mark comprises a 1-D barcode, and detecting a position of the timing mark comprises identifying a leading edge of the 1D barcode as the first location at which a 1-D barcode reader can read the 1-D barcode.

Embodiment 121

A method for controlling a printing process by which a print head prints an image onto a label affixed to a tube positioned adjacent to the print head and adjacent to a sensor configured to detect optical and/or physical features of the label, the method comprising:

(a) transmitting a command to the sensor to detect the presence of the label affixed to the tube, wherein the sensor either:

(1) fails to generate a signal indicating the presence of the label, or (2) generates a signal indicating the presence of the label;

(b) if the sensor generates a signal indicating the presence of the label in step (a), then transmitting a command to the sensor to detect a position of a timing mark on the label, wherein the sensor fails to generate a signal indicating the position of a timing mark on the label; and (c) if the sensor fails to generate a signal indicating the presence of the label in step (a) or the sensor fails to generate a signal indicating the position of a timing mark on the label in step (b), then selectively activating the print head while effecting relative movement between the print head and the label to print multiple alternate images at multiple positions on the label.

Embodiment 122

A method for controlling a printing process by which a print head prints an image onto a label affixed to a tube positioned adjacent to the print head and adjacent to a sensor configured to detect optical and/or physical features of the label, the method comprising:

(a) transmitting a command to the sensor to detect the presence of the label affixed to the tube, wherein the sensor fails to generate a signal indicating the presence of the label; and (b) after step (a), selectively activating the print head while effecting relative movement between the print head and the label to print multiple alternate images at multiple positions on the label.

Embodiment 123

A method for controlling a printing process by which a print head prints an image onto a label affixed to a tube positioned adjacent to the print head and adjacent to a sensor configured to detect optical and/or physical features of the label, the method comprising:

(a) detecting the presence of the label affixed to the tube with the sensor;

(b) after step (a), transmitting a command to the sensor to detect a position of a timing mark on the label, wherein the sensor fails to generate a signal indicating the position of a timing mark on the label; and (c) after step (b), selectively activating the print head while effecting relative movement between the print head and the label to print multiple alternate images at multiple positions on the label.

While the subject matter of the present disclosure has been described and shown in considerable detail with reference to certain illustrative embodiments, including various combinations and sub-combinations of features, those skilled in the art will readily appreciate other embodiments and variations and modifications thereof as encompassed within the scope of the disclosure. Moreover, the descriptions of such embodiments, combinations, and sub-combinations is not intended to convey that the subject matter requires features or combinations of features other than those expressly recited in the claims. Accordingly, the subject matter is intended to include all modifications and variations encompassed within the scope of the following appended claims.

The invention claimed is:

1. A system for processing a sample comprising:
a sample transfer apparatus configured to remove an amount of sample material from a first container and dispense at least a portion of the removed sample material in a second container;
a code reading device configured to read a first machine-readable graphic code on a surface of the first container, the first machine-readable graphic code having encoded therein information relating to the sample material contained in the first container;
a controller configured to generate a second machine-readable graphic code having encoded therein information relating to the information encoded in the first machine-readable graphic code; and
a printing module configured and controlled to print the second machine-readable graphic code on a curved surface of the second container, the printing module comprising:
(A) an expandable printing mechanism including a print head and configured and controlled to be selectively:
(1) expanded to an open configuration for enabling the second container to be received within or removed from the printing module, and
(2) contracted to a printing configuration placing the curved surface of the second container in an operative printing position with respect to the print head and maintaining the curved surface in the operative printing position with respect to the print head during relative movement of the curved surface with respect to the print head; and
(B) a moving assembly configured and controlled to:
(1) grasp the received second container and effect relative movement between the curved surface of the second container and the print head when the expandable printing mechanism is in the printing configuration, and
(2) release the article when the expandable printing mechanism is in the open configuration, thereby allowing the article to be removed from the printing module.

2. The system of claim 1, wherein the sample transfer apparatus comprises a pipettor carried on a robotic arm.

3. The system of claim 1, further comprising a pick-and-place mechanism configured and controlled to selectively move either or both of the first and second containers from a first location within the system to a second location within the system.

4. The system of claim 3, wherein the pick-and-place mechanism comprises a container gripper carried on a robotic arm.

5. The system of claim 1, wherein the printing module further comprises a housing at least partially enclosing the expandable printing mechanism and the moving assembly.

6. The system of claim 5, further including an opening formed in the housing through which the second container can be moved into or out of the housing of the printing module.

7. The system of claim 1, wherein the expandable printing mechanism comprises:
a first support element having one or more contact element(s) operatively supported thereon; and
a second support element supporting the print head thereon,
wherein the first support element and the second support element are configured for relative movement with respect to each other between the open configuration of the expandable printing mechanism and the printing configuration of the expandable printing mechanism, and wherein the contact element(s) are configured to contact the second container received within the printing module to hold the curved surface in the operative position with respect to the print head when the expandable printing mechanism is in the printing configuration.

8. The system of claim 7, wherein the expandable printing mechanism further comprises an expander mechanism configured to effect relative movement of the first and second support elements between the open configuration and the printing configuration.

9. The system of claim 7, wherein the one or more contact elements comprise a first roller and a second roller rotatably mounted to the first support element.

10. The system of claim 9, wherein
the first roller is axially elongated, and
the second roller comprises, extending axially along the length of the roller, a first head portion that is of a first diameter, an extension portion that is of a second diameter that is less than the first diameter, and a second head portion that is of a third diameter that is greater than the second diameter.

11. The system of claim 10, wherein the third diameter is equal to the first diameter.

12. The system of claim 10 wherein the first roller is cylindrical.

13. The system of claim 10, wherein the first roller has a varying diameter that increases from each axial end of the roller to the axial middle of the roller.

14. The system of claim 9, wherein
the first support element comprises a roller bracket having an upper flange, a lower flange, and a web extending between the upper and lower flanges, and wherein the first roller and the second roller are rotatably mounted between the first and second flanges;
the second support element comprises a print head bracket having an upper flange, a lower flange, and a web extending between the upper and lower flanges, the roller bracket and the print head bracket being oriented such that the webs of the roller bracket and the print head bracket are generally parallel to one another; and
the roller bracket and the print head bracket are pivotably mounted to a common pivot shaft so that the roller bracket and the print head bracket are pivotable with respect to each other in a hinge-wise fashion about the pivot shaft between the open configuration and the printing configuration.

15. The system of claim 8, wherein:
the first and second support elements are pivotably mounted to a common pivot shaft so that the first and second support elements are pivotable with respect to each other in a hinge-wise fashion about the pivot shaft between the open configuration and the printing configuration, and wherein the expander mechanism comprises:
a driven shaft located between the first and second support elements, the driven shaft being generally parallel to the pivot shaft; and
a cam element attached to and rotatable with the driven shaft and in contact with both the first and second support elements, wherein the cam element has a varying dimension so that in one orientation of the cam element, portions of the cam element contacting the first and second support elements hold the first and second support elements apart by a first distance corresponding to the open configuration of the expandable printing mechanism and in another orientation of the cam element, portions of the cam element contacting the first and second support elements hold the first and second support elements apart by a second distance corresponding to the printing configuration of the expandable printing mechanism.

16. The system of claim 15, wherein the cam element comprises a cam disc fixed to the driven shaft and coaxial therewith, the cam disc having a variable radius so that in a first rotational position of the cam disc, portions of the cam disc having a first radius are in contact with the first and second support elements and holding the first and second support elements apart by the first distance corresponding to the open configuration, and in a second rotational position of the cam disc, portions of the cam disc having a second radius that is smaller than the first radius are in contact with the first and second support elements and holding the first and second support elements apart by the second distance corresponding to the printing configuration.

17. The system of claim 15, wherein the expander mechanism further comprises a spring extending between the first and second support elements and configured to bias the first and second support elements into contact with the cam element.

18. The system of claim 15, wherein each of the first and second support elements further includes a roller bearing mounted thereon, wherein the cam element contacts the roller bearing of each of the first and second support elements.

19. The system of claim 15, further comprising a drive mechanism comprising:
a pulley wheel coaxially mounted to the driven shaft;
a motor having an output shaft and a drive wheel; and
a drive belt coupling the drive wheel to the pulley wheel.

20. The system of claim 15, wherein the expander mechanism further comprises a rotational position sensor configured to detect a rotational position of the driven shaft and cam element.

21. The system of claim 20, wherein the rotational position sensor comprises:
an index wheel coaxially coupled to the driven shaft and having one or more detectable features formed therein or attached thereto at specified rotational positions; and
an optical sensor configured to detect the one or more detectable features as the driven shaft and the index wheel rotate with respect to the optical sensor.

22. The system of claim 15, further comprising a hand wheel mounted to the driven shaft and configured to enable manual rotation of the driven shaft and the cam element.

23. The system of claim 7, wherein the second support element comprises a print head platen on which the print head is mounted.

24. The system of claim 23, wherein the print head platen is configured and mounted so that its position on the second support element can be laterally adjusted.

25. The system of claim 24, further comprising a platen shaft mounted to the second support element, wherein the platen shaft extends through a portion of the print head platen, so as to permit lateral movement of the print head platen along the platen shaft.

26. The system of claim 25, further comprising a platen adjustment lever pivotably mounted to the second support element and including a contact point in contact with a portion of the print head platen and configured such that pivoting movement the platen adjustment lever effects lateral movement of the print head platen along the platen shaft.

27. The system of claim 26, wherein the platen adjustment lever includes a protuberance that is configured to be inserted into one of a plurality of holes formed in the second support element to secure the platen adjustment lever at a selected rotational position.

28. The system of claim 1, further comprising a timing mark sensor configured to detect a timing mark on the curved surface.

29. The system of claim 1, wherein the moving assembly comprises:
a carousel configured for powered rotation; and
moveable gripper elements configured to be movable between a release position permitting an article to be placed within or removed from the printing module and a gripping position for securing the second container with respect to the carousel so that the article rotates with the carousel.

30. The system of claim 29, wherein each gripper element comprises a gripper assembly that is coupled to the carousel and is configured so that rotation of the carousel in a first direction causes all the gripper assemblies to move radially inwardly to the gripping position with respect to the second container placed between the gripper assemblies and rotation of the carousel in a second direction opposite the first direction causes all the gripper assemblies to move radially outwardly to the release position with respect to the second container.

31. The system of claim 30, comprising three gripper assemblies.

32. The system of claim 29, wherein the carousel comprises:
an upper disc; and
a lower disc, coaxially arranged with the upper disc, the upper and lower discs being rotatable relative to one another.

33. The system of claim 32, wherein each gripper element comprises a pivoting gripper assembly comprising:
a pivot arm disposed between the upper disc and the lower disc of the carousel and pivotably attached to the upper disc;
a knurled wheel rotatably mounted above the upper disc on a shaft extending from the pivot arm through the upper disc; and
a guide pin extending from the pivot arm into an associated guide slot formed in the lower disc.

34. The system of claim 33, wherein a first end of each guide slot formed in the lower disc is closer to a radial center of the lower disc than a second end of the guide slot.

35. The system of claim 29, wherein the moving assembly further comprises a drive mechanism comprising:
a motor having an output shaft and a drive wheel; and
a drive belt coupling the drive wheel to the carousel.

36. The system of claim 35, wherein the carousel includes peripheral gear teach for engagement by the drive belt.

37. The system of claim 1, wherein the print head comprises a thermal print head.

38. A method for processing a sample material within a sample processing system, the method comprising:
(a) with a code reading device, automatically reading first machine-readable indicia on a surface of a first sample container containing a volume of a sample material, wherein information relating to the sample material contained in the first sample container is encoded in the first machine-readable indicia;
(b) automatically applying second machine-readable indicia on a curved surface of a second sample container, wherein the second machine-readable indicia applied to the curved surface includes indicia relating to the first machine-readable indicia read from the first sample container in step (a), and
wherein automatically applying the second machine-readable indicia on the curved surface comprises thermal printing the second machine-readable indicia directly onto the curved surface with a printing module comprising:
(i) a print head;
(ii) one or more contact elements configured to hold the second sample container with respect to the print head so as to hold the curved surface in an operative position with respect to the print head; and
(iii) a moving assembly configured to hold the second sample container and rotate the second sample container so as to move the curved surface with respect to the print head; wherein the moving assembly comprises: a carousel configured for powered rotation; and moveable gripper elements configured to be movable between a release position permitting an article to be placed within or removed from the printing module and a gripping position for securing the second container with respect to the carousel so that the article rotates with the carousel; wherein each gripper element comprises a gripper assembly that is coupled to the carousel and is configured so that rotation of the carousel in a first direction causes all the gripper assemblies to move radially inwardly to the gripping position with respect to the second container placed between the gripper assemblies and rotation of the carousel in a second direction opposite the first direction causes all the gripper assemblies to move radially outwardly to the release position with respect to the second container; and
(c) with an automated substance transfer device, automatically transferring an amount of sample material from the first sample container to the second sample container; and
wherein the print head is a thermal print head and the curved surface comprises thermally sensitive print media.

39. The method of claim 38, further comprising the step of moving a second sample container from an input rack to the printing module with a robotic pick-and-place mechanism prior to step (b).

40. The method of claim 38, further comprising the step of moving a second sample container from the printing module to a sample processing station with a robotic pick-and-place mechanism after step (b) and prior to step (c).

41. The method of claim 40, further comprising the step of moving the second sample container from the sample processing station to an output rack with the robotic pick-and-place mechanism after step (c).

42. The method of claim 38, wherein the first machine-readable indicia comprise a first barcode and the second machine readable indicia comprise a second barcode.

43. The method of claim 42, wherein the first and second barcodes are at least partially identical.

44. The method of claim 38, wherein the second sample container initially includes a blank label and the second machine readable indicia are printed onto the blank label.

45. The method of claim 38, wherein the information relating to the sample material comprises sample-identifying information.

46. The method of claim 38, wherein the information relating to the sample material comprises sample-identifying information, and wherein the second machine-readable indicia applied onto the curved surface of the second sample container are at least partially identical to the first machine-readable indicia on the first sample container.

47. The method of claim 46, wherein the second machine-readable indicia applied onto the curved surface of the second sample container includes additional machine-readable indicia that are different from the first machine-readable indicia on the first sample container, wherein information relating to one or more of time, volume, sample type, reagents, test procedures, test results, and errors is encoded in the additional machine-readable indicia.

* * * * *